United States Patent
Craik et al.

(10) Patent No.: US 7,227,009 B2
(45) Date of Patent: Jun. 5, 2007

(54) MT-SP1 POLYNUCLEOTIDES AND POLYPEPTIDES

(75) Inventors: Charles S. Craik, San Francisco, CA (US); Toshihiko Takeuchi, San Francisco, CA (US); Marc Shuman, San Francisco, CA (US)

(73) Assignee: Catalyst Biosciences, Inc., South San Francisco, CA (US)

( * ) Notice: Subject to any disclaimer, the term of this patent is extended or adjusted under 35 U.S.C. 154(b) by 0 days.

(21) Appl. No.: 11/253,869

(22) Filed: Oct. 18, 2005

(65) Prior Publication Data

US 2006/0104979 A1 May 18, 2006

Related U.S. Application Data

(63) Continuation of application No. 09/410,362, filed on Sep. 30, 1999, now Pat. No. 7,030,231.

(51) Int. Cl.
*C12N 15/11* (2006.01)

(52) U.S. Cl. .................. 536/23.1; 435/320.1; 435/325; 435/69.1

(58) Field of Classification Search ..................... None
See application file for complete search history.

(56) References Cited

U.S. PATENT DOCUMENTS

| | | | |
|---|---|---|---|
| 5,482,848 A | 1/1996 | Dickson et al. | |
| 5,972,616 A * | 10/1999 | O'Brien et al. | ................ 435/6 |
| 2003/0119168 A1 | 6/2003 | Madison et al. | |

FOREIGN PATENT DOCUMENTS

WO   WO 99/42120   *   8/1999

OTHER PUBLICATIONS

Bork, et al. The CUB Domain: A Widespread Module in Developmentally Regulated Proteins. J. Med. Biol. 1993; 539-545.
EST Accession No. aa219372.
EST Accession No. aa459076.
EST Accession No. w39209.
GenBank Accession No. U20428.
Ishibashi, et al. Sp1 Decoy Transfected to Carcinoma Cells Suppresses the Expression of Vascular Endothelial Growth Factor, Transforming Growth Factor β1, and Tissue Factor and Also Cell Growth and Invasion Activities. Cancer Res. 2000; 60(20):6531-6536.
Kang, et al. Identification of cDNAs encoding two novel rat pancreatic serine proteases. Gene. 1992; 110:181-187.
Kim, et al. Cloning and chromosomal mapping of gene isolated from thymic stromal cells encoding a new mouse type II membrane serine protease, epithin, containing four LDL receptor modules and two CUB domains. Immunogenetics. 1999; 49:420-428.
Kitamoto, et al. Enterokinase, the initiator of intestinal digestion, is a mosaic protease composed of a distinctive assortment of domains. Proc. Natl. Acad. Sci. 1994; 91:7588-7592.
Krieger, et al. Structures and Functions of Multiligand Liprotein Receptors: Macrophage Scavenger Receptors and LDL Receptor-Related Protein (LRP). Annu. Rev. Biochem. 1994; 63:601-637.
Leytus, et al. A Novel Trypsin-like Serine Protease (Hepsin) with a Putative Transmembrane Domain Expressed by Human Liver and Hepatoma Cells. Biochemistry. 1988; 27:1067-1074.
Lin, et al. Molecular Cloning cDNA for Matriptase, a Metrix-degrading Serine Protease with Trypsin-like Activity. J. Biol. Chem. 1999; 274(26):18231-18236.
Lin, et al. Purification and Characterization of a Complex Containing Matriptase and a Kunitz-type Serine Protease Inhibitor from Human Milk. J. Biol. Chem. 1999; 274:18237-18242.
Paoloni-Giacobino, et al. Cloning of the TMPRSS2 Gene, Which Encodes a Novel Serine Protease with Transmembrane LDLRA, and SRCR Domains and Maps to 21q22.3. Genomics. 1997; 44:309-320.
Perona, et al. Evolutionary Divergence of Substrate Specificity within the Chymotrypsin-like Serine Protease Fold. J. Biol. Chem. 1997; 272:29987-29990.
Persona, et al. Structural basis of substrate specificity in the serine proteases. Protein Science. 1995; 4:337-360.
Sakanari, et al. Serine proteases from nematode and protozoan parasites: Isolation of sequence homologs using generic molecular probes. Proc. Natl. Acad. Sci. 1989; 86:4863-4867.
Takeuchi, et al. Cellular Localization of Membrane-type Serine Protease 1 and Identification of Protease-activated receptor-2 and Single-chain Urokinase-type Plasminogen Activator as Substrates. J. Biol. Chem. 2000; 275(34):26333-26342.
Takeuchi, et al. Reverse biochemistry: Use of macromolecular protease inhibitors to dissect complex biological processes and identify a membrane-type serine protease protease in epithelial cancer and normal tissue. Proc. Natl. Acad. Sci. 1999; 96(20):11054-11061.
Wiegand, et al. Cloning of cDNA encoding human brain trypsinogen and characterization of its product. Gene. 1993; 136:167-175.
Yamada, et al. Isolation and characterization of three novel serine protease genes from *Xenopus laevis*. Gene. 2000; 252:209-216.
Yamaoka, et al. Cloning and Characterization of the cDNA for Human Airway Trypsin-like Protease. J. Biol. Chem. 1998; 273:11895-11901.

\* cited by examiner

*Primary Examiner*—Misook Yu
(74) *Attorney, Agent, or Firm*—Wilson Sonsini Goodrich & Rosati

(57) ABSTRACT

This invention provides a novel membrane-type serine protease (designated MT-SP1) elevated expression of which is associated with cancer. In one embodiment, this invention provides a method obtaining a prognosis or of detecting or staging a cancer in an organism. The method involves providing a biological sample from the organism and detecting the level of a membrane type serine protease 1 (MT-SP1) in the sample, where an elevated level of the membrane-type serine protease, as compared to the level of the protease in a biological sample from a normal healthy organism indicates the presence or stage of the cancer.

9 Claims, 8 Drawing Sheets

LDL REPEATS

```
SEQ ID NO: 41 MT-SP1-1 (453-487)  C..PGQFTCR T..GRCI.RK ELRCDGWADC .....LDSDE..LA  CS----------
              MT-SP1-2 (488-524)  CDAGHQFTCK NKF..CKPLF .NVCDSVNDC GDNSDE..QG  CS----------
              MT-SP1-3 (525-566)  C.PAQTFRCS N..GKCLSK. SQQCNGKDDC GDGSDE..AS  CPKVNVVT----
              MT-SP1-4 (567-603)  C.TKHTYRCL N..GLCLSKG NPECDGKEDC SDGSDE..ID  CD----------

SEQ ID NO: 42 LDLR1    (6-46)     C.ERNEFQCQ.D..GKCISY. KMVCDGSAEC QDGSDESQET  CLSVT-------
              LDLR2    (47-87)    C.KSGDFSCG GRVNRCIPQF .NRCDGQVDC DNGSDE..CG  CPPKT-------
              LDLR3    (88-126)   C.SQDEFRCH D..GKCISR. QPVCD.SRDC LDGSDE..AS  CPVLT-------
              LDLR4    (127-175)  C.GPASFQCN S..STCIPQL .MACDNDPDC EDGSDEWPQR  CRGLYVFQGDSSP
              LDLR5    (176-214)  C.BAPEFHCL S..GECI.HS SNRCDGGPDC KDKSDE..EN  CAVAT-------
              LDLR6    (215-254)  C.RPDEFQCS D..GNCI.HG SRQCDRETDC KDWSDE..VG  CVNYTL------
              LDLR7    (255-296)  CBGPNKFTCH S..GECITDD K.VCNMARDC RDWSDEPIKE  CGINE-------

CONSENSUS                         C--------- C--------- ---G--CI-- -N-CDG--DC  -DGSDE-----C--------
```

|----S-S----|
      |------S-S--------|
|---------S-S--------------|

Fig. 4C

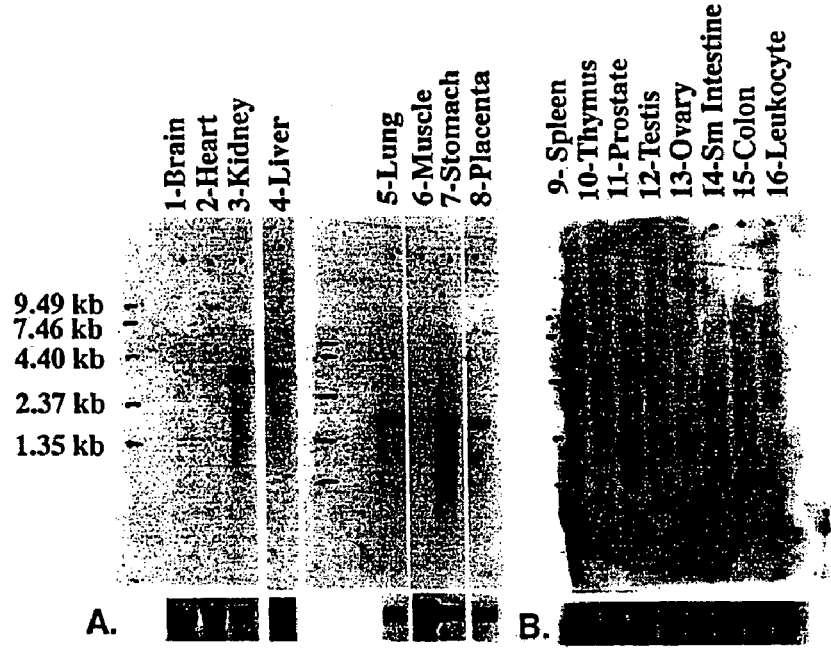
*Fig. 5A*  *Fig. 5B*

SEQUENCE LISTING

<160> NUMBER OF SEQ ID NOS: 83

<210> SEQ ID NO 1
<211> LENGTH: 3142
<212> TYPE: DNA
<213> ORGANISM: Homo sapiens
<220> FEATURE:
<221> NAME/KEY: CDS
<222> LOCATION: (37)..(2601)

<400> SEQUENCE: 1

```
cgaggatcct gagacccgcg agcggcctcg gggacc atg ggg agc gat cgg gcc        54
                                        Met Gly Ser Asp Arg Ala
                                        1               5 cgc aag ggc gga ggg ggc ccg aag gac ttc ggc gcg gga ctc aag tac       102
Arg Lys Gly Gly Gly Gly Pro Lys Asp Phe Gly Ala Gly Leu Lys Tyr
            10                  15                  20 aac tcc cgg cac gag aaa gtg aat ggc ttg gag gaa ggc gtg gag ttc       150
Asn Ser Arg His Glu Lys Val Asn Gly Leu Glu Glu Gly Val Glu Phe
        25                  30                  35 ctg cca gtc aac aac gtc aag aag gtg gaa aag cat ggc ccg ggg cgc       198
Leu Pro Val Asn Asn Val Lys Lys Val Glu Lys His Gly Pro Gly Arg
    40                  45                  50 tgg gtg gtg ctg gca gcc gtg ctg atc ggc ctc ctc ttg gtc ttg ctg       246
Trp Val Val Leu Ala Ala Val Leu Ile Gly Leu Leu Leu Val Leu Leu
55                  60                  65                  70
```

| | | |
|---|---|---|
| ggg atc ggc ttc ctg gtg tgg cat ttg cag tac cgg gac gtg cgt gtc<br>Gly Ile Gly Phe Leu Val Trp His Leu Gln Tyr Arg Asp Val Arg Val<br>75                          80                        85 | 294 |
| cag aag gtc ttc aat ggc tac atg agg atc aca aat gag aat ttt gtg<br>Gln Lys Val Phe Asn Gly Tyr Met Arg Ile Thr Asn Glu Asn Phe Val<br>                90                        95                      100 | 342 |
| gat gcc tac gag aac tcc aac tcc act gag ttt gta agc ctg gcc agc<br>Asp Ala Tyr Glu Asn Ser Asn Ser Thr Glu Phe Val Ser Leu Ala Ser<br>                105                     110                     115 | 390 |
| aag gtg aag gac gcg ctg aag ctg ctg tac agc gga gtc cca ttc ctg<br>Lys Val Lys Asp Ala Leu Lys Leu Leu Tyr Ser Gly Val Pro Phe Leu<br>120                        125                     130 | 438 |
| ggc ccc tac cac aag gag tcg gct gtg acg gcc ttc agc gag ggc agc<br>Gly Pro Tyr His Lys Glu Ser Ala Val Thr Ala Phe Ser Glu Gly Ser<br>135                     140                     145                     150 | 486 |
| gtc atc gcc tac tac tgg tct gag ttc agc atc ccg cag cac ctg gtg<br>Val Ile Ala Tyr Tyr Trp Ser Glu Phe Ser Ile Pro Gln His Leu Val<br>                155                     160                     165 | 534 |
| gag gag gcc gag cgc gtc atg gcc gag gag cgc gta gtc atg ctg ccc<br>Glu Glu Ala Glu Arg Val Met Ala Glu Glu Arg Val Val Met Leu Pro<br>170                        175                     180 | 582 |
| ccg cgg gcg cgc tcc ctg aag tcc ttt gtg gtc acc tca gtg gtg gct<br>Pro Arg Ala Arg Ser Leu Lys Ser Phe Val Val Thr Ser Val Val Ala<br>                185                     190                     195 | 630 |
| ttc ccc acg gac tcc aaa aca gta cag agg acc cag gac aac agc tgc<br>Phe Pro Thr Asp Ser Lys Thr Val Gln Arg Thr Gln Asp Asn Ser Cys<br>200                        205                     210 | 678 |
| agc ttt ggc ctg cac gcc cgc ggt gtg gag ctg atg cgc ttc acc acg<br>Ser Phe Gly Leu His Ala Arg Gly Val Glu Leu Met Arg Phe Thr Thr<br>215                        220                     225                     230 | 726 |
| ccc ggc ttc cct gac agc ccc tac ccc gct cat gcc cgc tgc cag tgg<br>Pro Gly Phe Pro Asp Ser Pro Tyr Pro Ala His Ala Arg Cys Gln Trp<br>                235                     240                     245 | 774 |
| gcc ctg cgg ggg gac gcc gac tca gtg ctg agc ctc acc ttc cgc agc<br>Ala Leu Arg Gly Asp Ala Asp Ser Val Leu Ser Leu Thr Phe Arg Ser<br>                  250                     255                     260 | 822 |
| ttt gac ctt gcg tcc tgc gac gag cgc ggc agc gac ctg gtg acg gtg<br>Phe Asp Leu Ala Ser Cys Asp Glu Arg Gly Ser Asp Leu Val Thr Val<br>                265                     270                     275 | 870 |
| tac aac acc ctg agc ccc atg gag ccc cac gcc ctg gtg cag ttg tgt<br>Tyr Asn Thr Leu Ser Pro Met Glu Pro His Ala Leu Val Gln Leu Cys<br>                280                     285                     290 | 918 |
| ggc acc tac cct ccc tcc tac aac ctg acc ttc cac tcc tcc cag aac<br>Gly Thr Tyr Pro Pro Ser Tyr Asn Leu Thr Phe His Ser Ser Gln Asn<br>295                        300                     305                     310 | 966 |
| gtc ctg ctc atc aca ctg ata acc aac act gag cgg cgg cat ccc ggc<br>Val Leu Leu Ile Thr Leu Ile Thr Asn Thr Glu Arg Arg His Pro Gly<br>                315                     320                     325 | 1014 |
| ttt gag gcc acc ttc ttc cag ctg cct agg atg agc agc tgt gga ggc<br>Phe Glu Ala Thr Phe Phe Gln Leu Pro Arg Met Ser Ser Cys Gly Gly<br>                330                     335                     340 | 1062 |
| cgc tta cgt aaa gcc cag ggg aca ttc aac agc ccc tac tac cca ggc<br>Arg Leu Arg Lys Ala Gln Gly Thr Phe Asn Ser Pro Tyr Tyr Pro Gly<br>                345                     350                     355 | 1110 |
| cac tac cca ccc aac att gac tgc aca tgg aac att gag gtg ccc aac<br>His Tyr Pro Pro Asn Ile Asp Cys Thr Trp Asn Ile Glu Val Pro Asn<br>                360                     365                     370 | 1158 |
| aac cag cat gtg aag gtg cgc ttc aaa ttc ttc tac ctg ctg gag ccc<br>Asn Gln His Val Lys Val Arg Phe Lys Phe Phe Tyr Leu Leu Glu Pro<br>375                        380                     385                     390 | 1206 |

```
ggc gtg cct gcg ggc acc tgc ccc aag gac tac gtg gag atc aat ggg      1254
Gly Val Pro Ala Gly Thr Cys Pro Lys Asp Tyr Val Glu Ile Asn Gly
            395                 400                 405 gag aaa tac tgc gga gag agg tcc cag ttc gtc gtc acc agc aac agc      1302
Glu Lys Tyr Cys Gly Glu Arg Ser Gln Phe Val Val Thr Ser Asn Ser
            410                 415                 420 aac aag atc aca gtt cgc ttc cac tca gat cag tcc tac acc gac acc      1350
Asn Lys Ile Thr Val Arg Phe His Ser Asp Gln Ser Tyr Thr Asp Thr
            425                 430                 435 ggc ttc tta gct gaa tac ctc tcc tac gac tcc agt gac cca tgc ccg      1398
Gly Phe Leu Ala Glu Tyr Leu Ser Tyr Asp Ser Ser Asp Pro Cys Pro
440                 445                 450 ggg cag ttc acg tgc cgc acg ggg cgg tgt atc cgg aag gag ctg cgc      1446
Gly Gln Phe Thr Cys Arg Thr Gly Arg Cys Ile Arg Lys Glu Leu Arg
455                 460                 465                 470 tgt gat ggc tgg gcc gac tgc acc gac cac agc gat gag ctc aac tgc      1494
Cys Asp Gly Trp Ala Asp Cys Thr Asp His Ser Asp Glu Leu Asn Cys
                475                 480                 485 agt tgc gac gcc ggc cac cag ttc acg tgc aag aac aag ttc tgc aag      1542
Ser Cys Asp Ala Gly His Gln Phe Thr Cys Lys Asn Lys Phe Cys Lys
            490                 495                 500 ccc ctc ttc tgg gtc tgc gac agt gtg aac gac tgc gga gac aac agc      1590
Pro Leu Phe Trp Val Cys Asp Ser Val Asn Asp Cys Gly Asp Asn Ser
            505                 510                 515 gac gag cag ggg tgc agt tgt ccg gcc cag acc ttc agg tgt tcc aat      1638
Asp Glu Gln Gly Cys Ser Cys Pro Ala Gln Thr Phe Arg Cys Ser Asn
520                 525                 530 ggg aag tgc ctc tcg aaa agc cag cag tgc aat ggg aag gac gac tgt      1686
Gly Lys Cys Leu Ser Lys Ser Gln Gln Cys Asn Gly Lys Asp Asp Cys
535                 540                 545                 550 ggg gac ggg tcc gac gag gcc tcc tgc ccc aag gtg aac gtc gtc act      1734
Gly Asp Gly Ser Asp Glu Ala Ser Cys Pro Lys Val Asn Val Val Thr
                555                 560                 565 tgt acc aaa cac acc tac cgc tgc ctc aat ggg ctc tgc ttg agc aag      1782
Cys Thr Lys His Thr Tyr Arg Cys Leu Asn Gly Leu Cys Leu Ser Lys
            570                 575                 580 ggc aac cct gag tgt gac ggg aag gag gac tgt agc gac ggc tca gat      1830
Gly Asn Pro Glu Cys Asp Gly Lys Glu Asp Cys Ser Asp Gly Ser Asp
            585                 590                 595 gag aag gac tgc gac tgt ggg ctg cgg tca ttc acg aga cag gct cgt      1878
Glu Lys Asp Cys Asp Cys Gly Leu Arg Ser Phe Thr Arg Gln Ala Arg
            600                 605                 610 gtt gtt ggg ggc acg gat gcg gat gag ggc gag tgg ccc tgg cag gta      1926
Val Val Gly Gly Thr Asp Ala Asp Glu Gly Glu Trp Pro Trp Gln Val
615                 620                 625                 630 agc ctg cat gct ctg ggc cag ggc cac atc tgc ggt gct tcc ctc atc      1974
Ser Leu His Ala Leu Gly Gln Gly His Ile Cys Gly Ala Ser Leu Ile
            635                 640                 645 tct ccc aac tgg ctg gtc tct gcc gca cac tgc tac atc gat gac aga      2022
Ser Pro Asn Trp Leu Val Ser Ala Ala His Cys Tyr Ile Asp Asp Arg
            650                 655                 660 gga ttc agg tac tca gac ccc acg cag tgg acg gcc ttc ctg ggc ttg      2070
Gly Phe Arg Tyr Ser Asp Pro Thr Gln Trp Thr Ala Phe Leu Gly Leu
            665                 670                 675 cac gac cag agc cag cgc agc gcc cct ggg gtg cag gag cgc agg ctc      2118
His Asp Gln Ser Gln Arg Ser Ala Pro Gly Val Gln Glu Arg Arg Leu
            680                 685                 690 aag cgc atc atc tcc cac ccc ttc ttc aat gac ttc acc ttc gac tat      2166
Lys Arg Ile Ile Ser His Pro Phe Phe Asn Asp Phe Thr Phe Asp Tyr
```

```
                                                                  2214
gac atc gcg ctg ctg gag ctg gag aaa ccg gca gag tac agc tcc atg
Asp Ile Ala Leu Leu Glu Leu Glu Lys Pro Ala Glu Tyr Ser Ser Met
            715                 720                 725

2262
gtg cgg ccc atc tgc ctg ccg gac gcc tcc cat gtc ttc cct gcc ggc
Val Arg Pro Ile Cys Leu Pro Asp Ala Ser His Val Phe Pro Ala Gly
        730                 735                 740

2310
aag gcc atc tgg gtc acg ggc tgg gga cac acc cag tat gga ggc act
Lys Ala Ile Trp Val Thr Gly Trp Gly His Thr Gln Tyr Gly Gly Thr
    745                 750                 755

2358
ggc gcg ctg atc ctg caa aag ggt gag atc cgc gtc atc aac cag acc
Gly Ala Leu Ile Leu Gln Lys Gly Glu Ile Arg Val Ile Asn Gln Thr
760                 765                 770

2406
acc tgc gag aac ctc ctg ccg cag cag atc acg ccg cgc atg atg tgc
Thr Cys Glu Asn Leu Leu Pro Gln Gln Ile Thr Pro Arg Met Met Cys
775                 780                 785                 790

2454
gtg ggc ttc ctc agc ggc ggc gtg gac tcc tgc cag ggt gat tcc ggg
Val Gly Phe Leu Ser Gly Gly Val Asp Ser Cys Gln Gly Asp Ser Gly
                795                 800                 805

2502
gga ccc ctg tcc agc gtg gag gcg gat ggg cgg atc ttc cag gcc ggt
Gly Pro Leu Ser Ser Val Glu Ala Asp Gly Arg Ile Phe Gln Ala Gly
            810                 815                 820

2550
gtg gtg agc tgg gga gac ggc tgc gct cag agg aac aag cca ggc gtg
Val Val Ser Trp Gly Asp Gly Cys Ala Gln Arg Asn Lys Pro Gly Val
        825                 830                 835

2598
tac aca agg ctc cct ctg ttt cgg gac tgg atc aaa gag aac act ggg
Tyr Thr Arg Leu Pro Leu Phe Arg Asp Trp Ile Lys Glu Asn Thr Gly
    840                 845                 850 gta tagggccgg ggcacccaag atgtgtacac ctgcggggcc acccatcgtc         2651
Val
855 cacccccagtg tgcacgcctg caggctggag actggaccgc tgactgcacc agcgccccca  2711
gaacatacac tgtgaactca atctccaggg ctccaaatct gcctagaaaa cctctcgctt    2771
cctcagcctc caaagtggag ctgggaggta aaggggagg acactggtgg ttctactgac     2831
ccaactgggg gcaaaggttt gaagacacag cctcccccgc cagccccaag ctgggccgag    2891
gcgcgtttgt gtatatctgc ctcccctgtc tgtaaggagc agcgggaacg gagcttcggg    2951
gcctcctcag tgaaggtggt ggggctgccg gatctgggct gtggggccct tgggccacgc    3011
tcttgaggaa gcccaggctc ggaggaccct ggaaaacaga cgggtctgag actgaaattg    3071
ttttaccagc tcccagggtg gacttcagtg tgtgtatttg tgtaaatgag taaacatttt    3131
tatttctttt t                                                         3142
```

<210> SEQ ID NO 2
<211> LENGTH: 855
<212> TYPE: PRT
<213> ORGANISM: Homo sapiens

<400> SEQUENCE: 2

Met Gly Ser Asp Arg Ala Arg Lys Gly Gly Gly Pro Lys Asp Phe
1               5                   10                  15

Gly Ala Gly Leu Lys Tyr Asn Ser Arg His Glu Lys Val Asn Gly Leu
            20                  25                  30

Glu Glu Gly Val Glu Phe Leu Pro Val Asn Asn Val Lys Lys Val Glu
        35                  40                  45

Lys His Gly Pro Gly Arg Trp Val Val Leu Ala Ala Val Leu Ile Gly
    50                  55                  60

-continued

```
Leu Leu Leu Val Leu Leu Gly Ile Gly Phe Leu Val Trp His Leu Gln
 65                  70                  75                  80

Tyr Arg Asp Val Arg Val Gln Lys Val Phe Asn Gly Tyr Met Arg Ile
                 85                  90                  95

Thr Asn Glu Asn Phe Val Asp Ala Tyr Glu Asn Ser Asn Ser Thr Glu
            100                 105                 110

Phe Val Ser Leu Ala Ser Lys Val Lys Asp Ala Leu Lys Leu Leu Tyr
        115                 120                 125

Ser Gly Val Pro Phe Leu Gly Pro Tyr His Lys Glu Ser Ala Val Thr
130                 135                 140

Ala Phe Ser Glu Gly Ser Val Ile Ala Tyr Tyr Trp Ser Glu Phe Ser
145                 150                 155                 160

Ile Pro Gln His Leu Val Glu Glu Ala Glu Arg Val Met Ala Glu Glu
                165                 170                 175

Arg Val Val Met Leu Pro Pro Arg Ala Arg Ser Leu Lys Ser Phe Val
            180                 185                 190

Val Thr Ser Val Val Ala Phe Pro Thr Asp Ser Lys Thr Val Gln Arg
        195                 200                 205

Thr Gln Asp Asn Ser Cys Ser Phe Gly Leu His Ala Arg Gly Val Glu
210                 215                 220

Leu Met Arg Phe Thr Thr Pro Gly Phe Pro Asp Ser Pro Tyr Pro Ala
225                 230                 235                 240

His Ala Arg Cys Gln Trp Ala Leu Arg Gly Asp Ala Asp Ser Val Leu
                245                 250                 255

Ser Leu Thr Phe Arg Ser Phe Asp Leu Ala Ser Cys Asp Glu Arg Gly
            260                 265                 270

Ser Asp Leu Val Thr Val Tyr Asn Thr Leu Ser Pro Met Glu Pro His
        275                 280                 285

Ala Leu Val Gln Leu Cys Gly Thr Tyr Pro Pro Ser Tyr Asn Leu Thr
290                 295                 300

Phe His Ser Ser Gln Asn Val Leu Leu Ile Thr Leu Ile Thr Asn Thr
305                 310                 315                 320

Glu Arg Arg His Pro Gly Phe Glu Ala Thr Phe Phe Gln Leu Pro Arg
                325                 330                 335

Met Ser Ser Cys Gly Gly Arg Leu Arg Lys Ala Gln Gly Thr Phe Asn
            340                 345                 350

Ser Pro Tyr Tyr Pro Gly His Tyr Pro Pro Asn Ile Asp Cys Thr Trp
        355                 360                 365

Asn Ile Glu Val Pro Asn Asn Gln His Val Lys Val Arg Phe Lys Phe
370                 375                 380

Phe Tyr Leu Leu Glu Pro Gly Val Pro Ala Gly Thr Cys Pro Lys Asp
385                 390                 395                 400

Tyr Val Glu Ile Asn Gly Glu Lys Tyr Cys Gly Glu Arg Ser Gln Phe
                405                 410                 415

Val Val Thr Ser Asn Ser Asn Lys Ile Thr Val Arg Phe His Ser Asp
            420                 425                 430

Gln Ser Tyr Thr Asp Thr Gly Phe Leu Ala Glu Tyr Leu Ser Tyr Asp
        435                 440                 445

Ser Ser Asp Pro Cys Pro Gly Gln Phe Thr Cys Arg Thr Gly Arg Cys
450                 455                 460

Ile Arg Lys Glu Leu Arg Cys Asp Gly Trp Ala Asp Cys Thr Asp His
465                 470                 475                 480
```

```
Ser Asp Glu Leu Asn Cys Ser Cys Asp Ala Gly His Gln Phe Thr Cys
            485                 490                 495

Lys Asn Lys Phe Cys Lys Pro Leu Phe Trp Val Cys Asp Ser Val Asn
            500                 505                 510

Asp Cys Gly Asp Asn Ser Asp Glu Gln Gly Cys Ser Cys Pro Ala Gln
            515                 520                 525

Thr Phe Arg Cys Ser Asn Gly Lys Cys Leu Ser Lys Ser Gln Gln Cys
        530                 535                 540

Asn Gly Lys Asp Asp Cys Gly Asp Gly Ser Asp Glu Ala Ser Cys Pro
545                 550                 555                 560

Lys Val Asn Val Val Thr Cys Thr Lys His Thr Tyr Arg Cys Leu Asn
            565                 570                 575

Gly Leu Cys Leu Ser Lys Gly Asn Pro Glu Cys Asp Gly Lys Glu Asp
            580                 585                 590

Cys Ser Asp Gly Ser Asp Glu Lys Asp Cys Asp Cys Gly Leu Arg Ser
            595                 600                 605

Phe Thr Arg Gln Ala Arg Val Val Gly Gly Thr Asp Ala Asp Glu Gly
        610                 615                 620

Glu Trp Pro Trp Gln Val Ser Leu His Ala Leu Gly Gln Gly His Ile
625                 630                 635                 640

Cys Gly Ala Ser Leu Ile Ser Pro Asn Trp Leu Val Ser Ala Ala His
            645                 650                 655

Cys Tyr Ile Asp Asp Arg Gly Phe Arg Tyr Ser Asp Pro Thr Gln Trp
            660                 665                 670

Thr Ala Phe Leu Gly Leu His Asp Gln Ser Gln Arg Ser Ala Pro Gly
        675                 680                 685

Val Gln Glu Arg Arg Leu Lys Arg Ile Ile Ser His Pro Phe Phe Asn
        690                 695                 700

Asp Phe Thr Phe Asp Tyr Asp Ile Ala Leu Leu Glu Leu Glu Lys Pro
705                 710                 715                 720

Ala Glu Tyr Ser Ser Met Val Arg Pro Ile Cys Leu Pro Asp Ala Ser
            725                 730                 735

His Val Phe Pro Ala Gly Lys Ala Ile Trp Val Thr Gly Trp Gly His
            740                 745                 750

Thr Gln Tyr Gly Gly Thr Gly Ala Leu Ile Leu Gln Lys Gly Glu Ile
        755                 760                 765

Arg Val Ile Asn Gln Thr Thr Cys Glu Asn Leu Leu Pro Gln Gln Ile
        770                 775                 780

Thr Pro Arg Met Met Cys Val Gly Phe Leu Ser Gly Gly Val Asp Ser
785                 790                 795                 800

Cys Gln Gly Asp Ser Gly Gly Pro Leu Ser Ser Val Glu Ala Asp Gly
            805                 810                 815

Arg Ile Phe Gln Ala Gly Val Val Ser Trp Gly Asp Gly Cys Ala Gln
            820                 825                 830

Arg Asn Lys Pro Gly Val Tyr Thr Arg Leu Pro Leu Phe Arg Asp Trp
            835                 840                 845

Ile Lys Glu Asn Thr Gly Val
        850                 855

<210> SEQ ID NO 3
<211> LENGTH: 241
<212> TYPE: PRT
<213> ORGANISM: Artificial
<220> FEATURE:
<223> OTHER INFORMATION: MT-SP1 fragment
```

<400> SEQUENCE: 3

```
Val Val Gly Gly Thr Asp Ala Asp Glu Gly Glu Trp Pro Trp Gln Val
1               5                   10                  15

Ser Leu His Ala Leu Gly Gln Gly His Ile Cys Gly Ala Ser Leu Ile
            20                  25                  30

Ser Pro Asn Trp Leu Val Ser Ala Ala His Cys Tyr Ile Asp Asp Arg
        35                  40                  45

Gly Phe Arg Tyr Ser Asp Pro Thr Gln Trp Thr Ala Phe Leu Gly Leu
    50                  55                  60

His Asp Gln Ser Gln Arg Ser Ala Pro Gly Val Gln Glu Arg Arg Leu
65                  70                  75                  80

Lys Arg Ile Ile Ser His Pro Phe Phe Asn Asp Phe Thr Phe Asp Tyr
                85                  90                  95

Asp Ile Ala Leu Leu Glu Leu Glu Lys Pro Ala Glu Tyr Ser Ser Met
                100                 105                 110

Val Arg Pro Ile Cys Leu Pro Asp Ala Ser His Val Phe Pro Ala Gly
            115                 120                 125

Lys Ala Ile Trp Val Thr Gly Trp Gly His Thr Gln Tyr Gly Gly Thr
130                 135                 140

Gly Ala Leu Ile Leu Gln Lys Gly Glu Ile Arg Val Ile Asn Gln Thr
145                 150                 155                 160

Thr Cys Glu Asn Leu Leu Pro Gln Gln Ile Thr Pro Arg Met Met Cys
                165                 170                 175

Val Gly Phe Leu Ser Gly Gly Val Asp Ser Cys Gln Gly Asp Ser Gly
            180                 185                 190

Gly Pro Leu Ser Ser Val Glu Ala Asp Gly Arg Ile Phe Gln Ala Gly
        195                 200                 205

Val Val Ser Trp Gly Asp Gly Cys Ala Gln Arg Asn Lys Pro Gly Val
    210                 215                 220

Tyr Thr Arg Leu Pro Leu Phe Arg Asp Trp Ile Lys Glu Asn Thr Gly
225                 230                 235                 240

Val
```

<210> SEQ ID NO 4
<211> LENGTH: 235
<212> TYPE: PRT
<213> ORGANISM: Artificial
<220> FEATURE:
<223> OTHER INFORMATION: Protein fragment/domain

<400> SEQUENCE: 4

```
Ile Val Gly Gly Gln Glu Ala Pro Arg Ser Lys Trp Pro Trp Gln Val
1               5                   10                  15

Ser Leu Arg Val His Asp Arg Tyr Trp Met His Phe Cys Gly Gly Ser
            20                  25                  30

Leu Ile His Pro Gln Trp Val Leu Thr Ala Ala His Cys Val Gly Pro
        35                  40                  45

Asp Val Lys Asp Leu Ala Ala Leu Arg Val Gln Leu Arg Glu Gln His
    50                  55                  60

Leu Tyr Tyr Gln Asp Gln Leu Leu Pro Val Ser Arg Ile Ile Val His
65                  70                  75                  80

Pro Gln Phe Tyr Thr Ala Gln Ile Gly Ala Asp Ile Ala Leu Leu Glu
                85                  90                  95

Leu Glu Glu Pro Val Lys Val Ser Ser His Val His Thr Val Thr Leu
```

```
            100                 105                 110
Pro Pro Ala Ser Glu Thr Phe Pro Pro Gly Met Pro Cys Trp Val Thr
            115                 120                 125

Gly Trp Gly Asp Val Asp Asn Asp Glu Arg Leu Pro Pro Phe Pro
130                 135                 140

Leu Lys Gln Val Lys Val Pro Ile Met Glu Asn His Ile Cys Asp Ala
145                 150                 155                 160

Lys Tyr His Leu Gly Ala Tyr Thr Gly Asp Val Arg Ile Val Arg
                165                 170                 175

Asp Asp Met Leu Cys Ala Gly Asn Thr Arg Arg Asp Ser Cys Gln Gly
            180                 185                 190

Asp Ser Gly Gly Pro Leu Val Cys Lys Val Asn Gly Thr Trp Leu Gln
            195                 200                 205

Ala Gly Val Val Ser Trp Gly Glu Gly Cys Ala Gln Pro Asn Arg Pro
            210                 215                 220

Gly Ile Tyr Thr Arg Val Val Pro Lys Lys Pro
225                 230                 235

<210> SEQ ID NO 5
<211> LENGTH: 235
<212> TYPE: PRT
<213> ORGANISM: Artificial
<220> FEATURE:
<223> OTHER INFORMATION: Protein fragment/domain

<400> SEQUENCE: 5

Ile Val Gly Gly Ser Asn Ala Lys Glu Gly Ala Trp Pro Trp Val Val
1               5                   10                  15

Gly Leu Tyr Tyr Gly Gly Arg Leu Leu Cys Gly Ala Ser Leu Val Ser
            20                  25                  30

Ser Asp Trp Leu Val Ser Ala Ala His Cys Val Tyr Gly Arg Asn Leu
        35                  40                  45

Glu Pro Ser Lys Trp Thr Ala Ile Leu Gly Leu His Met Lys Ser Asn
    50                  55                  60

Leu Thr Ser Pro Gln Thr Val Pro Arg Leu Ile Asp Glu Ile Val Ile
65                  70                  75                  80

Asn Pro His Tyr Asn Arg Arg Lys Asp Asn Asp Ile Ala Met Met
                85                  90                  95

His Leu Glu Phe Lys Val Asn Tyr Thr Asp Tyr Ile Gln Pro Ile Cys
            100                 105                 110

Leu Pro Glu Glu Asn Gln Val Phe Pro Pro Gly Arg Asn Cys Ser Ile
            115                 120                 125

Ala Gly Trp Gly Thr Val Val Tyr Gln Gly Thr Thr Ala Asn Ile Leu
            130                 135                 140

Gln Glu Ala Asp Val Pro Leu Leu Ser Asn Glu Arg Cys Gln Gln
145                 150                 155                 160

Met Pro Glu Tyr Asn Ile Thr Glu Asn Met Ile Cys Ala Gly Tyr Glu
                165                 170                 175

Glu Gly Gly Ile Asp Ser Cys Gln Gly Asp Ser Gly Gly Pro Leu Met
            180                 185                 190

Cys Gln Glu Asn Asn Arg Trp Phe Leu Ala Gly Val Thr Ser Phe Gly
            195                 200                 205

Tyr Lys Cys Ala Leu Pro Asn Arg Pro Gly Val Tyr Ala Arg Val Ser
            210                 215                 220

Arg Phe Thr Glu Trp Ile Gln Ser Phe Leu His
```

<210> SEQ ID NO 6
<211> LENGTH: 255
<212> TYPE: PRT
<213> ORGANISM: Artificial
<220> FEATURE:
<223> OTHER INFORMATION: Protein fragment/domain

<400> SEQUENCE: 6

```
Ile Val Gly Gly Arg Asp Thr Ser Leu Gly Arg Trp Pro Trp Gln Val
1               5                   10                  15
Ser Leu Arg Tyr Asp Gly Ala His Leu Cys Gly Gly Ser Leu Leu Ser
            20                  25                  30
Gly Asp Trp Val Leu Thr Ala Ala His Cys Phe Pro Glu Arg Asn Arg
        35                  40                  45
Val Leu Ser Arg Trp Arg Val Phe Ala Gly Ala Val Ala Gln Ala Ser
    50                  55                  60
Pro His Gly Leu Gln Leu Gly Val Gln Ala Val Val Tyr His Gly Gly
65                  70                  75                  80
Tyr Leu Pro Phe Arg Asp Pro Asn Ser Glu Glu Asn Ser Asn Asp Ile
                85                  90                  95
Ala Leu Val His Leu Ser Ser Pro Leu Pro Leu Thr Glu Tyr Ile Gln
            100                 105                 110
Pro Val Cys Leu Pro Ala Ala Gly Gln Ala Leu Val Asp Gly Lys Ile
        115                 120                 125
Cys Thr Val Thr Gly Trp Gly Asn Thr Gln Tyr Tyr Gly Gln Gln Ala
    130                 135                 140
Gly Val Leu Gln Glu Ala Arg Val Pro Ile Ile Ser Asn Asp Val Cys
145                 150                 155                 160
Asn Gly Ala Asp Phe Tyr Gly Asn Gln Ile Lys Pro Lys Met Phe Cys
                165                 170                 175
Ala Gly Tyr Pro Glu Gly Gly Ile Asp Ala Cys Gln Gly Asp Ser Gly
            180                 185                 190
Gly Pro Phe Val Cys Glu Asp Ser Ile Ser Arg Thr Pro Arg Trp Arg
        195                 200                 205
Leu Cys Gly Ile Val Ser Trp Gly Thr Gly Cys Ala Leu Ala Gln Lys
    210                 215                 220
Pro Gly Val Tyr Thr Lys Val Ser Asp Phe Arg Glu Trp Ile Phe Gln
225                 230                 235                 240
Ala Ile Lys Thr His Ser Glu Ala Ser Gly Met Val Thr Gln Leu
                245                 250                 255
```

<210> SEQ ID NO 7
<211> LENGTH: 224
<212> TYPE: PRT
<213> ORGANISM: Artificial
<220> FEATURE:
<223> OTHER INFORMATION: Protein fragment/domain

<400> SEQUENCE: 7

```
Ile Val Gly Gly Tyr Ile Cys Glu Glu Asn Ser Val Pro Tyr Gln Val
1               5                   10                  15
Ser Leu Asn Ser Gly Tyr His Phe Cys Gly Gly Ser Leu Ile Ser Glu
            20                  25                  30
Gln Trp Val Val Ser Ala Gly His Cys Tyr Lys Ser Arg Ile Gln Val
        35                  40                  45
```

-continued

Arg Leu Gly Glu His Asn Ile Glu Val Leu Glu Gly Asn Glu Gln Phe
         50                  55                  60

Ile Asn Ala Ala Lys Ile Arg His Pro Lys Tyr Asn Ser Arg Thr
 65              70                  75                  80

Leu Asp Asn Asp Ile Leu Leu Ile Lys Leu Ser Ser Pro Ala Val Ile
                 85                  90                  95

Asn Ser Arg Val Ser Ala Ile Ser Leu Pro Thr Ala Pro Ala Ala
            100                 105                 110

Gly Thr Glu Ser Leu Ile Ser Gly Trp Gly Asn Thr Leu Ser Ser Gly
            115                 120                 125

Ala Asp Tyr Pro Asp Glu Leu Gln Cys Leu Asp Ala Pro Val Leu Ser
        130                 135                 140

Gln Ala Glu Cys Glu Ala Ser Tyr Pro Gly Lys Ile Thr Asn Asn Met
145                 150                 155                 160

Phe Cys Val Gly Phe Leu Glu Gly Gly Lys Asp Ser Cys Gln Gly Asp
                165                 170                 175

Ser Gly Gly Pro Val Val Ser Asn Gly Glu Leu Gln Gly Ile Val Ser
            180                 185                 190

Trp Gly Tyr Gly Cys Ala Gln Lys Asn Arg Pro Gly Val Tyr Thr Lys
        195                 200                 205

Val Tyr Asn Tyr Val Asp Trp Ile Lys Asp Thr Ile Ala Ala Asn Ser
    210                 215                 220

<210> SEQ ID NO 8
<211> LENGTH: 230
<212> TYPE: PRT
<213> ORGANISM: Artificial
<220> FEATURE:
<223> OTHER INFORMATION: Protein fragment/domain

<400> SEQUENCE: 8

Ile Val Asn Gly Glu Asp Ala Val Pro Gly Ser Trp Pro Trp Gln Val
 1               5                  10                  15

Ser Leu Gln Asp Lys Thr Gly Phe His Phe Cys Gly Gly Ser Leu Ile
             20                  25                  30

Ser Glu Asp Trp Val Val Thr Ala Ala His Cys Gly Val Arg Thr Ser
         35                  40                  45

Asp Val Val Ala Gly Glu Phe Asp Gln Gly Ser Asp Glu Glu Asn
     50                  55                  60

Ile Gln Val Leu Lys Ile Ala Lys Val Phe Lys Asn Pro Lys Phe Ser
 65              70                  75                  80

Ile Leu Thr Val Asn Asn Asp Ile Thr Leu Leu Lys Leu Ala Thr Pro
                 85                  90                  95

Ala Arg Phe Ser Gln Thr Val Ser Ala Val Cys Leu Pro Ser Ala Asp
            100                 105                 110

Asp Asp Phe Pro Ala Gly Thr Leu Cys Ala Thr Thr Gly Trp Gly Lys
        115                 120                 125

Thr Lys Tyr Asn Ala Asn Lys Thr Pro Asp Lys Leu Gln Gln Ala Ala
    130                 135                 140

Leu Pro Leu Leu Ser Asn Ala Glu Cys Lys Lys Ser Trp Gly Arg Arg
145                 150                 155                 160

Ile Thr Asp Val Met Ile Cys Ala Gly Ala Ser Gly Val Ser Ser Cys
                165                 170                 175

Met Gly Asp Ser Gly Gly Pro Leu Val Cys Gln Lys Asp Gly Ala Trp
            180                 185                 190

Thr Leu Val Gly Ile Val Ser Trp Gly Ser Asp Thr Cys Ser Thr Ser
        195                 200                 205

Ser Pro Gly Val Tyr Ala Arg Val Thr Lys Leu Ile Pro Trp Val Gln
    210                 215                 220

Lys Ile Leu Ala Ala Asn
225                 230

<210> SEQ ID NO 9
<211> LENGTH: 274
<212> TYPE: PRT
<213> ORGANISM: Artificial
<220> FEATURE:
<223> OTHER INFORMATION: consensus sequence
<220> FEATURE:
<221> NAME/KEY: misc_feature
<222> LOCATION: (5)..(9)
<223> OTHER INFORMATION: X is any aa -- i.e. residue that is not highly
      conserved
<220> FEATURE:
<221> NAME/KEY: misc_feature
<222> LOCATION: (11)..(11)
<223> OTHER INFORMATION: X is any aa -- i.e. residue that is not highly
      conserved
<220> FEATURE:
<221> NAME/KEY: misc_feature
<222> LOCATION: (19)..(26)
<223> OTHER INFORMATION: X is any aa -- i.e. residue that is not highly
      conserved
<220> FEATURE:
<221> NAME/KEY: misc_feature
<222> LOCATION: (28)..(28)
<223> OTHER INFORMATION: X is any aa -- i.e. residue that is not highly
      conserved
<220> FEATURE:
<221> NAME/KEY: misc_feature
<222> LOCATION: (36)..(37)
<223> OTHER INFORMATION: X is any aa -- i.e. residue that is not highly
      conserved
<220> FEATURE:
<221> NAME/KEY: misc_feature
<222> LOCATION: (46)..(59)
<223> OTHER INFORMATION: X is any aa -- i.e. residue that is not highly
      conserved
<220> FEATURE:
<221> NAME/KEY: misc_feature
<222> LOCATION: (61)..(63)
<223> OTHER INFORMATION: X is any aa -- i.e. residue that is not highly
      conserved
<220> FEATURE:
<221> NAME/KEY: misc_feature
<222> LOCATION: (66)..(68)
<223> OTHER INFORMATION: X is any aa -- i.e. residue that is not highly
      conserved
<220> FEATURE:
<221> NAME/KEY: misc_feature
<222> LOCATION: (70)..(84)
<223> OTHER INFORMATION: X is any aa -- i.e. residue that is not highly
      conserved
<220> FEATURE:
<221> NAME/KEY: misc_feature
<222> LOCATION: (90)..(98)
<223> OTHER INFORMATION: X is any aa -- i.e. residue that is not highly
      conserved
<220> FEATURE:
<221> NAME/KEY: misc_feature
<222> LOCATION: (101)..(102)
<223> OTHER INFORMATION: X is any aa -- i.e. residue that is not highly
      conserved
<220> FEATURE:
<221> NAME/KEY: misc_feature
<222> LOCATION: (104)..(104)
<223> OTHER INFORMATION: X is any aa -- i.e. residue that is not highly
      conserved
<220> FEATURE:
<221> NAME/KEY: misc_feature
<222> LOCATION: (108)..(110)

-continued

```
<223> OTHER INFORMATION: X is any aa -- i.e. residue that is not highly
      conserved
<220> FEATURE:
<221> NAME/KEY: misc_feature
<222> LOCATION: (112)..(120)
<223> OTHER INFORMATION: X is any aa -- i.e. residue that is not highly
      conserved
<220> FEATURE:
<221> NAME/KEY: misc_feature
<222> LOCATION: (122)..(122)
<223> OTHER INFORMATION: X is any aa -- i.e. residue that is not highly
      conserved
<220> FEATURE:
<221> NAME/KEY: misc_feature
<222> LOCATION: (130)..(130)
<223> OTHER INFORMATION: X is any aa -- i.e. residue that is not highly
      conserved
<220> FEATURE:
<221> NAME/KEY: misc_feature
<222> LOCATION: (130)..(130)
<223> OTHER INFORMATION: X is any aa -- i.e. residue that is not highly
      conserved
<220> FEATURE:
<221> NAME/KEY: misc_feature
<222> LOCATION: (130)..(130)
<223> OTHER INFORMATION: X is any aa -- i.e. residue that is not highly
      conserved
<220> FEATURE:
<221> NAME/KEY: misc_feature
<222> LOCATION: (130)..(130)
<223> OTHER INFORMATION: X is any aa -- i.e. residue that is not highly
      conserved
<220> FEATURE:
<221> NAME/KEY: misc_feature
<222> LOCATION: (133)..(133)
<223> OTHER INFORMATION: X is any aa -- i.e. residue that is not highly
      conserved
<220> FEATURE:
<221> NAME/KEY: misc_feature
<222> LOCATION: (135)..(140)
<223> OTHER INFORMATION: X is any aa -- i.e. residue that is not highly
      conserved
<220> FEATURE:
<221> NAME/KEY: misc_feature
<222> LOCATION: (142)..(142)
<223> OTHER INFORMATION: X is any aa -- i.e. residue that is not highly
      conserved
<220> FEATURE:
<221> NAME/KEY: misc_feature
<222> LOCATION: (148)..(148)
<223> OTHER INFORMATION: X is any aa -- i.e. residue that is not highly
      conserved
<220> FEATURE:
<221> NAME/KEY: misc_feature
<222> LOCATION: (150)..(152)
<223> OTHER INFORMATION: X is any aa -- i.e. residue that is not highly
      conserved
<220> FEATURE:
<221> NAME/KEY: misc_feature
<222> LOCATION: (157)..(158)
<223> OTHER INFORMATION: X is any aa -- i.e. residue that is not highly
      conserved
<220> FEATURE:
<221> NAME/KEY: misc_feature
<222> LOCATION: (160)..(160)
<223> OTHER INFORMATION: X is any aa -- i.e. residue that is not highly
      conserved
<220> FEATURE:
<221> NAME/KEY: misc_feature
<222> LOCATION: (166)..(166)
<223> OTHER INFORMATION: X is any aa -- i.e. residue that is not highly
      conserved
<220> FEATURE:
<221> NAME/KEY: misc_feature
<222> LOCATION: (168)..(168)
<223> OTHER INFORMATION: X is any aa -- i.e. residue that is not highly
      conserved
<220> FEATURE:
<221> NAME/KEY: misc_feature
```

```
<222> LOCATION: (170)..(171)
<223> OTHER INFORMATION: X is any aa -- i.e. residue that is not highly
      conserved
<220> FEATURE:
<221> NAME/KEY: misc_feature
<222> LOCATION: (173)..(175)
<223> OTHER INFORMATION: X is any aa -- i.e. residue that is not highly
      conserved
<220> FEATURE:
<221> NAME/KEY: misc_feature
<222> LOCATION: (177)..(178)
<223> OTHER INFORMATION: X is any aa -- i.e. residue that is not highly
      conserved
<220> FEATURE:
<221> NAME/KEY: misc_feature
<222> LOCATION: (181)..(184)
<223> OTHER INFORMATION: X is any aa -- i.e. residue that is not highly
      conserved
<220> FEATURE:
<221> NAME/KEY: misc_feature
<222> LOCATION: (186)..(186)
<223> OTHER INFORMATION: X is any aa -- i.e. residue that is not highly
      conserved
<220> FEATURE:
<221> NAME/KEY: misc_feature
<222> LOCATION: (190)..(191)
<223> OTHER INFORMATION: X is any aa -- i.e. residue that is not highly
      conserved
<220> FEATURE:
<221> NAME/KEY: misc_feature
<222> LOCATION: (193)..(200)
<223> OTHER INFORMATION: X is any aa -- i.e. residue that is not highly
      conserved
<220> FEATURE:
<221> NAME/KEY: misc_feature
<222> LOCATION: (203)..(203)
<223> OTHER INFORMATION: X is any aa -- i.e. residue that is not highly
      conserved
<220> FEATURE:
<221> NAME/KEY: misc_feature
<222> LOCATION: (216)..(229)
<223> OTHER INFORMATION: X is any aa -- i.e. residue that is not highly
      conserved
<220> FEATURE:
<221> NAME/KEY: misc_feature
<222> LOCATION: (236)..(236)
<223> OTHER INFORMATION: X is any aa -- i.e. residue that is not highly
      conserved
<220> FEATURE:
<221> NAME/KEY: misc_feature
<222> LOCATION: (241)..(241)
<223> OTHER INFORMATION: X is any aa -- i.e. residue that is not highly
      conserved
<220> FEATURE:
<221> NAME/KEY: misc_feature
<222> LOCATION: (251)..(252)
<223> OTHER INFORMATION: X is any aa -- i.e. residue that is not highly
      conserved
<220> FEATURE:
<221> NAME/KEY: misc_feature
<222> LOCATION: (254)..(254)
<223> OTHER INFORMATION: X is any aa -- i.e. residue that is not highly
      conserved
<220> FEATURE:
<221> NAME/KEY: misc_feature
<222> LOCATION: (258)..(274)
<223> OTHER INFORMATION: X is any aa -- i.e. residue that is not highly
      conserved

<400> SEQUENCE: 9

Ile Val Gly Gly Xaa Xaa Xaa Xaa Xaa Gly Xaa Trp Pro Trp Gln Val
1               5                   10                  15

Ser Leu Xaa Xaa Xaa Xaa Xaa Xaa Xaa His Xaa Cys Gly Gly Ser
            20                  25                  30

Leu Ile Ser Xaa Xaa Trp Val Val Ser Ala Ala His Cys Xaa Xaa Xaa
        35                  40                  45
```

```
Xaa Xaa Xaa Xaa Xaa Xaa Xaa Xaa Xaa Xaa Trp Xaa Xaa Xaa Leu
        50                  55                  60

Gly Xaa Xaa Xaa Gln Xaa Xaa Xaa Xaa Xaa Xaa Xaa Xaa Xaa Xaa
65                  70                  75                  80

Xaa Xaa Xaa Xaa Ile Ile Xaa His Pro Xaa Xaa Xaa Xaa Xaa Xaa
                85                  90                  95

Xaa Xaa Ile Thr Xaa Xaa Met Xaa Cys Ala Gly Xaa Xaa Xaa Tyr Xaa
            100                 105                 110

Xaa Xaa Xaa Xaa Xaa Xaa Xaa Thr Xaa Asp Asn Asp Ile Ala Leu
                115                 120                 125

Leu Xaa Leu Glu Xaa Pro Xaa Xaa Xaa Xaa Xaa Val Xaa Pro Ile
    130                 135                 140

Cys Leu Pro Xaa Ala Xaa Xaa Phe Pro Ala Gly Xaa Xaa Cys Xaa
145             150             155                 160

Val Thr Gly Trp Gly Xaa Thr Xaa Tyr Xaa Xaa Gly Xaa Xaa Xaa Ala
                165                 170                 175

Xaa Xaa Leu Gln Xaa Xaa Xaa Xaa Pro Xaa Ile Ser Asn Xaa Xaa Cys
            180                 185                 190

Xaa Xaa Xaa Xaa Xaa Xaa Xaa Gly Gly Xaa Asp Ser Cys Gln Gly
            195                 200             205

Asp Ser Gly Gly Pro Leu Val Xaa Xaa Xaa Xaa Xaa Xaa Xaa Xaa
    210                 215                 220

Xaa Xaa Xaa Xaa Xaa Gly Val Val Ser Trp Gly Xaa Gly Cys Ala Gln
225                 230                 235                 240

Xaa Asn Arg Pro Gly Val Tyr Thr Arg Val Xaa Xaa Phe Xaa Asp Trp
                245                 250                 255

Ile Xaa Xaa Xaa Xaa Xaa Xaa Xaa Xaa Xaa Xaa Xaa Xaa Xaa Xaa
            260                 265                 270

Xaa Xaa

<210> SEQ ID NO 10
<211> LENGTH: 35
<212> TYPE: PRT
<213> ORGANISM: Artificial
<220> FEATURE:
<223> OTHER INFORMATION: Protein fragment/domain

<400> SEQUENCE: 10

Cys Pro Gly Gln Phe Thr Cys Arg Thr Gly Arg Cys Ile Arg Lys Glu
1               5                   10                  15

Leu Arg Cys Asp Gly Trp Ala Asp Cys Thr Asp His Ser Asp Glu Leu
            20                  25                  30

Asn Cys Ser
        35

<210> SEQ ID NO 11
<211> LENGTH: 37
<212> TYPE: PRT
<213> ORGANISM: Artificial
<220> FEATURE:
<223> OTHER INFORMATION: Protein fragment/domain

<400> SEQUENCE: 11

Cys Asp Ala Gly His Gln Phe Thr Cys Lys Asn Lys Phe Cys Lys Pro
1               5                   10                  15

Leu Phe Trp Val Cys Asp Ser Val Asn Asp Cys Gly Asp Asn Ser Asp
            20                  25                  30
```

```
Glu Gln Gly Cys Ser
        35
```

<210> SEQ ID NO 12
<211> LENGTH: 42
<212> TYPE: PRT
<213> ORGANISM: Artificial
<220> FEATURE:
<223> OTHER INFORMATION: Protein fragment/domain

<400> SEQUENCE: 12

```
Cys Pro Ala Gln Thr Phe Arg Cys Ser Asn Gly Lys Cys Leu Ser Lys
1               5                   10                  15

Ser Gln Gln Cys Asn Gly Lys Asp Asp Cys Gly Asp Gly Ser Asp Glu
            20                  25                  30

Ala Ser Cys Pro Lys Val Asn Val Val Thr
        35                  40
```

<210> SEQ ID NO 13
<211> LENGTH: 37
<212> TYPE: PRT
<213> ORGANISM: Artificial
<220> FEATURE:
<223> OTHER INFORMATION: Protein fragment/domain

<400> SEQUENCE: 13

```
Cys Thr Lys His Thr Tyr Arg Cys Leu Asn Gly Leu Cys Leu Ser Lys
1               5                   10                  15

Gly Asn Pro Glu Cys Asp Gly Lys Glu Asp Cys Ser Asp Gly Ser Asp
            20                  25                  30

Glu Lys Asp Cys Asp
        35
```

<210> SEQ ID NO 14
<211> LENGTH: 41
<212> TYPE: PRT
<213> ORGANISM: Artificial
<220> FEATURE:
<223> OTHER INFORMATION: Protein fragment/domain

<400> SEQUENCE: 14

```
Cys Glu Arg Asn Glu Phe Gln Cys Gln Asp Gly Lys Cys Ile Ser Tyr
1               5                   10                  15

Lys Trp Val Cys Asp Gly Ser Ala Glu Cys Gln Asp Gly Ser Asp Glu
            20                  25                  30

Ser Gln Glu Thr Cys Leu Ser Val Thr
        35                  40
```

<210> SEQ ID NO 15
<211> LENGTH: 41
<212> TYPE: PRT
<213> ORGANISM: Artificial
<220> FEATURE:
<223> OTHER INFORMATION: Protein fragment/domain

<400> SEQUENCE: 15

```
Cys Lys Ser Gly Asp Phe Ser Cys Gly Gly Arg Val Asn Arg Cys Ile
1               5                   10                  15

Pro Gln Phe Trp Arg Cys Asp Gly Gln Val Asp Cys Asp Asn Gly Ser
            20                  25                  30

Asp Glu Gln Gly Cys Pro Pro Lys Thr
        35                  40
```

```
<210> SEQ ID NO 16
<211> LENGTH: 38
<212> TYPE: PRT
<213> ORGANISM: Artificial
<220> FEATURE:
<223> OTHER INFORMATION: Protein fragment/domain

<400> SEQUENCE: 16

Cys Ser Gln Asp Glu Phe Arg Cys His Asp Gly Lys Cys Ile Ser Arg
1               5                   10                  15

Gln Phe Val Cys Asp Ser Arg Asp Cys Leu Asp Gly Ser Asp Glu Ala
            20                  25                  30

Ser Cys Pro Val Leu Thr
        35

<210> SEQ ID NO 17
<211> LENGTH: 49
<212> TYPE: PRT
<213> ORGANISM: Artificial
<220> FEATURE:
<223> OTHER INFORMATION: Protein fragment/domain

<400> SEQUENCE: 17

Cys Gly Pro Ala Ser Phe Gln Cys Asn Ser Ser Thr Cys Ile Pro Gln
1               5                   10                  15

Leu Trp Ala Cys Asp Asn Asp Pro Asp Cys Glu Asp Gly Ser Asp Glu
            20                  25                  30

Trp Pro Gln Arg Cys Arg Gly Leu Tyr Val Phe Gln Gly Asp Ser Ser
        35                  40                  45

Pro

<210> SEQ ID NO 18
<211> LENGTH: 39
<212> TYPE: PRT
<213> ORGANISM: Artificial
<220> FEATURE:
<223> OTHER INFORMATION: Protein fragment/domain

<400> SEQUENCE: 18

Cys Ser Ala Phe Glu Phe His Cys Leu Ser Gly Glu Cys Ile His Ser
1               5                   10                  15

Ser Trp Arg Cys Asp Gly Gly Pro Asp Cys Lys Asp Lys Ser Asp Glu
            20                  25                  30

Glu Asn Cys Ala Val Ala Thr
        35

<210> SEQ ID NO 19
<211> LENGTH: 40
<212> TYPE: PRT
<213> ORGANISM: Artificial
<220> FEATURE:
<223> OTHER INFORMATION: Protein fragment/domain

<400> SEQUENCE: 19

Cys Arg Pro Asp Glu Phe Gln Cys Ser Asp Gly Asn Cys Ile His Gly
1               5                   10                  15

Ser Arg Gln Cys Asp Arg Glu Tyr Asp Cys Lys Asp Met Ser Asp Glu
            20                  25                  30

Val Gly Cys Val Asn Val Thr Leu
        35                  40
```

<210> SEQ ID NO 20
<211> LENGTH: 42
<212> TYPE: PRT
<213> ORGANISM: Artificial
<220> FEATURE:
<223> OTHER INFORMATION: Protein fragment/domain

<400> SEQUENCE: 20

Cys Glu Gly Pro Asn Lys Phe Lys Cys His Ser Gly Glu Cys Ile Thr
1               5                   10                  15

Leu Asp Lys Val Cys Asn Met Ala Arg Asp Cys Arg Asp Trp Ser Asp
            20                  25                  30

Glu Pro Ile Lys Glu Cys Gly Thr Asn Glu
        35                  40

<210> SEQ ID NO 21
<211> LENGTH: 53
<212> TYPE: PRT
<213> ORGANISM: Artificial
<220> FEATURE:
<223> OTHER INFORMATION: consensus sequence
<220> FEATURE:
<221> NAME/KEY: misc_feature
<222> LOCATION: (2)..(8)
<223> OTHER INFORMATION: X is any aa -- i.e. residue that is not highly
      conserved
<220> FEATURE:
<221> NAME/KEY: misc_feature
<222> LOCATION: (10)..(13)
<223> OTHER INFORMATION: X is any aa -- i.e. residue that is not highly
      conserved
<220> FEATURE:
<221> NAME/KEY: misc_feature
<222> LOCATION: (15)..(15)
<223> OTHER INFORMATION: X is any aa -- i.e. residue that is not highly
      conserved
<220> FEATURE:
<221> NAME/KEY: misc_feature
<222> LOCATION: (18)..(21)
<223> OTHER INFORMATION: X is any aa -- i.e. residue that is not highly
      conserved
<220> FEATURE:
<221> NAME/KEY: misc_feature
<222> LOCATION: (23)..(23)
<223> OTHER INFORMATION: X is any aa -- i.e. residue that is not highly
      conserved
<220> FEATURE:
<221> NAME/KEY: misc_feature
<222> LOCATION: (27)..(28)
<223> OTHER INFORMATION: X is any aa -- i.e. residue that is not highly
      conserved
<220> FEATURE:
<221> NAME/KEY: misc_feature
<222> LOCATION: (31)..(31)
<223> OTHER INFORMATION: X is any aa -- i.e. residue that is not highly
      conserved
<220> FEATURE:
<221> NAME/KEY: misc_feature
<222> LOCATION: (37)..(40)
<223> OTHER INFORMATION: X is any aa -- i.e. residue that is not highly
      conserved
<220> FEATURE:
<221> NAME/KEY: misc_feature
<222> LOCATION: (42)..(53)
<223> OTHER INFORMATION: X is any aa -- i.e. residue that is not highly
      conserved

<400> SEQUENCE: 21

Cys Xaa Xaa Xaa Xaa Xaa Xaa Xaa Cys Xaa Xaa Xaa Xaa Gly Xaa Cys
1               5                   10                  15

Ile Xaa Xaa Xaa Xaa Trp Xaa Cys Asp Gly Xaa Xaa Asp Cys Xaa Asp
            20                  25                  30

```
Gly Ser Asp Glu Xaa Xaa Xaa Cys Xaa Xaa Xaa Xaa Xaa Xaa
        35              40                  45

Xaa Xaa Xaa Xaa Xaa
    50
```

<210> SEQ ID NO 22
<211> LENGTH: 126
<212> TYPE: PRT
<213> ORGANISM: Artificial
<220> FEATURE:
<223> OTHER INFORMATION: Protein fragment/domain

<400> SEQUENCE: 22

```
Cys Ser Phe Gly Leu His Ala Arg Gly Val Glu Leu Met Arg Phe Thr
1               5                   10                  15

Thr Pro Gly Phe Pro Asp Ser Pro Tyr Pro Ala His Ala Arg Cys Gln
            20                  25                  30

Trp Ala Leu Arg Gly Asp Ala Asp Ser Val Leu Ser Leu Thr Phe Arg
        35                  40                  45

Ser Phe Asp Leu Ala Ser Cys Asp Glu Arg Gly Ser Asp Leu Val Thr
    50                  55                  60

Val Tyr Asn Thr Leu Ser Pro Met Glu Pro His Ala Leu Val Gln Leu
65                  70                  75                  80

Cys Gly Thr Tyr Pro Pro Ser Tyr Asn Leu Thr Phe His Ser Ser Gln
                85                  90                  95

Asn Val Leu Leu Ile Thr Leu Ile Thr Asn Thr Glu Arg Arg His Pro
            100                 105                 110

Gly Phe Glu Ala Thr Phe Phe Gln Leu Pro Arg Met Ser Ser
        115                 120                 125
```

<210> SEQ ID NO 23
<211> LENGTH: 113
<212> TYPE: PRT
<213> ORGANISM: Artificial
<220> FEATURE:
<223> OTHER INFORMATION: Protein fragment/domain

<400> SEQUENCE: 23

```
Cys Gly Gly Arg Leu Arg Lys Ala Gln Gly Thr Phe Asn Ser Pro Tyr
1               5                   10                  15

Tyr Pro Gly His Tyr Pro Pro Asn Ile Asp Cys Thr Trp Asn Ile Glu
            20                  25                  30

Val Pro Asn Asn Gln His Val Lys Val Arg Phe Lys Phe Phe Tyr Leu
        35                  40                  45

Leu Glu Pro Gly Val Pro Ala Gly Thr Cys Pro Lys Asp Tyr Val Glu
    50                  55                  60

Ile Asn Gly Glu Lys Tyr Cys Gly Glu Arg Ser Gln Phe Val Val Thr
65                  70                  75                  80

Ser Asn Ser Asn Lys Ile Thr Val Arg Phe His Ser Asp Gln Ser Tyr
                85                  90                  95

Thr Asp Thr Gly Phe Leu Ala Glu Tyr Leu Ser Tyr Asp Ser Ser Asp
            100                 105                 110

Pro
```

<210> SEQ ID NO 24
<211> LENGTH: 110
<212> TYPE: PRT
<213> ORGANISM: Artificial

```
<220> FEATURE:
<223> OTHER INFORMATION: Protein fragment/domain

<400> SEQUENCE: 24

Cys Asp Gly Arg Phe Leu Leu Thr Gly Ser Ser Gly Ser Phe Gln Ala
1               5                   10                  15

Thr His Tyr Pro Lys Pro Ser Glu Thr Ser Val Val Cys Gln Trp Ile
            20                  25                  30

Ile Arg Val Asn Gln Gly Leu Ser Ile Lys Leu Ser Phe Asp Asp Phe
        35                  40                  45

Asn Thr Tyr Tyr Thr Asp Ile Leu Asp Ile Tyr Glu Gly Val Gly Ser
    50                  55                  60

Ser Lys Ile Leu Arg Ala Ser Ile Trp Glu Thr Asn Pro Gly Thr Ile
65                  70                  75                  80

Arg Ile Phe Ser Asn Gln Val Thr Ala Thr Phe Leu Ile Glu Ser Asp
                85                  90                  95

Glu Ser Asp Tyr Val Gly Phe Asn Ala Thr Tyr Thr Ala Phe
            100                 105                 110

<210> SEQ ID NO 25
<211> LENGTH: 111
<212> TYPE: PRT
<213> ORGANISM: Artificial
<220> FEATURE:
<223> OTHER INFORMATION: Protein fragment/domain

<400> SEQUENCE: 25

Cys Gly Gly Pro Phe Glu Leu Trp Glu Pro Asn Thr Thr Phe Ser Ser
1               5                   10                  15

Thr Asn Phe Pro Asn Ser Tyr Pro Asn Leu Ala Phe Cys Val Trp Ile
            20                  25                  30

Leu Asn Ala Gln Lys Gly Lys Asn Ile Gln Leu His Phe Gln Glu Phe
        35                  40                  45

Asp Leu Glu Asn Ile Asn Asp Val Val Glu Ile Arg Asp Gly Glu Glu
    50                  55                  60

Ala Asp Ser Leu Leu Leu Ala Val Tyr Thr Gly Pro Gly Pro Val Lys
65                  70                  75                  80

Asp Val Phe Ser Thr Thr Asn Arg Met Thr Val Leu Leu Ile Thr Asn
                85                  90                  95

Asp Val Leu Ala Arg Gly Gly Phe Lys Ala Asn Phe Thr Thr Gly
            100                 105                 110

<210> SEQ ID NO 26
<211> LENGTH: 113
<212> TYPE: PRT
<213> ORGANISM: Artificial
<220> FEATURE:
<223> OTHER INFORMATION: Protein fragment/domain

<400> SEQUENCE: 26

Cys Gly Glu Thr Leu Gln Asp Ser Thr Gly Asn Phe Ser Ser Pro Glu
1               5                   10                  15

Tyr Pro Asn Gly Tyr Ser Ala His Met His Cys Val Trp Arg Ile Ser
            20                  25                  30

Val Thr Pro Gly Glu Lys Ile Ile Leu Asn Phe Thr Ser Leu Asp Leu
        35                  40                  45

Tyr Arg Ser Arg Leu Cys Trp Tyr Asp Tyr Val Glu Val Arg Asp Gly
    50                  55                  60
```

```
Phe Trp Arg Lys Ala Pro Leu Arg Gly Arg Phe Cys Gly Ser Lys Leu
 65                  70                  75                  80

Pro Glu Pro Ile Val Ser Thr Asp Ser Arg Leu Trp Val Glu Phe Arg
                 85                  90                  95

Ser Ser Ser Asn Trp Val Gly Lys Gly Phe Phe Ala Val Tyr Glu Ala
                100                 105                 110

Ile

<210> SEQ ID NO 27
<211> LENGTH: 112
<212> TYPE: PRT
<213> ORGANISM: Artificial
<220> FEATURE:
<223> OTHER INFORMATION: Protein fragment/domain

<400> SEQUENCE: 27

Cys Gly Gly Asp Val Lys Lys Asp Tyr Gly His Ile Gln Ser Pro Asn
 1               5                  10                  15

Tyr Pro Asp Asp Tyr Arg Pro Ser Lys Val Cys Ile Trp Arg Ile Gln
                 20                  25                  30

Val Ser Glu Gly Phe His Val Gly Leu Thr Phe Gln Ser Phe Glu Ile
             35                  40                  45

Glu Arg His Asp Ser Cys Ala Tyr Asp Tyr Leu Glu Val Arg Asp Gly
         50                  55                  60

His Ser Glu Ser Ser Thr Leu Ile Gly Arg Tyr Cys Gly Tyr Glu Lys
 65                  70                  75                  80

Pro Asp Asp Ile Lys Ser Thr Ser Ser Arg Leu Trp Leu Lys Phe Val
                 85                  90                  95

Ser Asp Gly Ser Ile Asn Lys Ala Gly Phe Ala Val Asn Phe Phe Lys
                100                 105                 110

<210> SEQ ID NO 28
<211> LENGTH: 113
<212> TYPE: PRT
<213> ORGANISM: Artificial
<220> FEATURE:
<223> OTHER INFORMATION: Protein fragment/domain

<400> SEQUENCE: 28

Cys Gly Gly Phe Leu Thr Lys Leu Asn Gly Ser Ile Thr Ser Pro Gly
 1               5                  10                  15

Trp Pro Lys Glu Tyr Pro Pro Asn Lys Asn Cys Ile Trp Gln Leu Val
                 20                  25                  30

Ala Pro Thr Gln Tyr Arg Ile Ser Leu Gln Phe Asp Phe Phe Glu Thr
             35                  40                  45

Glu Gly Asn Asp Val Cys Lys Tyr Asp Phe Val Glu Val Arg Ser Gly
         50                  55                  60

Leu Thr Ala Asp Ser Lys Leu His Gly Lys Phe Cys Gly Ser Glu Lys
 65                  70                  75                  80

Pro Glu Val Ile Thr Ser Gln Tyr Asn Asn Met Arg Val Glu Phe Lys
                 85                  90                  95

Ser Asp Asn Thr Val Ser Lys Lys Gly Phe Lys Ala His Phe Phe Ser
                100                 105                 110

Glu

<210> SEQ ID NO 29
<211> LENGTH: 123
<212> TYPE: PRT
```

```
<213> ORGANISM: Artificial
<220> FEATURE:
<223> OTHER INFORMATION: Protein fragment/domain

<400> SEQUENCE: 29

Ser Ile Pro Ile Pro Gln Lys Leu Phe Gly Glu Val Thr Ser Pro Leu
1               5                   10                  15

Phe Pro Lys Pro Tyr Pro Asn Asn Phe Glu Thr Thr Thr Val Ile Thr
            20                  25                  30

Val Pro Thr Gly Tyr Arg Val Lys Leu Val Phe Gln Gln Phe Asp Leu
        35                  40                  45

Glu Pro Ser Glu Gly Cys Phe Tyr Asp Tyr Val Lys Ile Ser Ala Asp
    50                  55                  60

Lys Lys Leu Gly Arg Phe Cys Gly Gln Leu Gly Ser Pro Leu Gly Asn
65                  70                  75                  80

Pro Pro Gly Lys Lys Glu Phe Met Ser Gln Gly Asn Lys Met Leu Leu
                85                  90                  95

Thr Phe His Thr Asp Phe Ser Asn Glu Glu Asn Gly Thr Ile Met Phe
            100                 105                 110

Tyr Lys Gly Phe Leu Ala Tyr Tyr Gln Ala Val
            115                 120

<210> SEQ ID NO 30
<211> LENGTH: 112
<212> TYPE: PRT
<213> ORGANISM: Artificial
<220> FEATURE:
<223> OTHER INFORMATION: Protein fragment/domain

<400> SEQUENCE: 30

Cys Ser Ser Glu Tyr Thr Glu Ala Ser Gly Tyr Ile Ser Ser Leu Glu
1               5                   10                  15

Tyr Pro Arg Ser Tyr Pro Pro Asp Leu Arg Cys Asn Tyr Ser Ile Arg
            20                  25                  30

Val Glu Arg Gly Leu Thr Leu His Leu Lys Phe Leu Glu Pro Phe Asp
        35                  40                  45

Ile Asp Asp His Gln Gln Val His Cys Pro Tyr Asp Gln Leu Gln Ile
    50                  55                  60

Tyr Ala Asn Gly Lys Asn Ile Gly Glu Phe Cys Gly Lys Gln Arg Pro
65                  70                  75                  80

Pro Asp Leu Asp Thr Ser Ser Asn Ala Val Asp Leu Leu Phe Phe Thr
                85                  90                  95

Asp Glu Ser Gly Asp Ser Arg Gly Trp Lys Leu Arg Tyr Thr Thr Glu
            100                 105                 110

<210> SEQ ID NO 31
<211> LENGTH: 143
<212> TYPE: PRT
<213> ORGANISM: Artificial
<220> FEATURE:
<223> OTHER INFORMATION: consensus sequence
<220> FEATURE:
<221> NAME/KEY: misc_feature
<222> LOCATION: (6)..(12)
<223> OTHER INFORMATION: X is any aa -- i.e. residue that is not highly
      conserved
<220> FEATURE:
<221> NAME/KEY: misc_feature
<222> LOCATION: (15)..(15)
<223> OTHER INFORMATION: X is any aa -- i.e. residue that is not highly
      conserved
<220> FEATURE:
```

```
<221> NAME/KEY: misc_feature
<222> LOCATION: (19)..(19)
<223> OTHER INFORMATION: X is any aa -- i.e. residue that is not highly
      conserved
<220> FEATURE:
<221> NAME/KEY: misc_feature
<222> LOCATION: (22)..(23)
<223> OTHER INFORMATION: X is any aa -- i.e. residue that is not highly
      conserved
<220> FEATURE:
<221> NAME/KEY: misc_feature
<222> LOCATION: (27)..(30)
<223> OTHER INFORMATION: X is any aa -- i.e. residue that is not highly
      conserved
<220> FEATURE:
<221> NAME/KEY: misc_feature
<222> LOCATION: (32)..(32)
<223> OTHER INFORMATION: X is any aa -- i.e. residue that is not highly
      conserved
<220> FEATURE:
<221> NAME/KEY: misc_feature
<222> LOCATION: (36)..(36)
<223> OTHER INFORMATION: X is any aa -- i.e. residue that is not highly
      conserved
<220> FEATURE:
<221> NAME/KEY: misc_feature
<222> LOCATION: (37)..(38)
<223> OTHER INFORMATION: X is any aa -- i.e. residue that is not highly
      conserved
<220> FEATURE:
<221> NAME/KEY: misc_feature
<222> LOCATION: (41)..(42)
<223> OTHER INFORMATION: X is any aa -- i.e. residue that is not highly
      conserved
<220> FEATURE:
<221> NAME/KEY: misc_feature
<222> LOCATION: (44)..(44)
<223> OTHER INFORMATION: X is any aa -- i.e. residue that is not highly
      conserved
<220> FEATURE:
<221> NAME/KEY: misc_feature
<222> LOCATION: (46)..(46)
<223> OTHER INFORMATION: X is any aa -- i.e. residue that is not highly
      conserved
<220> FEATURE:
<221> NAME/KEY: misc_feature
<222> LOCATION: (47)..(49)
<223> OTHER INFORMATION: X is any aa -- i.e. residue that is not highly
      conserved
<220> FEATURE:
<221> NAME/KEY: misc_feature
<222> LOCATION: (54)..(62)
<223> OTHER INFORMATION: X is any aa -- i.e. residue that is not highly
      conserved
<220> FEATURE:
<221> NAME/KEY: misc_feature
<222> LOCATION: (66)..(68)
<223> OTHER INFORMATION: X is any aa -- i.e. residue that is not highly
      conserved
<220> FEATURE:
<221> NAME/KEY: misc_feature
<222> LOCATION: (75)..(76)
<223> OTHER INFORMATION: X is any aa -- i.e. residue that is not highly
      conserved
<220> FEATURE:
<221> NAME/KEY: misc_feature
<222> LOCATION: (78)..(85)
<223> OTHER INFORMATION: X is any aa -- i.e. residue that is not highly
      conserved
<220> FEATURE:
<221> NAME/KEY: misc_feature
<222> LOCATION: (87)..(88)
<223> OTHER INFORMATION: X is any aa -- i.e. residue that is not highly
      conserved
<220> FEATURE:
<221> NAME/KEY: misc_feature
<222> LOCATION: (91)..(93)
<223> OTHER INFORMATION: X is any aa -- i.e. residue that is not highly
      conserved
```

```
<220> FEATURE:
<221> NAME/KEY: misc_feature
<222> LOCATION: (95)..(96)
<223> OTHER INFORMATION: X is any aa -- i.e. residue that is not highly
      conserved
<220> FEATURE:
<221> NAME/KEY: misc_feature
<222> LOCATION: (98)..(107)
<223> OTHER INFORMATION: X is any aa -- i.e. residue that is not highly
      conserved
<220> FEATURE:
<221> NAME/KEY: misc_feature
<222> LOCATION: (112)..(113)
<223> OTHER INFORMATION: X is any aa -- i.e. residue that is not highly
      conserved
<220> FEATURE:
<221> NAME/KEY: misc_feature
<222> LOCATION: (115)..(115)
<223> OTHER INFORMATION: X is any aa -- i.e. residue that is not highly
      conserved
<220> FEATURE:
<221> NAME/KEY: misc_feature
<222> LOCATION: (115)..(115)
<223> OTHER INFORMATION: X is any aa -- i.e. residue that is not highly
      conserved
<220> FEATURE:
<221> NAME/KEY: misc_feature
<222> LOCATION: (117)..(117)
<223> OTHER INFORMATION: X is any aa -- i.e. residue that is not highly
      conserved
<220> FEATURE:
<221> NAME/KEY: misc_feature
<222> LOCATION: (120)..(120)
<223> OTHER INFORMATION: X is any aa -- i.e. residue that is not highly
      conserved
<220> FEATURE:
<221> NAME/KEY: misc_feature
<222> LOCATION: (127)..(129)
<223> OTHER INFORMATION: X is any aa -- i.e. residue that is not highly
      conserved
<220> FEATURE:
<221> NAME/KEY: misc_feature
<222> LOCATION: (131)..(131)
<223> OTHER INFORMATION: X is any aa -- i.e. residue that is not highly
      conserved
<220> FEATURE:
<221> NAME/KEY: misc_feature
<222> LOCATION: (133)..(133)
<223> OTHER INFORMATION: X is any aa -- i.e. residue that is not highly
      conserved
<220> FEATURE:
<221> NAME/KEY: misc_feature
<222> LOCATION: (135)..(143)
<223> OTHER INFORMATION: X is any aa -- i.e. residue that is not highly
      conserved

<400> SEQUENCE: 31

Cys Gly Gly Xaa Leu Xaa Xaa Xaa Xaa Xaa Xaa Xaa Gly Xaa Phe Ser
1               5                   10                  15

Ser Pro Xaa Tyr Pro Xaa Xaa Tyr Pro Pro Xaa Xaa Xaa Xaa Cys Xaa
            20                  25                  30

Trp Xaa Ile Xaa Val Xaa Xaa Gly Xaa Xaa Ile Xaa Leu Xaa Phe Xaa
        35                  40                  45

Xaa Xaa Phe Asp Leu Xaa Xaa Xaa Xaa Xaa Xaa Xaa Xaa Cys Pro
    50                  55                  60

Tyr Xaa Xaa Xaa Asp Tyr Val Glu Ile Arg Xaa Xaa Gly Xaa Xaa
65              70                  75                  80

Xaa Xaa Xaa Xaa Xaa Gly Xaa Xaa Cys Gly Xaa Xaa Pro Xaa Xaa
                85                  90                  95

Ile Xaa Xaa Xaa Xaa Xaa Xaa Xaa Xaa Xaa Ser Ser Asn Arg Xaa
        100                 105                 110
```

```
Xaa Val Xaa Phe Xaa Ser Asp Xaa Ser Xaa Xaa Xaa Xaa Gly Xaa Xaa
        115                 120                 125

Xaa Phe Xaa Ala Xaa Tyr Xaa Xaa Xaa Xaa Xaa Xaa Xaa
    130                 135                 140
```

```
<210> SEQ ID NO 32
<211> LENGTH: 30
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (1)..(30)
<223> OTHER INFORMATION: PCR primer -- forward

<400> SEQUENCE: 32
tgcgacagtg tgaacgactg cggagacaac                                      30

<210> SEQ ID NO 33
<211> LENGTH: 30
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (1)..(30)
<223> OTHER INFORMATION: PCR primer

<400> SEQUENCE: 33
ctccacgctg gacaggggtc ccccggaatc                                      30

<210> SEQ ID NO 34
<211> LENGTH: 7
<212> TYPE: PRT
<213> ORGANISM: Artificial
<220> FEATURE:
<223> OTHER INFORMATION: Tag

<400> SEQUENCE: 34
```

```
Arg Gly Ser His His His His
1               5
```

```
<210> SEQ ID NO 35
<211> LENGTH: 241
<212> TYPE: PRT
<213> ORGANISM: Homo sapiens

<400> SEQUENCE: 35
```

```
Val Val Gly Gly Thr Asp Ala Asp Glu Gly Glu Trp Pro Trp Gln Val
1               5                   10                  15

Ser Leu His Ala Leu Gly Gln Gly His Ile Cys Gly Ala Ser Leu Ile
            20                  25                  30

Ser Pro Asn Trp Leu Val Ser Ala Ala His Cys Tyr Ile Asp Asp Arg
        35                  40                  45

Gly Phe Arg Tyr Ser Asp Pro Thr Gln Trp Thr Ala Phe Leu Gly Leu
    50                  55                  60

His Asp Gln Ser Gln Arg Ser Ala Pro Gly Val Gln Glu Arg Arg Leu
65                  70                  75                  80

Lys Arg Ile Ile Ser His Pro Phe Phe Asn Asp Phe Thr Phe Asp Tyr
                85                  90                  95

Asp Ile Ala Leu Leu Glu Leu Glu Lys Pro Ala Glu Tyr Ser Ser Met
            100                 105                 110
```

```
Val Arg Pro Ile Cys Leu Pro Asp Ala Ser His Val Phe Pro Ala Gly
        115                 120                 125
Lys Ala Ile Trp Val Thr Gly Trp Gly His Thr Gln Tyr Gly Gly Thr
130                 135                 140
Gly Ala Leu Ile Leu Gln Lys Gly Glu Ile Arg Val Ile Asn Gln Thr
145                 150                 155                 160
Thr Cys Glu Asn Leu Leu Pro Gln Gln Ile Thr Pro Arg Met Met Cys
                165                 170                 175
Val Gly Phe Leu Ser Gly Gly Val Asp Ser Cys Gln Gly Asp Ser Gly
            180                 185                 190
Gly Pro Leu Ser Ser Val Glu Ala Asp Gly Arg Ile Phe Gln Ala Gly
        195                 200                 205
Val Val Ser Trp Gly Asp Gly Cys Ala Gln Arg Asn Lys Pro Gly Val
    210                 215                 220
Tyr Thr Arg Leu Pro Leu Phe Arg Asp Trp Ile Lys Glu Asn Thr Gly
225                 230                 235                 240
Val
```

```
<210> SEQ ID NO 36
<211> LENGTH: 245
<212> TYPE: PRT
<213> ORGANISM: Homo sapiens

<400> SEQUENCE: 36

Ile Val Gly Gly Gln Glu Ala Pro Arg Ser Lys Trp Pro Trp Gln Val
1               5                   10                  15
Ser Leu Arg Val His Asp Arg Tyr Trp Met His Phe Cys Gly Gly Ser
            20                  25                  30
Leu Ile His Pro Gln Trp Val Leu Thr Ala Ala His Cys Val Gly Pro
        35                  40                  45
Asp Val Lys Asp Leu Ala Ala Leu Arg Val Gln Leu Arg Glu Gln His
    50                  55                  60
Leu Tyr Tyr Gln Asp Gln Leu Leu Pro Val Ser Arg Ile Ile Val His
65                  70                  75                  80
Pro Gln Phe Tyr Thr Ala Gln Ile Gly Ala Asp Ile Ala Leu Leu Glu
                85                  90                  95
Leu Glu Glu Pro Val Lys Val Ser Ser His Val His Thr Val Thr Leu
            100                 105                 110
Pro Pro Ala Ser Glu Thr Phe Pro Pro Gly Met Pro Cys Trp Val Thr
        115                 120                 125
Gly Trp Gly Asp Val Asp Asn Asp Glu Arg Leu Pro Pro Pro Phe Pro
130                 135                 140
Leu Lys Gln Val Lys Val Pro Ile Met Glu Asn His Ile Cys Asp Ala
145                 150                 155                 160
Lys Tyr His Leu Gly Ala Tyr Thr Gly Asp Asp Val Arg Ile Val Arg
                165                 170                 175
Asp Asp Met Leu Cys Ala Gly Asn Thr Arg Arg Asp Ser Cys Gln Gly
            180                 185                 190
Asp Ser Gly Gly Pro Leu Val Cys Lys Val Asn Gly Thr Trp Leu Gln
        195                 200                 205
Ala Gly Val Val Ser Trp Gly Glu Gly Cys Ala Gln Pro Asn Arg Pro
    210                 215                 220
Gly Ile Tyr Thr Arg Val Thr Tyr Tyr Leu Asp Trp Ile His His Tyr
225                 230                 235                 240
```

Val Pro Lys Lys Pro
            245

<210> SEQ ID NO 37
<211> LENGTH: 235
<212> TYPE: PRT
<213> ORGANISM: Homo sapiens

<400> SEQUENCE: 37

Ile Val Gly Gly Ser Asn Ala Lys Glu Gly Ala Trp Pro Trp Val Val
1               5                   10                  15

Gly Leu Tyr Tyr Gly Gly Arg Leu Leu Cys Gly Ala Ser Leu Val Ser
            20                  25                  30

Ser Asp Trp Leu Val Ser Ala Ala His Cys Val Tyr Gly Arg Asn Leu
        35                  40                  45

Glu Pro Ser Lys Trp Thr Ala Ile Leu Gly Leu His Met Lys Ser Asn
50                  55                  60

Leu Thr Ser Pro Gln Thr Val Pro Arg Leu Ile Asp Glu Ile Val Ile
65                  70                  75                  80

Asn Pro His Tyr Asn Arg Arg Lys Asp Asn Asp Ile Ala Met Met
                85                  90                  95

His Leu Glu Phe Lys Val Asn Tyr Thr Asp Tyr Ile Gln Pro Ile Cys
            100                 105                 110

Leu Pro Glu Glu Asn Gln Val Phe Pro Pro Gly Arg Asn Cys Ser Ile
        115                 120                 125

Ala Gly Trp Gly Thr Val Val Tyr Gln Gly Thr Thr Ala Asn Ile Leu
130                 135                 140

Gln Glu Ala Asp Val Pro Leu Leu Ser Asn Glu Arg Cys Gln Gln Gln
145                 150                 155                 160

Met Pro Glu Tyr Asn Ile Thr Glu Asn Met Ile Cys Ala Gly Tyr Glu
                165                 170                 175

Glu Gly Gly Ile Asp Ser Cys Gln Gly Asp Ser Gly Gly Pro Leu Met
            180                 185                 190

Cys Gln Glu Asn Asn Arg Trp Phe Leu Ala Gly Val Thr Ser Phe Gly
        195                 200                 205

Tyr Lys Cys Ala Leu Pro Asn Arg Pro Gly Val Tyr Ala Arg Val Ser
    210                 215                 220

Arg Phe Thr Glu Trp Ile Gln Ser Phe Leu His
225                 230                 235

<210> SEQ ID NO 38
<211> LENGTH: 255
<212> TYPE: PRT
<213> ORGANISM: Homo sapiens

<400> SEQUENCE: 38

Ile Val Gly Gly Arg Asp Thr Ser Leu Gly Arg Trp Pro Trp Gln Val
1               5                   10                  15

Ser Leu Arg Tyr Asp Gly Ala His Leu Cys Gly Gly Ser Leu Leu Ser
            20                  25                  30

Gly Asp Trp Val Leu Thr Ala Ala His Cys Phe Pro Glu Arg Asn Arg
        35                  40                  45

Val Leu Ser Arg Trp Arg Val Phe Ala Gly Ala Val Ala Gln Ala Ser
50                  55                  60

Pro His Gly Leu Gln Leu Gly Val Gln Ala Val Val Tyr His Gly Gly
65                  70                  75                  80

-continued

Tyr Leu Pro Phe Arg Asp Pro Asn Ser Glu Glu Asn Ser Asn Asp Ile
                85                  90                  95

Ala Leu Val His Leu Ser Ser Pro Leu Pro Leu Thr Glu Tyr Ile Gln
            100                 105                 110

Pro Val Cys Leu Pro Ala Ala Gly Gln Ala Leu Val Asp Gly Lys Ile
        115                 120                 125

Cys Thr Val Thr Gly Trp Gly Asn Thr Gln Tyr Tyr Gly Gln Gln Ala
130                 135                 140

Gly Val Leu Gln Glu Ala Arg Val Pro Ile Ile Ser Asn Asp Val Cys
145                 150                 155                 160

Asn Gly Ala Asp Phe Tyr Gly Asn Gln Ile Lys Pro Lys Met Phe Cys
                165                 170                 175

Ala Gly Tyr Pro Glu Gly Gly Ile Asp Ala Cys Gln Gly Asp Ser Gly
            180                 185                 190

Gly Pro Phe Val Cys Glu Asp Ser Ile Ser Arg Thr Pro Arg Trp Arg
        195                 200                 205

Leu Cys Gly Ile Val Ser Trp Gly Thr Gly Cys Ala Leu Ala Gln Lys
210                 215                 220

Pro Gly Val Tyr Thr Lys Val Ser Asp Phe Arg Glu Trp Ile Phe Gln
225                 230                 235                 240

Ala Ile Lys Thr His Ser Glu Ala Ser Gly Met Val Thr Gln Leu
                245                 250                 255

<210> SEQ ID NO 39
<211> LENGTH: 224
<212> TYPE: PRT
<213> ORGANISM: Homo sapiens

<400> SEQUENCE: 39

Ile Val Gly Gly Tyr Ile Cys Glu Glu Asn Ser Val Pro Tyr Gln Val
1               5                   10                  15

Ser Leu Asn Ser Gly Tyr His Phe Cys Gly Gly Ser Leu Ile Ser Glu
            20                  25                  30

Gln Trp Val Val Ser Ala Gly His Cys Tyr Lys Ser Arg Ile Gln Val
        35                  40                  45

Arg Leu Gly Glu His Asn Ile Glu Val Leu Glu Gly Asn Glu Gln Phe
    50                  55                  60

Ile Asn Ala Ala Lys Ile Ile Arg His Pro Lys Tyr Asn Ser Arg Thr
65                  70                  75                  80

Leu Asp Asn Asp Ile Leu Leu Ile Lys Leu Ser Ser Pro Ala Val Ile
                85                  90                  95

Asn Ser Arg Val Ser Ala Ile Ser Leu Pro Thr Ala Pro Pro Ala Ala
            100                 105                 110

Gly Thr Glu Ser Leu Ile Ser Gly Trp Gly Asn Thr Leu Ser Ser Gly
        115                 120                 125

Ala Asp Tyr Pro Asp Glu Leu Gln Cys Leu Asp Ala Pro Val Leu Ser
    130                 135                 140

Gln Ala Glu Cys Glu Ala Ser Tyr Pro Gly Lys Ile Thr Asn Asn Met
145                 150                 155                 160

Phe Cys Val Gly Phe Leu Glu Gly Gly Lys Asp Ser Cys Gln Gly Asp
                165                 170                 175

Ser Gly Gly Pro Val Val Ser Asn Gly Glu Leu Gln Gly Ile Val Ser
            180                 185                 190

Trp Gly Tyr Gly Cys Ala Gln Lys Asn Arg Pro Gly Val Tyr Thr Lys

-continued

```
                195                 200                 205
Val Tyr Asn Tyr Val Asp Trp Ile Lys Asp Thr Ile Ala Ala Asn Ser
    210                 215                 220
```

<210> SEQ ID NO 40
<211> LENGTH: 230
<212> TYPE: PRT
<213> ORGANISM: Homo sapiens

<400> SEQUENCE: 40

```
Ile Val Asn Gly Glu Asp Ala Val Pro Gly Ser Trp Pro Trp Gln Val
1               5                   10                  15

Ser Leu Gln Asp Lys Thr Gly Phe His Phe Cys Gly Gly Ser Leu Ile
            20                  25                  30

Ser Glu Asp Trp Val Val Thr Ala Ala His Cys Gly Val Arg Thr Ser
        35                  40                  45

Asp Val Val Ala Gly Glu Phe Asp Gln Gly Ser Asp Glu Glu Asn
    50                  55                  60

Ile Gln Val Leu Lys Ile Ala Lys Val Phe Lys Asn Pro Lys Phe Ser
65                  70                  75                  80

Ile Leu Thr Val Asn Asn Asp Ile Thr Leu Leu Lys Leu Ala Thr Pro
                85                  90                  95

Ala Arg Phe Ser Gln Thr Val Ser Ala Val Cys Leu Pro Ser Ala Asp
            100                 105                 110

Asp Asp Phe Pro Ala Gly Thr Leu Cys Ala Thr Thr Gly Trp Gly Lys
        115                 120                 125

Thr Lys Tyr Asn Ala Asn Lys Thr Pro Asp Lys Leu Gln Gln Ala Ala
    130                 135                 140

Leu Pro Leu Leu Ser Asn Ala Glu Cys Lys Lys Ser Trp Gly Arg Arg
145                 150                 155                 160

Ile Thr Asp Val Met Ile Cys Ala Gly Ala Ser Gly Val Ser Ser Cys
                165                 170                 175

Met Gly Asp Ser Gly Gly Pro Leu Val Cys Gln Lys Asp Gly Ala Trp
            180                 185                 190

Thr Leu Val Gly Ile Val Ser Trp Gly Ser Asp Thr Cys Ser Thr Ser
        195                 200                 205

Ser Pro Gly Val Tyr Ala Arg Val Thr Lys Leu Ile Pro Trp Val Gln
    210                 215                 220

Lys Ile Leu Ala Ala Asn
225                 230
```

<210> SEQ ID NO 41
<211> LENGTH: 152
<212> TYPE: PRT
<213> ORGANISM: Homo sapiens

<400> SEQUENCE: 41

```
Cys Pro Gly Gln Phe Thr Cys Arg Thr Gly Arg Cys Ile Arg Lys Glu
1               5                   10                  15

Leu Arg Cys Asp Gly Trp Ala Asp Cys Thr Asp His Ser Asp Glu Leu
            20                  25                  30

Asn Cys Ser Cys Asp Ala Gly His Gln Phe Thr Cys Lys Asn Lys Phe
        35                  40                  45

Cys Lys Pro Leu Phe Trp Val Cys Asp Ser Val Asn Asp Cys Gly Asp
    50                  55                  60

Asn Ser Asp Glu Gln Gly Cys Ser Cys Pro Ala Gln Thr Phe Arg Cys
```

```
              65                  70                  75                  80
Ser Asn Gly Lys Cys Leu Ser Lys Ser Gln Gln Cys Asn Gly Lys Asp
                    85                  90                  95

Asp Cys Gly Asp Gly Ser Asp Glu Ala Ser Cys Pro Lys Val Asn Val
                    100                 105                 110

Val Thr Cys Thr Lys His Thr Tyr Arg Cys Leu Leu Asn Gly Leu Cys
                    115                 120                 125

Leu Ser Lys Gly Asn Pro Glu Cys Asp Gly Lys Glu Asp Cys Ser Asp
            130                 135                 140

Gly Ser Asp Glu Lys Asp Cys Asp
145                 150

<210> SEQ ID NO 42
<211> LENGTH: 290
<212> TYPE: PRT
<213> ORGANISM: Homo sapiens

<400> SEQUENCE: 42

Cys Glu Arg Asn Glu Phe Gln Cys Gln Asp Gly Lys Cys Ile Ser Tyr
1               5                   10                  15

Lys Trp Val Cys Asp Gly Ser Ala Glu Cys Gln Asp Gly Ser Asp Glu
                20                  25                  30

Ser Gln Glu Thr Cys Leu Ser Val Thr Cys Lys Ser Gly Asp Phe Ser
            35                  40                  45

Cys Gly Gly Arg Val Asn Arg Cys Ile Pro Gln Phe Trp Arg Cys Asp
50                  55                  60

Gly Gln Val Asp Cys Asp Asn Gly Ser Asp Glu Gln Gly Cys Pro Pro
65                  70                  75                  80

Lys Thr Cys Ser Gln Asp Glu Phe Arg Cys His Asp Gly Lys Cys Ile
                85                  90                  95

Ser Arg Gln Phe Val Cys Asp Ser Arg Asp Cys Leu Asp Gly Ser Asp
                100                 105                 110

Glu Ala Ser Cys Pro Val Leu Thr Cys Gly Pro Ala Ser Phe Gln Cys
            115                 120                 125

Asn Ser Ser Thr Cys Ile Pro Gln Leu Trp Ala Cys Asp Asn Asp Pro
            130                 135                 140

Asp Cys Glu Asp Gly Ser Asp Glu Trp Pro Gln Arg Cys Arg Gly Leu
145                 150                 155                 160

Tyr Val Phe Gln Gly Asp Ser Ser Pro Cys Ser Ala Phe Glu Phe His
                165                 170                 175

Cys Leu Ser Gly Glu Cys Ile His Ser Ser Trp Arg Cys Asp Gly Gly
            180                 185                 190

Pro Asp Cys Lys Asp Lys Ser Asp Glu Glu Asn Cys Ala Val Ala Thr
            195                 200                 205

Cys Arg Pro Asp Glu Phe Gln Cys Ser Asp Gly Asn Cys Ile His Gly
            210                 215                 220

Ser Arg Gln Cys Asp Arg Glu Tyr Asp Cys Lys Asp Met Ser Asp Glu
225                 230                 235                 240

Val Gly Cys Val Asn Val Thr Leu Cys Glu Gly Pro Asn Lys Phe Lys
                245                 250                 255

Cys His Ser Gly Glu Cys Ile Thr Leu Asp Lys Val Cys Asn Met Ala
            260                 265                 270

Arg Asp Cys Arg Asp Trp Ser Asp Glu Pro Ile Lys Glu Cys Gly Thr
            275                 280                 285
```

```
Asn Glu
    290

<210> SEQ ID NO 43
<211> LENGTH: 152
<212> TYPE: PRT
<213> ORGANISM: Homo sapiens

<400> SEQUENCE: 43

Cys Ser Phe Gly Leu His Ala Arg Gly Val Glu Leu Met Arg Phe Thr
1               5                   10                  15

Thr Pro Gly Phe Pro Asp Ser Pro Tyr Pro Ala His Ala Arg Cys Gln
            20                  25                  30

Trp Ala Leu Arg Gly Asp Ala Asp Ser Val Leu Ser Leu Thr Phe Arg
        35                  40                  45

Ser Phe Asp Leu Ala Ser Cys Asp Glu Arg Gly Ser Asp Leu Val Thr
    50                  55                  60

Val Tyr Asn Thr Leu Ser Pro Met Glu Pro His Ala Leu Val Gln Leu
65                  70                  75                  80

Cys Cys Gly Gly Arg Leu Arg Lys Ala Gln Gly Thr Phe Asn Ser Pro
                85                  90                  95

Tyr Tyr Pro Gly His Tyr Pro Asn Ile Asp Cys Thr Trp Asn Ile
            100                 105                 110

Glu Val Pro Asn Asn Gln His Val Lys Val Arg Phe Lys Phe Phe Tyr
        115                 120                 125

Leu Leu Glu Pro Gly Val Pro Ala Gly Thr Cys Pro Lys Asp Tyr Val
    130                 135                 140

Glu Ile Asn Gly Glu Lys Tyr Cys
145                 150

<210> SEQ ID NO 44
<211> LENGTH: 74
<212> TYPE: PRT
<213> ORGANISM: Homo sapiens

<400> SEQUENCE: 44

Cys Asp Gly Arg Phe Leu Leu Thr Gly Ser Ser Gly Ser Phe Gln Ala
1               5                   10                  15

Thr His Tyr Pro Lys Pro Ser Glu Thr Ser Val Val Cys Gln Trp Ile
            20                  25                  30

Ile Arg Val Asn Gln Gly Leu Ser Ile Lys Leu Ser Phe Asp Asp Phe
        35                  40                  45

Asn Thr Tyr Tyr Thr Asp Ile Leu Asp Ile Tyr Glu Gly Val Gly Ser
    50                  55                  60

Ser Lys Ile Leu Arg Ala Ser Ile Trp Glu
65                  70

<210> SEQ ID NO 45
<211> LENGTH: 74
<212> TYPE: PRT
<213> ORGANISM: Homo sapiens

<400> SEQUENCE: 45

Cys Gly Gly Pro Phe Glu Leu Trp Glu Pro Asn Thr Thr Phe Ser Ser
1               5                   10                  15

Thr Asn Phe Pro Asn Ser Tyr Pro Asn Leu Ala Phe Cys Val Trp Ile
            20                  25                  30

Leu Asn Ala Gln Lys Gly Lys Asn Ile Gln Leu His Phe Gln Glu Phe
```

```
              35                  40                  45
Asp Leu Glu Asn Ile Asn Asp Val Val Glu Ile Arg Asp Gly Glu Glu
     50                  55                  60

Ala Asp Ser Leu Leu Leu Ala Val Tyr Thr
 65                  70
```

<210> SEQ ID NO 46
<211> LENGTH: 76
<212> TYPE: PRT
<213> ORGANISM: Homo sapiens

<400> SEQUENCE: 46

```
Cys Gly Glu Thr Leu Gln Asp Ser Thr Gly Asn Phe Ser Ser Pro Glu
 1               5                  10                  15

Tyr Pro Asn Gly Tyr Ser Ala His Met His Cys Val Trp Arg Ile Ser
             20                  25                  30

Val Thr Pro Gly Glu Lys Ile Ile Leu Asn Phe Thr Ser Leu Asp Leu
         35                  40                  45

Tyr Arg Ser Arg Leu Cys Trp Tyr Asp Tyr Val Glu Val Arg Asp Gly
     50                  55                  60

Phe Trp Arg Lys Ala Pro Leu Arg Gly Arg Phe Cys
 65                  70                  75
```

<210> SEQ ID NO 47
<211> LENGTH: 76
<212> TYPE: PRT
<213> ORGANISM: Homo sapiens

<400> SEQUENCE: 47

```
Cys Gly Gly Asp Val Lys Lys Asp Tyr Gly His Ile Gln Ser Pro Asn
 1               5                  10                  15

Tyr Pro Asp Asp Tyr Arg Pro Ser Lys Val Cys Ile Trp Arg Ile Gln
             20                  25                  30

Val Ser Glu Gly Phe His Val Gly Leu Thr Phe Gln Ser Phe Glu Ile
         35                  40                  45

Glu Arg His Asp Ser Cys Ala Tyr Asp Tyr Leu Glu Val Arg Asp Gly
     50                  55                  60

His Ser Glu Ser Ser Thr Leu Ile Gly Arg Tyr Cys
 65                  70                  75
```

<210> SEQ ID NO 48
<211> LENGTH: 76
<212> TYPE: PRT
<213> ORGANISM: Homo sapiens

<400> SEQUENCE: 48

```
Cys Gly Gly Phe Leu Thr Lys Leu Asn Gly Ser Ile Thr Ser Pro Gly
 1               5                  10                  15

Trp Pro Lys Glu Tyr Pro Pro Asn Lys Asn Cys Ile Trp Gln Leu Val
             20                  25                  30

Ala Pro Thr Gln Tyr Arg Ile Ser Leu Gln Phe Asp Phe Phe Glu Thr
         35                  40                  45

Glu Gly Asn Asp Val Cys Lys Tyr Asp Phe Val Glu Val Arg Ser Gly
     50                  55                  60

Leu Thr Ala Asp Ser Lys Leu His Gly Lys Phe Cys
 65                  70                  75
```

<210> SEQ ID NO 49

<211> LENGTH: 71
<212> TYPE: PRT
<213> ORGANISM: Homo sapiens

<400> SEQUENCE: 49

```
Ser Ile Pro Ile Pro Gln Lys Leu Phe Gly Glu Val Thr Ser Pro Leu
1               5                   10                  15

Phe Pro Lys Pro Tyr Pro Asn Asn Phe Glu Thr Thr Thr Val Ile Thr
            20                  25                  30

Val Pro Thr Gly Tyr Arg Val Lys Leu Val Phe Gln Gln Phe Asp Leu
        35                  40                  45

Glu Pro Ser Glu Gly Cys Phe Tyr Asp Tyr Val Lys Ile Ser Ala Asp
    50                  55                  60

Lys Lys Leu Gly Arg Phe Cys
65                  70
```

<210> SEQ ID NO 50
<211> LENGTH: 75
<212> TYPE: PRT
<213> ORGANISM: Homo sapiens

<400> SEQUENCE: 50

```
Cys Ser Ser Glu Tyr Thr Glu Ala Ser Gly Tyr Ile Ser Ser Leu Glu
1               5                   10                  15

Tyr Pro Arg Ser Tyr Pro Pro Asp Leu Arg Cys Asn Tyr Ser Ile Arg
            20                  25                  30

Val Glu Arg Gly Leu Thr Leu His Leu Lys Phe Leu Glu Pro Phe Asp
        35                  40                  45

Ile Asp Asp His Gln Gln Val His Cys Pro Tyr Asp Gln Leu Gln Ile
    50                  55                  60

Tyr Ala Asn Gly Lys Asn Ile Gly Glu Phe Cys
65                  70                  75
```

<210> SEQ ID NO 51
<211> LENGTH: 45
<212> TYPE: PRT
<213> ORGANISM: Homo sapiens

<400> SEQUENCE: 51

```
Gly Thr Tyr Pro Pro Ser Tyr Asn Leu Thr Phe His Ser Ser Gln Asn
1               5                   10                  15

Val Leu Leu Ile Thr Leu Ile Thr Asn Thr Glu Arg Arg His Pro Gly
            20                  25                  30

Phe Glu Ala Thr Phe Phe Gln Leu Pro Arg Met Ser Ser
        35                  40                  45
```

<210> SEQ ID NO 52
<211> LENGTH: 42
<212> TYPE: PRT
<213> ORGANISM: Homo sapiens

<400> SEQUENCE: 52

```
Gly Glu Arg Ser Gln Phe Val Val Thr Ser Asn Ser Asn Lys Ile Thr
1               5                   10                  15

Val Arg Phe His Ser Asp Gln Ser Tyr Thr Asp Thr Gly Phe Leu Ala
            20                  25                  30

Glu Tyr Leu Ser Tyr Asp Ser Ser Asp Pro
        35                  40
```

<210> SEQ ID NO 53
<211> LENGTH: 36
<212> TYPE: PRT
<213> ORGANISM: Homo sapiens

<400> SEQUENCE: 53

Thr Asn Pro Gly Thr Ile Arg Ile Phe Ser Asn Gln Val Thr Ala Thr
1               5                   10                  15

Phe Leu Ile Glu Ser Asp Glu Ser Asp Tyr Val Gly Phe Asn Ala Thr
            20                  25                  30

Tyr Thr Ala Phe
        35

<210> SEQ ID NO 54
<211> LENGTH: 37
<212> TYPE: PRT
<213> ORGANISM: Homo sapiens

<400> SEQUENCE: 54

Gly Pro Gly Pro Val Lys Asp Val Phe Ser Thr Thr Asn Arg Met Thr
1               5                   10                  15

Val Leu Leu Ile Thr Asn Asp Val Leu Ala Arg Gly Gly Phe Lys Ala
            20                  25                  30

Asn Phe Thr Thr Gly
        35

<210> SEQ ID NO 55
<211> LENGTH: 37
<212> TYPE: PRT
<213> ORGANISM: Homo sapiens

<400> SEQUENCE: 55

Gly Ser Lys Leu Pro Glu Pro Ile Val Ser Thr Asp Ser Arg Leu Trp
1               5                   10                  15

Val Glu Phe Arg Ser Ser Ser Asn Trp Val Gly Lys Gly Phe Phe Ala
            20                  25                  30

Val Tyr Glu Ala Ile
        35

<210> SEQ ID NO 56
<211> LENGTH: 36
<212> TYPE: PRT
<213> ORGANISM: Homo sapiens

<400> SEQUENCE: 56

Gly Tyr Glu Lys Pro Asp Asp Ile Lys Ser Thr Ser Ser Arg Leu Trp
1               5                   10                  15

Leu Lys Phe Val Ser Asp Gly Ser Ile Asn Lys Ala Gly Phe Ala Val
            20                  25                  30

Asn Phe Phe Lys
        35

<210> SEQ ID NO 57
<211> LENGTH: 37
<212> TYPE: PRT
<213> ORGANISM: Homo sapiens

<400> SEQUENCE: 57

Gly Ser Glu Lys Pro Glu Val Ile Thr Ser Gln Tyr Asn Asn Met Arg
1               5                   10                  15

Val Glu Phe Lys Ser Asp Asn Thr Val Ser Lys Lys Gly Phe Lys Ala

-continued

```
                20                  25                  30

His Phe Phe Ser Glu
        35

<210> SEQ ID NO 58
<211> LENGTH: 52
<212> TYPE: PRT
<213> ORGANISM: Homo sapiens

<400> SEQUENCE: 58

Gly Gln Leu Gly Ser Pro Leu Gly Asn Pro Pro Gly Lys Lys Glu Phe
1               5                   10                  15

Met Ser Gln Gly Asn Lys Met Leu Leu Thr Phe His Thr Asp Phe Ser
            20                  25                  30

Asn Glu Glu Asn Gly Thr Ile Met Phe Tyr Lys Gly Phe Leu Ala Tyr
        35                  40                  45

Tyr Gln Ala Val
    50

<210> SEQ ID NO 59
<211> LENGTH: 37
<212> TYPE: PRT
<213> ORGANISM: Homo sapiens

<400> SEQUENCE: 59

Gly Lys Gln Arg Pro Pro Asp Leu Asp Thr Ser Ser Asn Ala Val Asp
1               5                   10                  15

Leu Leu Phe Phe Thr Asp Glu Ser Gly Asp Ser Arg Gly Trp Lys Leu
            20                  25                  30

Arg Tyr Thr Thr Glu
        35

<210> SEQ ID NO 60
<211> LENGTH: 4
<212> TYPE: PRT
<213> ORGANISM: Artificial
<220> FEATURE:
<223> OTHER INFORMATION: Synthetic peptides based on Homo sapiens
      protein sequences

<400> SEQUENCE: 60

Ile Val Gly Gly
1

<210> SEQ ID NO 61
<211> LENGTH: 7
<212> TYPE: PRT
<213> ORGANISM: Artificial
<220> FEATURE:
<223> OTHER INFORMATION: Synthetic peptides based on Homo sapiens
      protein sequences

<400> SEQUENCE: 61

Trp Pro Trp Gln Val Ser Leu
1               5

<210> SEQ ID NO 62
<211> LENGTH: 7
<212> TYPE: PRT
<213> ORGANISM: Artificial
<220> FEATURE:
<223> OTHER INFORMATION: Synthetic peptides based on Homo sapiens
      protein sequences
```

```
<400> SEQUENCE: 62

Cys Gly Gly Ser Leu Ile Ser
1               5

<210> SEQ ID NO 63
<211> LENGTH: 8
<212> TYPE: PRT
<213> ORGANISM: Artificial
<220> FEATURE:
<223> OTHER INFORMATION: Synthetic peptides based on Homo sapiens
      protein sequences

<400> SEQUENCE: 63

Trp Val Val Ser Ala Ala His Cys
1               5

<210> SEQ ID NO 64
<211> LENGTH: 7
<212> TYPE: PRT
<213> ORGANISM: Artificial
<220> FEATURE:
<223> OTHER INFORMATION: Synthetic peptides based on Homo sapiens
      protein sequences

<400> SEQUENCE: 64

Asp Asn Asp Ile Ala Leu Leu
1               5

<210> SEQ ID NO 65
<211> LENGTH: 5
<212> TYPE: PRT
<213> ORGANISM: Artificial
<220> FEATURE:
<223> OTHER INFORMATION: Synthetic peptides based on Homo sapiens
      protein sequences

<400> SEQUENCE: 65

Pro Ile Cys Leu Pro
1               5

<210> SEQ ID NO 66
<211> LENGTH: 4
<212> TYPE: PRT
<213> ORGANISM: Artificial
<220> FEATURE:
<223> OTHER INFORMATION: Synthetic peptides based on Homo sapiens
      protein sequences

<400> SEQUENCE: 66

Phe Pro Ala Gly
1

<210> SEQ ID NO 67
<211> LENGTH: 5
<212> TYPE: PRT
<213> ORGANISM: Artificial
<220> FEATURE:
<223> OTHER INFORMATION: Synthetic peptides based on Homo sapiens
      protein sequences

<400> SEQUENCE: 67

Val Thr Gly Trp Gly
1               5

<210> SEQ ID NO 68
<211> LENGTH: 12
<212> TYPE: PRT
```

-continued

<213> ORGANISM: Artificial
<220> FEATURE:
<223> OTHER INFORMATION: Synthetic peptides based on Homo sapiens
      protein sequences

<400> SEQUENCE: 68

Asp Ser Cys Gln Gly Asp Ser Gly Gly Pro Leu Val
1               5                   10

<210> SEQ ID NO 69
<211> LENGTH: 6
<212> TYPE: PRT
<213> ORGANISM: Artificial
<220> FEATURE:
<223> OTHER INFORMATION: Synthetic peptides based on Homo sapiens
      protein sequences

<400> SEQUENCE: 69

Gly Val Val Ser Trp Gly
1               5

<210> SEQ ID NO 70
<211> LENGTH: 4
<212> TYPE: PRT
<213> ORGANISM: Artificial
<220> FEATURE:
<223> OTHER INFORMATION: Synthetic peptides based on Homo sapiens
      protein sequences

<400> SEQUENCE: 70

Gly Cys Ala Gln
1

<210> SEQ ID NO 71
<211> LENGTH: 9
<212> TYPE: PRT
<213> ORGANISM: Artificial
<220> FEATURE:
<223> OTHER INFORMATION: Synthetic peptides based on Homo sapiens
      protein sequences

<400> SEQUENCE: 71

Asn Arg Pro Gly Val Tyr Thr Arg Val
1               5

<210> SEQ ID NO 72
<211> LENGTH: 5
<212> TYPE: PRT
<213> ORGANISM: Artificial
<220> FEATURE:
<223> OTHER INFORMATION: Synthetic peptides based on Homo sapiens
      protein sequences

<400> SEQUENCE: 72

Asp Gly Ser Asp Glu
1               5

<210> SEQ ID NO 73
<211> LENGTH: 4
<212> TYPE: PRT
<213> ORGANISM: Artificial
<220> FEATURE:
<223> OTHER INFORMATION: Synthetic peptides based on Homo sapiens
      protein sequences

<400> SEQUENCE: 73

Phe Ser Ser Pro
1

```
<210> SEQ ID NO 74
<211> LENGTH: 6
<212> TYPE: PRT
<213> ORGANISM: Artificial
<220> FEATURE:
<223> OTHER INFORMATION: Synthetic peptides based on Homo sapiens
      protein sequences

<400> SEQUENCE: 74

Asp Tyr Val Glu Ile Arg
1               5

<210> SEQ ID NO 75
<211> LENGTH: 4
<212> TYPE: PRT
<213> ORGANISM: Artificial
<220> FEATURE:
<223> OTHER INFORMATION: Synthetic peptides based on Homo sapiens
      protein sequences

<400> SEQUENCE: 75

Ser Ser Asn Arg
1

<210> SEQ ID NO 76
<211> LENGTH: 4
<212> TYPE: PRT
<213> ORGANISM: Artificial
<220> FEATURE:
<223> OTHER INFORMATION: Activation peptide

<400> SEQUENCE: 76

Ile Ile Gly Gly
1

<210> SEQ ID NO 77
<211> LENGTH: 5
<212> TYPE: PRT
<213> ORGANISM: Artificial
<220> FEATURE:
<223> OTHER INFORMATION: Linking peptide

<400> SEQUENCE: 77

Gly Gly Gly Gly Ser
1               5

<210> SEQ ID NO 78
<211> LENGTH: 5
<212> TYPE: PRT
<213> ORGANISM: Artificial
<220> FEATURE:
<223> OTHER INFORMATION: Endoplasmic retention sequence

<400> SEQUENCE: 78

Arg Glu Asp Leu Lys
1               5

<210> SEQ ID NO 79
<211> LENGTH: 4
<212> TYPE: PRT
<213> ORGANISM: Artificial
<220> FEATURE:
<223> OTHER INFORMATION: Endoplasmic refention sequence

<400> SEQUENCE: 79

Arg Glu Asp Leu
```

-continued

```
<210> SEQ ID NO 80
<211> LENGTH: 4
<212> TYPE: PRT
<213> ORGANISM: Artificial
<220> FEATURE:
<223> OTHER INFORMATION: Endoplasmic retention sequence

<400> SEQUENCE: 80

Arg Asp Glu Leu
1

<210> SEQ ID NO 81
<211> LENGTH: 4
<212> TYPE: PRT
<213> ORGANISM: Artificial
<220> FEATURE:
<223> OTHER INFORMATION: Endoplasmic retention sequence

<400> SEQUENCE: 81

Lys Asp Glu Leu
1

<210> SEQ ID NO 82
<211> LENGTH: 10
<212> TYPE: PRT
<213> ORGANISM: Artificial
<220> FEATURE:
<223> OTHER INFORMATION: His tag

<400> SEQUENCE: 82

Met Arg Gly Ser His His His His His His
1               5                   10

<210> SEQ ID NO 83
<211> LENGTH: 5
<212> TYPE: PRT
<213> ORGANISM: Artificial
<220> FEATURE:
<223> OTHER INFORMATION: Activation sequence

<400> SEQUENCE: 83

Val Val Gly Gly Thr
1               5
```

MT-SP1 POLYNUCLEOTIDES AND POLYPEPTIDES

CROSS-REFERENCE TO RELATED APPLICATIONS

This application is a continuation application of Ser. No. 09/410,362, filed Sep. 30, 1999 now U.S. Pat. No. 7,030,231, which is incorporated herein by reference in its entirety.

STATEMENT AS TO RIGHTS TO INVENTIONS MADE UNDER FEDERALLY SPONSORED RESEARCH AND DEVELOPMENT

This work was supported, in part, by National Institutes of Health Grants Numbers CA72006 and CA71097. The Government of the United States of America may have some rights in this invention.

FIELD OF THE INVENTION

This invention relates to the field of serine proteases and associated biology. In particular, this invention relates to the discovery of a new membrane-type serine protease believed to be associated with the etiology of cancer and associated pathologies.

BACKGROUND OF THE INVENTION

The serine proteases (SP) are a large family of proteolytic enzymes that include the digestive enzymes, trypsin and chymotrypsin, components of the complement cascade and of the blood-clotting cascade, and enzymes that control the degradation and turnover of macromolecules of the extracellular matrix. Serine proteases are so named because of the presence of a serine residue in the active catalytic site for protein cleavage. Serine proteases have a wide range of substrate specificities and can be subdivided into subfamilies on the basis of these specificities. The main sub-families are trypases (cleavage after arginine or lysine), aspases (cleavage after aspartate), chymases (cleavage after phenylalanine or leucine), metases (cleavage after methionine), and serases (cleavage after serine).

Most proteases are secretory proteins which contain N-terminal signal peptides that serve to export the immature protein across the endoplasmic reticulum and are then cleaved (von Heijne (1986) *Nuc. Acid. Res.* 14: 5683–5690). Differences in these signal sequences provide one means of distinguishing individual serine proteases. Some serine proteases, particularly the digestive enzymes, exist as inactive precursors or preproenzymes, and contain a leader or activation peptide sequence 3' of the signal peptide. Typically, this activation peptide may be 2–12 amino acids in length, and it extends from the cleavage site of the signal peptide to the N-terminal IIGG (SEQ ID NO:76) sequence of the active, mature protein. Cleavage of this sequence activates the enzyme. This sequence varies in different serine proteases according to the biochemical pathway and/or its substrate (Zunino et al. (1988) *Biochimica et. Biophysica Acta* 967: 331–340; Sayers, et al. (1992) *J. Immunology* 148: 292–300). Other features that distinguish various serine proteases are the presence or absence of N-linked glycosylation sites that provide membrane anchors, the number and distribution of cysteine residues that determine the secondary structure of the serine protease and the sequence of a substrate binding sites such as S'. The S' substrate binding region is defined by residues extending from approximately +17 to +29 relative to the N-terminal I (+1). Differences in this region of the molecule are believed to determine serine protease substrate specificities (Zunino et al, supra).

Numerous disease states are caused by and can be characterized by alterations in the activity of specific proteases and their inhibitors. For example emphysema, arthritis, thrombosis, cancer metastasis and some forms of hemophilia result from the lack of regulation of serine protease activities (see, for example, *Textbook of Biochemistry with Clinical Correlations*, John Wiley and Sons, Inc. N.Y. (1993)). In case of viral infection, the presence of viral proteases have been identified in infected cells. Such viral proteases include, for example, HIV protease associated with AIDS and NS3 protease associated with Hepatitis C. These viral proteases play a critical role in the virus life cycle.

A series of serine proteases have been identified in murine cytotoxic T-lymphocytes (CTL) and natural killer (NK) cells. These serine proteases are involved with CTL and NK cells in the destruction of virally transformed cells and tumor cells and in organ and tissue transplant rejection (Zunino et al. (1990) *J. Immunol.* 144: 2001–2009; Sayers et al. (1994) *J. Immunol.* 152: 2289–2297). Human homologs of most of these enzymes have been identified (Trapaniet et al. (1988) *Proc. Natl. Acad. Sci.* 85: 6924–6928; Caputo et al. (1990) *J. Immunol.* 145: 737–744).

Proteases have also been implicated in cancer metastasis. Increased synthesis of the protease urokinase has been correlated with an increased ability to metastasize in many cancers. Urokinase activates plasmin from plasminogen which is ubiquitously located in the extracellular space and its activation can cause the degradation of the proteins in the extracellular matrix through which the metastasizing tumor cells invade. Plasmin can also activate the collagenases thus promoting the degradation of the collagen in the basement membrane surrounding the capillaries and lymph system thereby allowing tumor cells to invade into the target tissues (Dano, et al. (1985) *Adv. Cancer. Res.*, 44: 139).

The discovery of a new serine protease precursor and the polynucleotides encoding it satisfies a need in the art by providing new prognostic and diagnostic diagnostic methods and, therapeutic compositions useful in the treatment or prevention of cancer.

SUMMARY OF THE INVENTION

This invention pertains to the discovery of a new serine protease associated with cancer cells. In particular, nucleic acid cDNAs derived from PC-3 mRNA were sequenced that encoded a novel serine protease referred to herein as membrane-type serine protease 1 (MT-SP1). The MT-SP1 polypeptide encoded by the nucleic acid(s) is localized in tumor tissues (e.g. prostatic cancers, gastric cancers, breast cancers, etc.), and in preferred embodiments is identified in blood vessels associated with tumors. Inhibition of MT-SP1 inhibits cancer growth in relevant animal models. Without being bound to a particular theory it is believed that MT-SP1 is implicated in tumor proliferation and/or growth and/or tumor angiogenesis. MT-SP1 is also demonstrated herein to be a good diagnostic, and more preferably, a good prognostic for various cancers. MT-SP1 can be used to detect the presence or absence of a cancer, to determine the location and/or size and/or morphology of a cancer, and to make a prediction regarding the severity and/or outcome of a cancer or a particular therapeutic regimen.

In one embodiment, this invention provides nucleic acids encoding MT-SP1 and/or probes suitable for amplification of MT-SP1 nucleic acids (e.g. from a PC-3 mRNA template). These nucleic acids include, but are not limited to: (a) a nucleic acid comprising a nucleic acid encoding a serine protease domain having the sequence of SEQ ID NO: 2; (b) a nucleic acid comprising a nucleic acid encoding a serine protease domain having the sequence of amino acids 615 through 855 of SEQ ID NO:2; (c) a nucleic acid that specifically hybridizes to the nucleic acid of SEQ ID NO: 1 or a fragment thereof under stringent conditions and is of sufficient length that said nucleic acid can uniquely indicate the presence or absence of a nucleic acid encoding a membrane-type serine protease in a total genomic DNA pool, a total cDNA pool or a total mRNA pool sample from a PC-3 cell; (d) a nucleic acid comprising a sequence that has the same sequence as a nucleic acid amplified from a PC-3 cDNA template using PCR primers corresponding to nucleotides 37–54 of SEQ ID NO: 1 and 2604–2583 of the complement of SEQ ID NO: 1; (e) a DNA encoding an mRNA that, when reverse transcribed, produces the cDNA of SEQ ID NO: 1; (f) a DNA encoding an mRNA that, when reverse transcribed, produces the cDNA encoding amino acids 615–855 of SEQ ID NO: 2; (g) a pair of primers that, when used in a nucleic acid amplification reaction with PC-3 cDNA template specifically amplifies a nucleic acid encoding the polypeptide of SEQ ID NO: 2; (h) a pair of primers that, when used in a nucleic acid amplification reaction with mRNA template from a PC-3 cell specifically amplify a nucleic acid encoding the polypeptide having the sequence of amino acids 615 through 855 of SEQ ID NO: 2; and (i) a nucleic acid encoding a membrane-type serine protease, wherein said nucleic acid encodes a consensus sequence shown in FIG. 4 and does not encode TRYB_human, ENTK-Human, HEPS_human, TRY2_Human, and CTRB_human. Preferred nucleic acids encode a polypeptide having the sequence of amino acids 615 through 855 of SEQ ID NO: 2, while other preferred nucleic acids encode a polypeptide having the sequence of SEQ ID NO: 2. In one embodiment the nucleic acid has the sequence of SEQ ID NO: 1. The nucleic acid(s) are optionally present in an expression cassette and/or a vector and are optionally labeled with a detectable label. Also provided are host cells comprising such vectors and a process producing a polypeptide comprising expressing from such host cells a polypeptide encoded an MT-SP1 DNA. This invention also includes a process for producing a cell that expresses an MT-SP1 polypeptide. The process involves comprising transforming or transfecting the cell with the vector encoding an MT-SP1 such that the cell expresses the MT-SP1 polypeptide.

In another embodiment this invention provides isolated MT-SP1 polypeptides (e.g. as encoded by the nucleic acids described above). Preferred polypeptides comprise a protease domain of SEQ ID NO: 2 or the polypeptide of SEQ ID NO: 2. Preferred polypeptides also include, but are not limited to polypeptides that have serine protease activity and that are specifically bound by an antibody raised against the polypeptide of SEQ ID NO: 2 and/or polypeptides having protease activity and having 95% or greater sequence identity to a polypeptide having the sequence of SEQ ID NO: 2; and/or having protease activity and having 95% or greater identity to a polypeptide having the sequence of amino acids 615 through 855 of SEQ ID NO: 2.

Also provided are antibodies that specifically bind to the MT-SP1 polypeptides of this invention (e.g. a polypeptide encoded by SEQ ID NO: 2). The antibodies can be monoclonal, polyclonal, antibody fragments or single-chain antibodies.

This invention also provides diagnostic assays for cancer(s). Such assays involve providing a biological sample from an organism; and detecting the level of a membrane type serine protease 1 (MT-SP1) in the sample, where an elevated level of the membrane-type serine protease, as compared to the level of the protease in a biological sample from a normal healthy organism indicates the presence of the cancer. The method can involve determining the copy number of MT-SP1 genes in the cells of the biological sample (e.g. using FISH or Comparative Genomic Hybridization (CGH)). In another embodiment, the method can involve measuring the level of MT-SP1 mRNA in the biological sample, wherein an increased level of MT-SP1 RNA in the sample compared to MT-SP1 RNA in a control sample indicates the presence (or significant probability of the presence) of the cancer. The mRNA determination can involve hybridizing (e.g. using a Northern blot, a Southern blot, an array hybridization, an affinity chromatography, an in situ hybridization, etc.) the mRNA to one or more probes that specifically hybridize (under stringent conditions) to a nucleic acid encoding the MT-SP1 protein. A probe used in such measurements can optionally include a plurality of probes that form an array of probes. Preferred detection methods involve quantifying MT-SP1 mRNA. In still another embodiment, the level of MT-SP1 mRNA is measured using a nucleic acid amplification reaction. In addition, or alternatively, the method can involve determining the level (e.g. via a method selected from the group consisting of capillary electrophoresis, a Western blot, mass spectroscopy, ELISA, immunochromatography, and immunohistochemistry) or activity of an MT-SP1 protein in the biological sample. Preferred biological samples for these assays include, but are not limited to excised tissue, whole blood, serum, plasma, buccal scrape, saliva, cerebrospinal fluid, and urine.

In certain embodiments, it is desired to pre-screen test agents for the ability to bind to an MT-SP1 nucleic acid and/or protein. Such pre-screening methods typically involve (a) contacting a nucleic acid encoding an MT-SP1 serine protease or an MT-SP1 serine protease protein with a test agent; and (b) detecting specific binding of the test agent to the MT-SP1 protein or nucleic acid. Preferred test agents do not include antibodies, and/or nucleic acids. In particularly preferred assay formats the MT-SP1 nucleic acid and/or protein is immobilized on a solid support, while in other preferred assay formats, the test agent is immobilized (e.g. in a 96 well plate, etc.). Preferred methods of detecting binding utilize detectable labels (e.g. fluorescent labels) and a particular preferred detection methods utilizes fluorescent resonance energy transfer (FRET).

MT-SP1 levels are also good prognostic indicators for various cancers as described herein. This invention therefore also provides methods (prognostic assays) for evaluating the severity or outcome of a cancer (e.g. for estimating length of survival of a cancer patient). The methods preferably involve (a) obtaining a biological sample from a cancer patient having at least a preliminary diagnosis of cancer; (b) measuring MT-SP1 in said sample and comparing the sample MT-SP1 level to the MT-SP1 level in normal healthy humans wherein a sample MT-SP1 level in excess of MT-SP1 levels in normal healthy humans indicates a reduced survival expectancy compared to patients with normal MT-SP1 level. Particular embodiments include a preliminary diagnosis of prostate cancer, a cancer of the digestive tract, a breast cancer, and/or a urogential cancer. Preferred biological samples, include, but are not limited to a primary tumor or a tissue affected by the cancer (e.g. a tumor biopsy)

and/or samples selected from the group consisting of whole blood, plasma, serum, synovial fluid, cerebrospinal fluid, bronchial lavage, ascites fluid, bone marrow aspirate, pleural effusion, urine, or tumor tissue. As indicated above, MT-SP1 can be evaluated by copy number of MT-SP1 genomic DNA, MT-SP1 mRNA levels, levels of nucleic acid(s) derived from MT-SP1 mRNA (e.g. cDNAs, RT-PCR products, etc.), MT-SP1 protein levels and/or MT-SP1 activity levels. In a preferred embodiments the level of MT-SP1 is measured by immunohistochemical staining of cells comprising the biological sample (e.g. tumor tissue cells) and/or via an immunoassay (e.g., ELISA using an anti-MT-SP1 antibody as described above).

Also provided are methods of treating a cancer in a patient. The methods involve performing one or more of the prognostic assays described herein on a cancer patient having at least a preliminary diagnosis of a cancer; and (c) selecting a patient identified with an MT-SP1 level excess of MT-SP1 levels in normal healthy humans and providing an adjuvant cancer therapy (e.g. a therapy selected from the group consisting of chemotherapy, radiation therapy, reoperation, antihormone therapy, and immunotherapy).

This invention also affords methods of screening for recurrence of a cancer after removal of a primary tumor. These methods involve performing one or more of the assays described herein on a biological sample from a cancer patient following removal of a primary tumor. The assay can be repeated at a multiplicity of instances after removal of the primary tumor.

Similarly the assays of this invention provide methods of monitoring the effectiveness of cancer treatment in patients. This involves obtaining a first biological sample from said patient prior to or following one or more treatments of a cancer; obtaining a second biological sample from said cancer patient during or after said one or more treatments; evaluating the samples for MT-SP1 level as described herein where a lower level of MT-SP1 in the second sample as compared to the MT-SP1 level in the first sample indicates efficacy of the treatment(s). Typically the treatments involve chemotherapy, radiation therapy, immunotherapy, anti hormone therapy, or surgery.

It was also a discovery of this invention that MT-SP1 provides a good target for specifically delivering an effector (e.g. a liposome, a cytotoxin, a detectable label) to a cell (e.g. a tumor cell) expressing MT-SP1. The methods involve providing a chimeric moiety comprising an effector (e.g. an effector molecule) attached to an anti-MT-SP1 antibody; and contacting the cell with said chimeric moiety whereby the chimeric moiety binds (e.g. specifically binds) to the "target" cell. In preferred embodiments, the cell (e.g. tumor cell) internalizes at least a portion (e.g. a detectable or measurable amount) of the molecule. Preferred cells include cancer cells, e.g., cells from a prostate cancer, a cancer of the digestive tract, a breast cancer, and a urogential cancer. Preferred effectors include a cytotoxin, a detectable label, a radionuclide, a drug, a liposome, a ligand, and an antibody. In particularly preferred embodiments, the chimeric moiety is a fusion protein. Preferred fusion proteins include effectors selected from the group consisting of ricin, abrin, *Diphtheria* toxin, and *Pseudomonas* exotoxin. In other preferred embodiments, the effector is cytotoxic and/or a liposome comprising an anti-cancer drug (e.g. doxirubicin, vinblastine, vincristine, taxol, doxirubicin, and genistein).

This invention also provides chimeric moieties (e.g. chimeric molecules) comprising an effector attached to an anti-MT-SP1 antibody. Preferred effectors include cytotoxin, a detectable label, a radionuclide, a drug, a liposome, a ligand, and an antibody. Preferred chimeric moieties are fusion proteins and particularly preferred fusion proteins have cytotoxic effectors (e.g., ricin, abrin, *Diphtheria* toxin, *Pseudomonas* exotoxin, etc.). Other preferred effectors include a liposome comprising an anti-cancer drug as described above. The chimeric moieties described herein can be formulated as pharmaceutical compositions comprising the chimeric moiety and pharmaceutically acceptable excipient.

This invention also provides methods of impairing growth of tumor cells expressing an MT-SP1 protein. The methods comprise contacting the tumor cells with a chimeric molecule comprising an anti-MT-SP1 antibody; and a cytotoxic effector as described herein.

Definitions

The term "nucleic acid" refers to a deoxyribonucleotide or ribonucleotide polymer in either single- or double-stranded form, and unless otherwise limited, encompasses known analogs of natural nucleotides that can function in a similar manner as naturally occurring nucleotides.

A "nucleic acid derived from an mRNA transcript" or "nucleic acid derived from an MT-SP1 gene" refers to a nucleic acid for whose synthesis the mRNA transcript or a subsequence thereof or the MT-SP1 gene or subsequence thereof has ultimately served as a template. Thus, a cDNA reverse transcribed from an mRNA, an RNA transcribed from that cDNA, a DNA amplified from the cDNA, an RNA transcribed from the amplified DNA, etc., are all derived from the mRNA transcript and detection of such derived products is indicative of the presence and/or abundance of the original transcript in a sample. Thus, suitable samples include, but are not limited to, mRNA transcripts of the gene or genes, cDNA reverse transcribed from the mRNA, cRNA transcribed from the cDNA, DNA amplified from the genes, RNA transcribed from amplified DNA, and the like.

The terms "isolated" "purified" or "biologically pure" refer to material which is substantially or essentially free from components which normally accompany it as found in its native state.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

An amino acid, identified by name herein "e.g., arginine" or "arginine residue" as used herein refers to natural, synthetic, or version of the amino acids. Thus, for example, an arginine can also include arginine analogs that offer the same or similar functionality as natural arginine with respect to their ability of be incorporated into a polypeptide, effect folding of that polypeptide and effect interactions of that polypeptide with other polypeptide(s).

The phrase "nucleic acid encoding" or "nucleic acid sequence encoding" refers to a nucleic acid that directs the expression of a specific protein or peptide. The nucleic acid sequences include both the DNA strand sequence that is transcribed into RNA and the RNA sequence that is translated into protein. The nucleic acid sequences include both full-length nucleic acid sequences as well as shorter sequences derived from the full-length sequences. It is understood that a particular nucleic acid sequence includes the degenerate codons of the native sequence or sequences which may be introduced to provide codon preference in a specific host cell. The nucleic acid includes both the sense and antisense strands as either individual single strands or in the duplex form.

The term "MT-SP1" protease, as used herein refers to either the membrane type serine protease exemplified (e.g. by SEQ ID NOs: 1 and 2) or to the class of serine proteases characterized by the presence of a non-cleaved signal/anchor domain that anchors the serine protease in the cell membrane (see, e.g., Parks & Lamb (1991) *Cell* 64: 777–787; Parks & Lamb (193) *J. Biol. Chem.*, 268: 19101–19109). Typically, charged residues flank the sides of the signal/anchor domain was analyzed. Charged residues on the N-terminal side of the signal/anchor are important for proper topology, while addition of charges to the C-terminal side of the signal/anchor has little effect upon orientation. Removal of any of the positive charges preceding the signal anchor led to partial inversion of the topology, suggesting that each positive charge contributes to the signal. These results indicate that a type II membrane protein is characterized by a protein that lacks a cleavable signal sequence (1) and has positively charged residues on the N-terminal side of a long stretch of hydrophobic amino acids (see, e.g., Walter and Lingappa (1986) *Annu. Rev. Cell Biol.* 2: 499–516).

The term "mutation", when used in reference to a polypeptide refers to the change of one or more amino acid residues in a polypeptide to residues other than those found in the "native" or "reference (pre-mutation) form of that polypeptide. Mutations include amino acid substitutions as well as insertions and/or deletions. A mutation does not require that the particular amino acid substitution or deletion be made to an already formed polypeptide, but contemplates that the "mutated" polypeptide can be synthesized de novo, e.g. through chemical synthesis or recombinant means. It will be appreciated that the mutation can include replacement of a natural amino acid with an "unnatural" amino acid.

The term "prognostic" or "prognostic assay" refers to an assay that provides an indication as to the outcome of a disease. A prognostic assay need not indicate the presence or absence of a disease. A negative prognostic assay might indicate the need for a more aggressive therapeutic regimen.

A "protease" is a polypeptide that cleaves another polypeptide at a particular site (amino acid sequence). The protease can also be self-cleaving.

A protease is said to be "specific" for another polypeptide when it characteristically cleaves the other "substrate" polypeptide at a particular amino acid sequence. The specificity can be absolute or partial (i.e., a preference for a particular amino acid or amino acid sequence).

The term "specifically binds" when used to refer to binding proteins herein indicates that the binding preference (e.g., affinity for the target molecule/sequence is at least 2 fold, more preferably at least 5 fold, and most preferably at least 10 or 20 fold over a non-specific (e.g. randomly generated molecule lacking the specifically recognized amino acid or amino acid sequence) target molecule.

The term "phage", when used in the context of polypeptide display, includes bacteriophage as well as other "infective viruses", e.g. viruses capable of infecting a mammalian, or other, cell.

The term "chymotrypsin fold" refers to the anti-parallel beta barrel protein "fold" characteristic of trypsin, chymotrypsin, elastase, and related serine proteases (see, e.g., Branden and Tooze (1991) *Introduction to Protein Structure*, Garland Publishing, New York; Creighton (1993) Proteins, 2nd edition, W.H. Freeman & Co., New York; Schulz and Schirmer (1979) *Principles of Protein Structure*, Springer-Verlag, New York; Perutz (1992) *Protein Structure—New Approaches to Disease and Therapy*, W.H. Freeman & Co., New York; Fersht (1976) *Enzyme Structure and Mechanism*, 2nd ed., W.H. Freeman & Co., New York).

A "protease substrate" is a polypeptide that is specifically recognized and cleaved by a protease.

The term "modulate" when used with respect to protease activity refers to an alteration in the rate of reaction (protein hydrolysis) catalyzed by a protease. An increase in protease activity results in an increase in the rate of substrate hydrolysis at a particular protease concentration and a protease modulator that produces such an increase in protease activity is referred to as an "activator" or "protease agonist". The terms "activator" or "agonist" are thus used synonymously. A decrease in protease activity refers to a decrease in the rate of substrate hydrolysis at a particular protease concentration. Such a decrease may involve total elimination of protease activity. A protease modulator that produces a decrease in protease activity is referred to as a "protease inhibitor". It will be appreciated that generally the increase or decrease is as compared to the protease absent the protease modulator.

The term "antibody" refers to a polypeptide substantially encoded by an immunoglobulin gene or immunoglobulin genes, or fragments thereof which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. An exemplary immunoglobulin (antibody) structural unit comprises a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially an Fab with part of the hinge region (see, Fundamental Immunology, Third Edition, W. E. Paul, ed., Raven Press, N.Y. 1993). While various antibody fragments are defined in terms of the digestion of an intact antibody, one of skill will appreciate that such fragments may be synthesized de novo either chemically or by utilizing recombinant DNA methodology. Thus, the term antibody, as used herein, also includes antibody fragments either produced by the modification of whole antibodies, those synthesized de novo using recombinant DNA methodologies (e.g., single chain Fv), and those found in display libraries (e.g. phage display libraries).

The phrases "hybridizing specifically to" or "specific hybridization" or "selectively hybridize to", refer to the binding, duplexing, or hybridizing of a nucleic acid molecule preferentially to a particular nucleotide sequence under stringent conditions when that sequence is present in a complex mixture (e.g., total cellular) DNA or RNA.

The term "stringent conditions" refers to conditions under which a probe will hybridize preferentially to its target subsequence, and to a lesser extent to, or not at all to, other sequences. "Stringent hybridization" and "stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993) *Laboratory Techniques in Biochemistry and Molecular Biology—Hybridization with Nucleic Acid Probes* part I chapter 2 *Overview of principles of hybridization and the strategy of nucleic acid probe assays*, Elsevier, N.Y. Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe.

An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see, Sambrook et al. (1989) *Molecular Cloning—A Laboratory Manual* (2nd ed.) Vol. 1–3, Cold Spring Harbor Laboratory, Cold Spring Harbor Press, NY, (Sambrook et al.) supra for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4–6×SSC at 40° C. for 15 minutes. In general, a signal to noise ratio of 2× (or higher) than that observed for an unrelated probe in the particular hybridization assay indicates detection of a specific hybridization. Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

In one particularly preferred embodiment, stringent conditions are characterized by hybridization in 1 M NaCl, 10 mM Tris-HCl, pH 8.0, 0.01% Triton X-100, 0.1 mg/ml fragmented herring sperm DNA with hybridization at 45° C. with rotation at 50 RPM followed by washing first in 0.9 M NaCl, 0.06 M NaH$_2$PO$_4$, 0.006 M EDTA, 0.01% Tween-20 at 45° C. for 1 hr, followed by 0.075 M NaCl, 0.005 M NaH$_2$PO$_4$, 0.5 mM EDTA at 45° C. for 15 minutes.

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or polypeptides, refers to two or more sequences or subsequences that have at least 60%, preferably 80%, most preferably 90–95% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman (1988) *Proc. Natl. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle (1987) *J. Mol. Evol.* 35:351–360. The method used is similar to the method described by Higgins & Sharp (1989) *CABIOS* 5:151–153. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described in Altschul et al. (1990) *J. Mol. Biol.* 215: 403–410. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N. (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul (1993) *Proc. Natl. Acad. Sci. USA,* 90: 5873–5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

The term "biological sample" refers to sample is a sample of biological tissue, cells, or fluid that, in a healthy and/or pathological state, contains a nucleic acid or polypeptide that is to be detected according to the assays described herein. Such samples include, but are not limited to, cultured cells, primary cell preparations, sputum, amniotic fluid, blood, tissue or fine needle biopsy samples, urine, peritoneal fluid, and pleural fluid, or cells therefrom. Biological samples may also include sections of tissues (e.g, frozen sections taken for histological purposes). Although the sample is typically taken from a human patient, the assays can be used to detect MT-SP1 in samples from any mammal, such as dogs, cats, sheep, cattle, and pigs, etc. The sample may be pretreated as necessary by dilution in an appropriate buffer solution or concentrated, if desired. Any of a number of standard aqueous buffer solutions, employing one of a variety of buffers, such as phosphate, Tris, or the like, at physiological pH can be used.

The term "test agent" refers to an agent that is to be screened in one or more of the assays described herein. The agent can be virtually any chemical compound. It can exist as a single isolated compound or can be a member of a chemical (e.g. combinatorial) library. In a particularly preferred embodiment, the test agent will be a small organic molecule.

The term "effector" molecule refers to one or more molecules comprising a "chimeric molecule or chimeric moiety" whose "activity" it is desired to deliver (into, adjacent to or in the proximity of) a target cell or cells. The activity need not be activity on the cell, but can simply provide a property (e.g. detectability by x-rays, elevated radiosensitivity, etc.) not normally present at or in the cell. The effector while often a single molecule also encompases multi-molecular entities (e.g. liposomes containing drugs, etc.). It is also recognized that one or more anti-MT-SP1 antibodies may be attached to any effector or, conversely, one or more effectors can be attached to a single MT-SP1 antibody.

The term "anti-cancer" drug is used herein to refer to one or a combination of drugs conventionally used to treat cancer. Such drugs are well known to those of skill in the art and include, but are not limited to doxirubicin, vinblastine, vincristine, taxol, etc.

The term "small organic molecules" refers to molecules of a size comparable to those organic molecules generally used in pharmaceuticals. The term excludes biological macromolecules (e.g., proteins, nucleic acids, etc.). Preferred small organic molecules range in size up to about 5000 Da, more preferably up to 2000 Da, and most preferably up to about 1000 Da.

The term "conservative substitution" is used in reference to proteins or peptides to reflect amino acid substitutions that do not substantially alter the activity (specificity or binding affinity) of the molecule. Typically conservative amino acid substitutions involve substitution one amino acid for another amino acid with similar chemical properties (e.g. charge or hydrophobicity). The following six groups each contain amino acids that are typical conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W).

BRIEF DESCRIPTION OF THE DRAWINGS

FIG. 1 shows the nucleotide sequence of the cDNA encoding human MT-SP1 (SEQ ID NO: 1) and predicted protein sequence (SEQ ID NO: 2). Numbering indicates nucleotide or amino acid residue. Amino acids are shown in single-letter code. The termination codon is shown by an asterisk (*). The underlined stop codon at nucleotide 10 is in frame with the initiating methionine. The Kozak consensus sequence (Kozak (1991) *J. Cell Biol.* 115: 887–903) at the start codon is underlined at nucleotide 32. The predicted N-glycosylation sites at amino acids 109, 302, 485, and 772 are underlined. A possible polyadenylation sequence (Nevins (1983) *Ann. Rev. Biochem.* 52: 441–466) at nucleotide 3120 is also underlined. The catalytic triad in the serine protease domain is highlighted: His656, Asp711 and Ser805.

FIGS. 4A, 4B, and 4C show multiple sequence alignments of MT-SP1 structural motifs. L represent loops, □ represent beta sheets, □ represent alpha helices, and S—S represent disulfides. FIG. 4A shows multiple sequence alignment of the serine protease domain of MT-SP1 with human trypsinogen B (Emi et al. (1986) *Gene* 41: 305–310), human enterokinase (Kitamoto et al. (1995) *Biochemistry* 34: 4562–4568), human hepsin (Leytus et al. (1988) *Biochemistry* 27: 1067–1074), human tryptase 2 (Vanderslice et al. (1990) *Proc. Natl. Acad. Sci. USA* 87: 3811–3815), and human chymotrypsinogen B (Tomita et al. (1989) *Biochem. Biophys. Res. Commun.* 158: 569–575), using standard chymotrypsin numbering. Conserved catalytic and structural residues described in the text are underlined. FIG. 4B shows alignment of MT-SP1 LDLR with domains of the LDL receptor (Sudhof et al. (1985) *Science* 228: 815–822). FIG. 4C shows alignment of the CUB domains of MT-SP1 with those found in human enterokinase (Kitamoto et al. (1995) *Biochemistry* 34: 4562–4568), human bone morphogenetic protein 1 (Wozney et al. (1988) *Science* 242: 1528–1534), and complement component C1R (Leytus et al. (1986) *Biochemistry* 25: 4855–4863).

FIGS. 5A and 5B show the tissue distribution of MT-SP1 mRNA levels. Northern blots of human poly(A)+ RNA from assorted human tissues was hybridized with radiolabeled cDNA probes as described under Materials and Methods. The upper panel shows hybridization using a MT-SP1 1.3 kB cDNA fragment derived from EST clone w39209 and exposed overnight. The lower panel shows the same blot after being stripped and rehybridized with a loading standard (FIG. 5A) β-actin or (FIG. 5B) human glyceraldehyde phosphate dehydrogenase (GAPDH) cDNA probe exposed for two hours. The mobility of RNA size standards are indicated at the left.

FIG. 6A: Activation at 4° C. is monitored using SDS-PAGE. The upper band represents inactivated protease domain, and the lower band represents active protease (also verified by N-terminal sequencing). FIG. 6B: The activation of the protein was monitored using hexahydrotyrosyl-glycyl-arginyl-paranitroanilide as a synthetic substrate for the protease domain.

DETAILED DESCRIPTION

Figure 2:
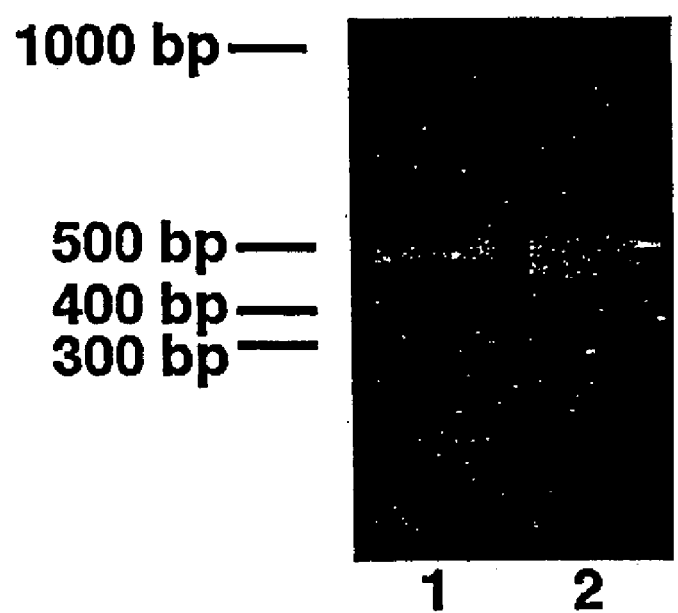
FIG. 2, lane 1 shows the PCR products obtained using degenerate primers designed from the consensus sequences flanking the catalytic histidine (5' His-primer) and the catalytic serine (3' Ser-primer). The products remaining between 400 and 550 bp after digestion with BamHI were reamplified using the same degenerate primers. The products from this second PCR are shown in lane 2.

This invention pertains to the discovery of novel membrane-type serine proteases whose inhibition results in inhibition of mouse and rat prostate differentiation and the retardation of growth of human PC-3 TRAMP prostatic cancer cells. The prototypical protease of this invention is referred to herein as membrane-type serine protease 1 (MT-SP1).

The cloning and characterization of the MT-SP1 cDNA showed that it encodes a mosaic protein that contains a transmembrane signal anchor, two CUB domains, four LDLR repeats, and a serine protease domain. Northern blotting showed broad expression of MT-SP1 in a variety of epithelial tissues with high levels of expression in the human gastrointestinal tract and the prostate. In particular MT-SP1 showed significant expression in the endothelium of tumor blood vessels The data presented herein indicate that expression of the MT-SP1 membrane-type serine protease(s) are associated with the presence of, or proclivity to, cancer. In particular, without being bound to a theory, it is believed that the membrane-type serine protease MT-SP1 participates in a proteolytic cascade that results in cell growth and or differentiation. Another structurally similar membrane-type serine protease, enteropeptidase (FIG. 3), is involved in a proteolytic cascade by which activation of trypsinogen leads to activation of downstream intestinal proteases (Huber and Bode (1978) *Acc. Chem. Res.* 11: 114–122). Enteropeptidase is expressed only in the enterocytes of the proximal small intestine thus precisely restricting activation of trypsinogen. Thus, in contrast to secreted proteases that may diffuse throughout the organism, the membrane association of MT-SP1 allows the proteolytic activity to be precisely localized, which may is important for proper physiological function. Improper localization of the enzyme or levels of downstream substrates could lead to disease.

We have found subcutaneous coinjection of PC-3 cells with wild-type ecotin or ecotin M84R/M85R led to a decrease in the primary tumor size compared to animals in whom PC-3 cells and saline were injected. Since wild-type ecotin is a poor, micromolar inhibitor of uPA, serine proteases other than uPA (e.g., an MT-SP1) are believed to be involved in this primary tumor proliferation. Both wild-type ecotin and ecotin M84R/M85R are potent, subnanomolar inhibitors of MT-SP1, strongly suggesting that MT-SP1 plays an important role in progression of epithelial cancers expressing this protease.

In addition, MT-SP1 is associated with tumors (e.g. is a good tumor marker). In particular, immunohistochemical examination of gastric cancer tissue revealed MT-SP1 expression in cancer cells, endothelial cells and some leukocytes. In these tissues, endothelial cells showed especially intensive MT-SP1 immunoreactivity indicating that MT-SP1 might play an important role in vascular cells particularly in angiogenesis of tumor and tumor-related blood vessels.

In addition, overall survival for groups of gastric carcinoma patients with highly MT-SP1 expressing endothelium revealed poor prognosis compared to those with low or no MT-SP1. Higher MT-SP1 expression in endothelium was significantly associated with lower survival rate.

MT-SP1 thus appears to be a good diagnostic, prognostic, or therapeutic target. In one embodiment, this invention therefore provides methods of screening for (e.g. diagnosing) the presence or absence of a cancer by detecting the level of MT-SP1 expression and/or activity. In a particularly preferred embodiment this invention provides methods of screening for (e.g. diagnosing) the presence of a metastatic cell.

In another embodiment, this invention provides prognostic methods, e.g., methods of estimating length of survival of a cancer patient, or evaluating the severity of disease or the likilihood of disease recurrence in a cancer patient. These methods also involve determining the level of MT-SP1 expression and/or activity, where higher expression levels indicate greater disease severity, poorer outcome or greater liklihood of disease recurrence.

MT-SP1 also provides a convenient diagnostic tag for localizing a tumor or cancer cell. This involves providing anti-MT-SP1 antibodies attached to a detectable tag (e.g. radioactive or radiopaque tage). The labeled MT-SP1 antibody will localize on the surface of tumor cells expressing MT-SP1 and detection of the tag provides an indication fo the presence, locality, and size of the cancer.

Having identified a novel protease involved with the etiology of cancers, particularly invasive cancers, the MT-SP1 DNA, mRNA, and protein product provide good targets for the action of putative modulators. This invention thus, also provides methods of screening for modulators of MT-SP1 expression and/or activity. In addition simple binding assays can be used to identify agents (e.g. small organic molecules, antisense molecules, ribozymes, antibodies, etc.) that interact specifically with the MT-SP1 nucleic acids and/or proteins. Screening agents for such specific binders identifies putative agents likely to modulate MT-SP1 expression and/or activity. Collections of such agents provide "biases" molecular libraries that are useful candidates for a variety of screening systems.

The localization of MT-SP1 in tumors, and in particular, on vascular endothelial cells associated with tumors provides a convenient method for specifically delivering an effector (e.g. an effector molecule) to such cells. The method involves attaching one or more molecules that specifically bind to MT-SP1 (e.g. an anti-MT-SP1 antibody) to the effector it is desired to deliver and administering the composition to the subject (e.g. intraperioneally, intravenously, direct injection into tumor site, etc.). The chimeric antibody-effector composition will localize at the tumor site or on cells (e.g. tumor or metastatic cells expressing MT-SP1).

This invention also provides MT-SP1 nucleic acids and isolated (e.g. recombinantly expressed) proteins. Such isolated proteins are useful specific proteases in their own right. In addition they can be used to help "dissect" metabolic pathways and/or can be used as effective immunogens to raise anti-MT-SP1 antibodies.

I. Nucleic Acids Encoding Membrane-Type Serine Proteases.

Using the information provided herein, (e.g. MT-SP1 cDNA sequence, primers, etc.) the nucleic acids (e.g., encoding full length MT-SP1 or MT-SP1 proteolytic domain or other subsequences of the MT-SP1 cDNA, genomic DNA, mRNA, etc) are prepared using standard methods well known to those of skill in the art. For example, the MT-SP1 nucleic acid(s) may be cloned, or amplified by in vitro methods, such as the polymerase chain reaction (PCR), the ligase chain reaction (LCR), the transcription-based amplification system (TAS), the self-sustained sequence replication system (SSR), etc. A wide variety of cloning and in vitro amplification methodologies are well-known to persons of skill. Examples of these techniques and instructions sufficient to direct persons of skill through many cloning exercises are found in Berger and Kimmel, *Guide to Molecular Cloning Techniques, Methods in Enzymology* 152 Academic Press, Inc., San Diego, Calif. (Berger); Sambrook et al. (1989) *Molecular Cloning—A Laboratory Manual* (2nd ed.) Vol. 1–3, Cold Spring Harbor Laboratory, Cold Spring Harbor Press, NY, (Sambrook et al.); *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel); Cashion et al., U.S. Pat. No. 5,017, 478; and Carr, European Patent No. 0,246,864. Examples of techniques sufficient to direct persons of skill through in vitro amplification methods are found in Berger, Sambrook, and Ausubel, as well as Mullis et al., (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36–47; *The Journal Of NIH Research* (1991) 3: 81–94; (Kwoh et al. (1989) *Proc. Natl. Acad. Sci. USA* 86: 1173; Guatelli et al. (1990) *Proc. Natl. Acad. Sci. USA* 87, 1874; Lomell et al. (1989) *J. Clin. Chem.*, 35: 1826; Landegren et al., (1988) *Science*, 241: 1077–1080; Van Brunt (1990) *Biotechnology*, 8: 291–294; Wu and Wallace, (1989) *Gene*, 4: 560; and Barringer et al. (1990) *Gene*, 89: 117.

The isolation and expression of an MT-SP1 nucleic acid is illustrated in Example 1. In one preferred embodiment, the MT-SP1 cDNA can be isolated by routine cloning methods. The cDNA sequence provided in SEQ ID NO: 1 can be used to provide probes that specifically hybridize to the MT-SP1 gene, in a genomic DNA sample, or to the MT-SP1 mRNA, in a total RNA sample (e.g., in a Southern blot). Once the target MT-SP1 nucleic acid is identified (e.g., in a Southern blot), it can be isolated according to standard methods known to those of skill in the art (see, e.g., Sambrook et al. (1989) *Molecular. Cloning: A Laboratory Manual, 2nd Ed., Vols.* 1–3, Cold Spring Harbor Laboratory; Berger and Kimmel (1987) *Methods in Enzymology*, Vol. 152: *Guide to Molecular Cloning Techniques*, San Diego: Academic Press, Inc.; or Ausubel et al. (1987) *Current Protocols in Molecular Biology*, Greene Publishing and Wiley-Interscience, New York). Methods of screening human cDNA libraries for the MT-SP1 are provided in Example 1.

Figure 1:
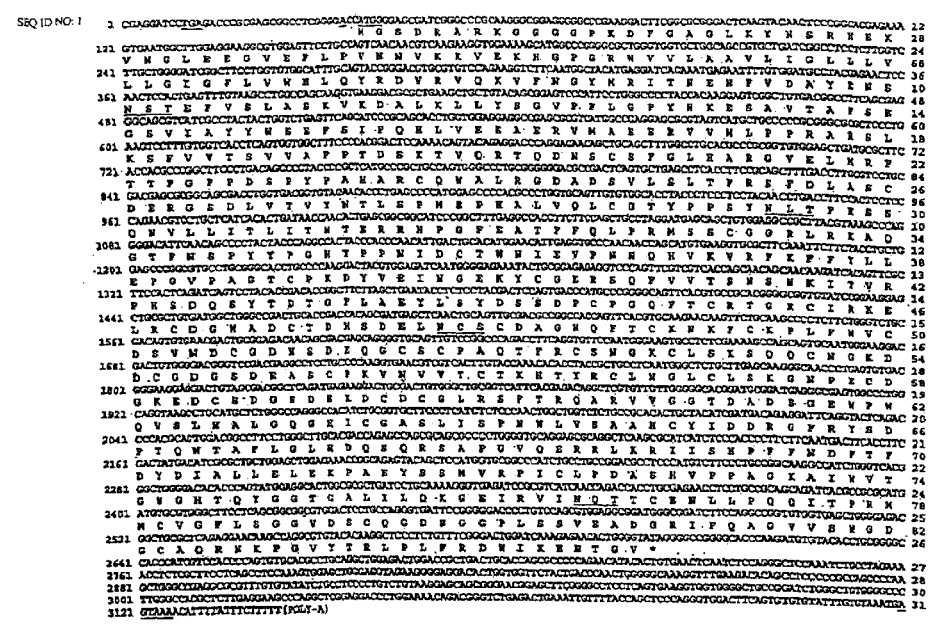

In another preferred embodiment, the human MT-SP1 cDNA can be isolated by amplification methods such as polymerase chain reaction (PCR). In a preferred embodiment, the MT-SP1 sequence is amplified from a cDNA sample (e.g., double stranded placental cDNA (Clontech)) using the primers routinely derived from the sequence illustrated in FIG. 1 (SEQ. ID NO: 1). Preferred primers are primer 1, nucleotides 37–54 of SEQ ID NO: 1) and primer 2, nucleotides 2604–2583 of the complement of SEQ ID NO: 1. Preferred amplification conditions include 30 cycles of 1 minute denaturing at 94° C., 1-minute annealing at 54° C., 3 minutes of extension at 72° C., folowed by a final 15 minute extension at 72° C. Preferred template includes full length PCIII cDNA.

Where the MT-SP1 gDNA, cDNA, mRNA or their subsequences are to be used as nucleic acid probes, it is often desirable to label the nucleic acids with detectable labels. The labels may be incorporated by any of a number of means well known to those of skill in the art. However, in one preferred embodiment, the label is simultaneously incorporated during the amplification step in the preparation of the sample nucleic acids. Thus, for example, polymerase chain reaction (PCR) with labeled primers or labeled nucleotides will provide a labeled amplification product. In another preferred embodiment, transcription amplification using a labeled nucleotide (e.g. fluorescein-labeled UTP and/or CTP) incorporates a label into the transcribed nucleic acids.

Alternatively, a label may be added directly to an original nucleic acid sample (e.g., mRNA, polyA mRNA, cDNA, etc.) or to the amplification product after the amplification is completed. Means of attaching labels to nucleic acids are well known to those of skill in the art and include, for example nick translation or end-labeling (e.g. with a labeled RNA) by kinasing of the nucleic acid and subsequent attachment (ligation) of a nucleic acid linker joining the sample nucleic acid to a label (e.g., a fluorophore). Suitable labels are described below.

II. Cloning and Expression of Membrane-Type Serine Proteases.

It is often desirable to provide isolated membrane-type serine proteases of this invention (e.g., MT-SP1). These polypeptides can be used to raise an immune response and thereby generate antibodies specific to the intact MT-SP1 or to various subsequences or domains thereof. As explained below, the MT-SP1 polypeptides and various fragments thereof can be conveniently produced using synthetic chemical syntheses or recombinant expression methodologies. In addition to the intact full-length MT-SP1 polypeptide, in some embodiments, it is often desirably to express immunogenically relevant fragments (e.g. fragments that can be used to raise specific anti-MT-SP1 antibodies). In other preferred embodiments, the protein is expressed as an inactive form (a zymogen or pro-enzyme) that is activated, e.g. via autocleavage, or alternatively, the enzymatic (proteolytic) domain can be expressed alone.

A) De Novo Chemical Synthesis.

The MT-SP1 serine protease precursors, the catalytic domain (active protease), or other subsequences of the MT-SP1 polypeptide(s) may be synthesized using standard chemical peptide synthesis techniques. Where the desired subsequences are relatively short (e.g., when a particular antigenic determinant is desired) the molecule may be synthesized as a single contiguous polypeptide. Where larger molecules are desired, subsequences can be synthesized separately (in one or more units) and then fused by condensation of the amino terminus of one molecule with the carboxyl terminus of the other molecule thereby forming a peptide bond.

Solid phase synthesis in which the C-terminal amino acid of the sequence is attached to an insoluble support followed by sequential addition of the remaining amino acids in the sequence is the preferred method for the chemical synthesis of the polypeptides of this invention. Techniques for solid phase synthesis are described by Barany and Merrifield, *Solid-Phase Peptide Synthesis*; pp. 3–284 in *The Peptides: Analysis, Synthesis, Biology. Vol. 2: Special Methods in Peptide Synthesis, Part A.*, Merrifield, et al. (1963) *J. Am. Chem. Soc.,* 85: 2149–2156, and Stewart et al. (1984) *Solid Phase Peptide Synthesis, 2nd ed.* Pierce Chem. Co., Rockford, Ill.

B) Recombinant Expression.

In a preferred embodiment, the MT-SP1 proteins or subsequences thereof (e.g. proteolytic domain), are synthesized using recombinant expression systems. Generally this involves creating a DNA sequence that encodes the desired protein, placing the DNA in an expression cassette under the control of a particular promoter, expressing the protein in a host, isolating the expressed protein and, if required, renaturing the protein.

DNA encoding the MT-SP1 proteins described herein can be prepared by any suitable method as described above, including, for example, cloning and restriction of appropriate sequences or direct chemical synthesis by methods such as the phosphotriester method of Narang et al. (1979) *Meth. Enzymol.* 68: 90–99; the phosphodiester method of Brown et al. (11979) *Meth. Enzymol.* 68: 109–151; the diethylphosphoramidite method of Beaucage et al. (1981) *Tetra. Lett.,* 22: 1859–1862; and the solid support method of U.S. Pat. No. 4,458,066.

Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences.

Alternatively, subsequences may be cloned and the appropriate subsequences cleaved using appropriate restriction enzymes. The fragments may then be ligated to produce the desired DNA sequence.

In one embodiment, the MT-SP1 nucleic acids of this invention can be cloned using DNA amplification methods such as polymerase chain reaction (PCR) (see, e.g., Example 1). Thus, for example, the nucleic acid sequence or subsequence is PCR amplified, using a sense primer containing one restriction site (e.g., NdeI) and an antisense primer containing another restriction site (e.g., HindIII). This will produce a nucleic acid encoding the desired MT-SP1 sequence or subsequence and having terminal restriction sites. This nucleic acid can then be easily ligated into a vector containing a nucleic acid encoding the second molecule and having the appropriate corresponding restriction sites. Suitable PCR primers can be determined by one of skill in the art using the sequence information provided in SEQ ID NOs:1 and 2 and representative primers are provided herein. Appropriate restriction sites can also be added to the nucleic acid encoding the MT-SP1 protein or protein subsequence by site-directed mutagenesis. The plasmid containing the MT-SP1 sequence or subsequence is cleaved with the appropriate restriction endonuclease and then ligated into the vector encoding the second molecule according to standard methods.

The nucleic acid sequences encoding MT-SP1 proteins or protein subsequences may be expressed in a variety of host cells, including *E. coli*, other bacterial hosts, yeast, and various higher eukaryotic cells such as the COS, CHO and HeLa cells lines and myeloma cell lines. The recombinant protein gene will be operably linked to appropriate expression control sequences for each host. For *E. coli* this includes a promoter such as the T7, trp, or lambda promoters, a ribosome binding site and preferably a transcription termination signal. For eukaryotic cells, the control sequences will include a promoter and often an enhancer (e.g., an enhancer derived from immunoglobulin genes, SV40, cytomegalovirus, etc.), and a polyadenylation sequence, and may include splice donor and acceptor sequences.

The plasmids of the invention can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant MT-SP1 protein(s) can be purified according to standard procedures of the art, including ammonium sulfate precipitation, affinity columns, column chromatography, gel electrophoresis and the like (see, generally, R. Scopes, (1982) *Protein Purification*, Springer-Verlag, N.Y.; Deutscher (1990) *Methods in Enzymology Vol.* 182: *Guide to Protein Purification.*, Academic Press, Inc. N.Y.). Substantially pure compositions of at least about 90 to 95% homogeneity are preferred, and 98 to 99% or more homogeneity are most preferred. Once purified, partially or to homogeneity as desired, the polypeptides may then be used (e.g., as immunogens for antibody production). The cloning and expression of a MT-SP1 polypeptides is illustrated in Example 1.

In a preferred embodiment, the MT-SP1 nucleic acid(s) are transformed into *E. coli* X-90 to afford high-level expression of recombinant protease gene products (Evnin et al. (1990) *Proc. Natl. Acad. Sci. USA* 87, 6659–6663). Expression and purification of the recombinant enzyme from solubilized inclusion bodies is performed according to the method of Unal et al. (1997) *J. Virol.* 71, 7030–7038.

One of skill in the art would recognize that after chemical synthesis, biological expression, or purification, the MT-SP1 protein(s) may possess a conformation substantially different than the native conformations of the constituent polypeptides. In this case, it may be necessary to denature and reduce the polypeptide and then to cause the polypeptide to re-fold into the preferred conformation. Methods of reducing and denaturing proteins and inducing re-folding are well known to those of skill in the art (see, e.g., Debinski et al. (1993) *J. Biol. Chem.*, 268: 14065–14070; Kreitman and Pastan (1993) *Bioconjug. Chem.*, 4: 581–585; and Buchner, et al., (1992) *Anal. Biochem.*, 205: 263–270). Debinski et al., for example, describes the denaturation and reduction of inclusion body proteins in guanidine-DTE. The protein is then refolded in a redox buffer containing oxidized glutathione and L-arginine.

One of skill would recognize that modifications can be made to the MT-SP1 proteins without diminishing their biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

III. Diagnostics/Prognostics—Assays of Membrane-Type Serine Protease Level or Activity.

A) Diagnostic Applications.

MT-SP1 provides an effective marker for the detection/diagnosis of a wide variety of cancers. Diagnosis of disease based on measured levels of MT-SP1 can be made by comparison to levels measured in a disease-free control group or background levels measured in a particular patient. The diagnosis can be confirmed by correlation of the assay results with other signs of disease known to those skilled in the clinical arts, such as the diagnostic standards for breast cancer, gastric cancer, prostate cancer, etc.

Because in certain instances serum MT-SP1 may stem from sources other than the tissue of interest, in certain embodiments, a sample is preferably taken from the tissue of interest. However, as described below, in many instances basic differential diagnosis allows identification of the pathology resulting in elevated serum MT-SP1.

Particularly for the diagnosis and monitoring of cancers (e.g., tumor metastasis), the preferred source for the assay sample will be blood or blood products (e.g. plasma and/or serum) and/or tissue biopsies. Those of ordinary skill in the art will be able to readily determine which assay sample source is most appropriate for use in diagnosis of a particular disease for which MT-SP1 is a marker.

The levels of MT-SP1 that are indicative of the development or amelioration of a particular cancer by disease and, to a lesser extent, by patient. Appropriate background MT-SP1 levels in particular tissues, pathologies, and patients or patient populations or control populations can be determined by routine screening according to standard methods well known to those of skill in the art.

For purposes of diagnosing the onset, progression, or amelioration of disease, variations in the levels of MT-SP1 of interest will be those which differ by a statistically significant level from the normal (i.e., healthy) population or from the level measured in the same individual at a different time, and which correlate to other clinical signs of disease occurrence and/or prognosis and/or amelioration known to those skilled in the clinical art pertaining to the disease of interest.

Thus, in general, any diagnosis or prognosis indicated by MT-SP1 measurements made according to the methods of the invention will be independently confirmed with reference to clinical manifestations of disease known to practitioners of ordinary skill in the clinical arts.

B) Prognostic Applications.

In prognostic applications, MT-SP1 levels are evaluated to estimate the risk of recurrence of a cancer and thereby provide information that facilitates the selection of treatment regimen. Without being bound to a particular theory, it is believed that tumors are heterogeneous (even within a particular tumor type, e.g. colorectal cancer) with respect to elevated expression of MT-SP1. Those tumor types resulting in elevated levels of MT-SP1 also show a high likelihood of recurrence, e.g. after removal of a primary tumor. Thus, measurement of MT-SP1 levels (before, during [i.e. in blood or tissues removed during surgery], or after primary tumor removal) provides a prognostic indication of the likelihood of tumor recurrence. Where pathologies show elevated MT-SP1 levels (e.g. as compared to those in normal healthy subjects) more aggressive adjunct therapies (e.g. chemotherapy and/or radiotherapy) may be indicated.

By way of further example, in gastric cancer stages III, IV, patients (n=30) with an MT-SP LI of 40% or higher had a significantly lower survival rate than those (n=11) without MT-SP1 expression in vascular cells of cancer tissues. In addition, overall survival for groups of gastric carcinoma patients with highly MT-SP1 expressing endothelium revealed poor prognosis compared to those with low or no MT-SP1. Higher MT-SP1 expression in endothelium was significantly associated with lower survival rate indicating that MT-SP1 expression in endothelium around cancer cells is an important prognostic factor in gastric cancer.

C) Evaluation of Treatment Efficacy.

The MT-SP1 markers of this invention can also be used to evaluate treatment efficacy (e.g. amelioration of one or more symptoms of a cancer). Where the amelioration of a disease (such as cancer) can be related to reduction in levels of MT-SP1, MT-SP1 levels in a biological assay sample taken from the patient (e.g., blood) can be measured before (for background) and during or after (e.g., at a designated time, periodically or randomly) the course of treatment. Because reductions in MT-SP1 levels may be transient, the assay will preferably be performed at regular intervals, (e.g., every 4 weeks, every 6 months, every year, etc.) closely before and after each treatment. Depending on the course of treatment, tumor load and other clinical variables, clinicians of ordinary skill in the art will be able to determine an appropriate schedule for performing the assay for diagnostic or disease/treatment monitoring purposes.

Such monitoring methods can provide useful information to guide a therapeutic regimen in a variety of contexts as explained below.

1) Checking for Recurrence of a Cancer.

In one embodiment, MT-SP1 is monitored simply to check for the possible recurrence of a cancer after the primary tumor has been removed. This method generally involves obtaining a biological sample from a cancer patient following removal of a primary tumor; and measuring the level of MT-SP1 in the sample. An elevated MT-SP1 level (e.g. as compared to the MT-SP1 level in normal healthy humans) indicates a possible recurrence of a cancer. Where patients have elevated MT-SP1 levels at the time of surgery, the subsequent MT-SP1 monitoring is most informative after a period of time sufficient to permit MT-SP1 levels to return to normal (e.g. about 3–4 weeks after surgery). Of course, monitoring can be performed earlier to initiate tracking of changes in MT-SP1 levels. Where the patient does not have an elevation in MT-SP1 at the time of surgery increased MT-SP1 levels at any time after surgery indicate possible recurrence of the cancer. Elevated vlevels can be evaluated relative to levels in normal healthy people, or relative to MT-SP1 baseline levels determined for the particular patient (e.g., prior to, during, or immediately after surgery).

2) Monitoring of Terminal Phase Patients.

In another embodiment, MT-SP1 monitoring can be used to monitor the effectiveness of cancer treatment in patients with elevated MT-SP1. Such monitoring is particularly useful in patients in the terminal phase where the cancer has already metastasized so that surgery will not completely eliminate the cancer. Such patients will still be treated with radiation, chemotherapy, etc, to give them additional months of survival (although in many cases no cure). Periodic measurement of MT-SP1 provides the clinician with a means of monitoring the progress of treatment.

3) Checking the Efficacy of Surgical Removal of a Primary Tumor.

In still another embodiment, MT-SP1 monitoring can be used to check for the effectiveness of surgical removal of a primary tumor, in those instances in which there is an elevation in MT-SP1 prior to surgery. Since our longitudinal study shows that removal of the primary tumor causes the elevated MT-SP1 levels to fall to normal, measurement of MT-SP1 in post operative blood (e.g., about 4 weeks after surgery) will reveal those instances in which surgery did not remove all of the primary tumor, affected lymph nodes, and any other metastasis sites.

D) Relevant Pathologies.

As indicated above, MT-SP1 provides an effective marker for detection and/or evaluation of prognosis of a wide variety of cancers including, but not limited to, gastric cancer, prostate cancer, cancers of the urinary tract, lung cancer, bronchus cancer, a colorectal cancer (cancer of the colon and/or rectum), breast cancer, pancreas cancer, brain or central nervous system cancer, peripheral nervous system cancer, esophageal cancer, cervical cancer, melanoma, uterine or endometrial cancer, cancer of the oral cavity or pharynx, liver cancer, kidney cancer, testes cancer, biliary tract cancer, small bowel and appendix cancer, salivary gland cancer, thyroid gland cancer, adrenal gland cancer, and sarcomas such as osteosarcoma, chondrosarcoma, liposarcoma, and malignant fibrous histiocytoma. In general, MT-SP1 is a particularly good marker for metastatic cancers.

E) Relevant Pathologies.

As indicated above, MT-SP1 provides an effective marker for detection and/or evaluation of prognosis of a wide variety of cancers including, but not limited to, gastric cancer, prostate cancer, cancers of the urinary tract, lung cancer, bronchus cancer, a colorectal cancer (cancer of the colon and/or rectum), breast cancer, pancreas cancer, brain or central nervous system cancer, peripheral nervous system cancer, esophageal cancer, cervical cancer, melanoma, uterine or endometrial cancer, cancer of the oral cavity or pharynx, liver cancer, kidney cancer, testes cancer, biliary tract cancer, small bowel and appendix cancer, salivary gland cancer, thyroid gland cancer, adrenal gland cancer, and sarcomas such as osteosarcoma, chondrosarcoma, liposarcoma, and malignant fibrous histiocytoma. In general, MT-SP1 is a particularly good marker for metastatic cancers.

IV. Assay Formats.

As indicated above, in one aspect, this invention is premised on the discovery that membrane-type serine proteases (e.g. MT-SP1) are associated with occurrence, growth, proliferation, invasiveness, and angiogenesis of cancers. Thus, in one embodiment, this invention provides methods of screening for cancers and/or evaluating the severity of a cancer and/or the likelihood of metastatic cells being present and/or developing and/or evaluating the prognosis of a cancer. The methods involve detecting the expression level and/or activity level of a membrane-type serine protease where elevated expression levels and/or elevated activity levels indicate the presence of a cancer and/or the presence of invasive cancer cells and/or increased severity of the disease. Thus, assays of copy number, expression level or level of activity of one or MT-SP1 genes provides useful diagnostic and/or prognostic information. Using the nucleic acid sequences and/or amino acid sequences provided herein copy number and/or activity level can be directly measured according to a number of different methods as described below. In particular, expression levels of a gene can be altered by changes in the copy number of the gene, and/or by changes in the transcription of the gene product (i.e. transcription of mRNA), and/or by changes in translation of the gene product (i.e. translation of the protein), and/or by post-translational modification(s) (e.g. protein folding, glycosylation, etc.). Thus useful assays of this invention include assaying for copy number, level of transcribed mRNA, level of translated protein, activity of translated protein, etc. Examples of such approaches are described below.

A) Sample Collection and Processing.

The MT-SP1 nucleic acid and/or protein is preferably quantified in a biological sample derived from a mammal (e.g., whole blood, plasma, serum, synovial fluid, cerebrospinal fluid, bronchial lavage, ascites fluid, bone marrow aspirate, pleural effusion, urine, or tumor tissue), more preferably from a human patient. Preferred biological samples inlcude sample(s) of biological tissue or fluid that contain MT-SP1 in a concentration that may be correlated with the presence and/or prognosis of a pathological state (e.g. a cancer). Particularly preferred biological samples include, but are not limited to whole blood, serum, plasma, synovial fluid, cerebrospinal fluid, bronchial lavage, ascites fluid, pleural effusion, bone marrow aspirate, urine, and tumor tissue.

The biological sample may be pretreated as necessary by dilution in an appropriate buffer solution or concentrated, if desired. Any of a number of standard aqueous buffer solutions, employing one of a variety of buffers, such as phosphate, Tris, or the like, at physiological pH can be used.

As indicated above, in a preferred embodiment, assays are performed using whole blood, serum, or plasma or in tissue biopsies and/or tissue sections. Obtaining and storing tissues, blood and/or blood products are well known to those of skill in the art. Typically blood is obtained by venipuncture. The blood may be diluted by the addition of buffers or other reagents well known to those of skill in the art and may be stored for up to 24 hours at 2–8° C., or at −20° C. or lower for longer periods, prior to measurement of YKL-40. In a particularly preferred embodiment, the blood or blood product (e.g. serum) is stored at −70° C. without preservative indefinitely.

B) Nucleic-Acid Based Assays.

1) Target Molecules.

As indicated above, MT-SP1 gene expression can be varied by changes in copy number of the gene and/or changes in the regulation of gene expression. Changes in copy number are most easily detected by direct changes in genomic DNA, while changes in expression level can be detected by measuring changes in mRNA and/or a nucleic acid derived from the mRNA (e.g. reverse-transcribed cDNA, etc.).

In order to measure the nucleic acid concentration in a sample, it is desirable to provide a nucleic acid sample for such analysis. In preferred embodiments the nucleic acid is found in or derived from a biological sample. The term "biological sample", as used herein, refers to a sample obtained from an organism or from components (e.g., cells) of an organism. The sample may be of any biological tissue or fluid. Frequently the sample will be a "clinical sample" which is a sample derived from a patient. Such samples include, but are not limited to, sputum, blood, tissue or fine needle biopsy samples, urine, peritoneal fluid, and pleural fluid, or cells therefrom. Biological samples may also include sections of tissues such as frozen sections taken for histological purposes.

The nucleic acid (either genomic DNA or mRNA) is, in certain preferred embodiments, isolated from the sample according to any of a number of methods well known to those of skill in the art. One of skill will appreciate that where alterations in the copy number of a gene are to be detected genomic DNA is preferably isolated. Conversely, where expression levels of a gene or genes are to be detected, preferably RNA (mRNA) is isolated.

Methods of isolating total mRNA are well known to those of skill in the art. For example, methods of isolation and purification of nucleic acids are described in detail in by Tijssen ed., (1993) Chapter 3 of *Laboratory Techniques in Biochemistry and Molecular Biology: Hybridization With Nucleic Acid Probes, Part I. Theory and Nucleic Acid Preparation*, Elsevier, N.Y. and Tijssen ed.

In a preferred embodiment, the "total" nucleic acid is isolated from a given sample using, for example, an acid guanidinium-phenol-chloroform extraction method and polyA+ mRNA is isolated by oligo dT column chromatography or by using (dT)n magnetic beads (see, e.g., Sambrook et al., *Molecular Cloning: A Laboratory Manual* (2nd ed.), Vols. 1–3, Cold Spring Harbor Laboratory, (1989), or *Current Protocols in Molecular Biology*, F. Ausubel et al., ed. Greene Publishing and Wiley-Interscience, New York (1987)).

Frequently, it is desirable to amplify the nucleic acid sample prior to assaying for gene copy number or expression level. One of skill in the art will appreciate that whatever amplification method is used, if a quantitative result is desired, care must be taken to use a method that maintains or controls for the relative frequencies of the amplified nucleic acids.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction.

One preferred internal standard is a synthetic AW106 cRNA. The AW106 cRNA is combined with RNA isolated from the sample according to standard techniques known to those of skill in the art. The RNA is then reverse transcribed using a reverse transcriptase to provide copy DNA. The cDNA sequences are then amplified (e.g., by PCR) using labeled primers. The amplification products are separated, typically by electrophoresis, and the amount of radioactivity (proportional to the amount of amplified product) is determined. The amount of mRNA in the sample is then calculated by comparison with the signal produced by the known AW106 RNA standard. Detailed protocols for quantitative PCR are provided in PCR Protocols, A Guide to Methods and Applications, Innis et al., Academic Press, Inc. N.Y., (1990).

In a particularly preferred embodiment, where it is desired to quantify the transcription level (and thereby expression) of a one or more genes in a sample, the nucleic acid sample is one in which the concentration of the mRNA transcript(s) of the gene or genes, or the concentration of the nucleic acids derived from the mRNA transcript(s), is proportional to the transcription level (and therefore expression level) of that gene. Similarly, it is preferred that the hybridization signal intensity be proportional to the amount of hybridized nucleic acid. While it is preferred that the proportionality be relatively strict (e.g., a doubling in transcription rate results in a doubling in mRNA transcript in the sample nucleic acid pool and a doubling in hybridization signal), one of skill will appreciate that the proportionality can be more relaxed and even non-linear. Thus, for example, an assay where a 5 fold difference in concentration of the target mRNA results in a 3 to 6 fold difference in hybridization intensity is sufficient for most purposes. Where more precise quantification is required appropriate controls can be run to correct for variations introduced in sample preparation and hybridization as described herein. In addition, serial dilutions of "standard" target nucleic acids (e.g., mRNAs) can be used to prepare calibration curves according to methods well known to those of skill in the art. Of course, where simple detection of the presence or absence of a transcript or large differences of changes in nucleic acid concentration is desired, no elaborate control or calibration is required.

In the simplest embodiment, such a nucleic acid sample is the total mRNA or a total cDNA isolated and/or otherwise derived from a biological sample. The nucleic acid (either genomic DNA or mRNA) may be isolated from the sample according to any of a number of methods well known to those of skill in the art as indicated above.

2) Hybridization-based assays.

i) Detection of Copy Number.

One method for evaluating the copy number of an MT-SP1 DNA in a sample involves a Southern transfer. In a Southern Blot, the DNA (e.g., genomic DNA), typically fragmented and separated on an electrophoretic gel, is hybridized to a probe specific for the target region. Comparison of the intensity of the hybridization signal from the probe for the target region with control probe signal from analysis of normal genomic DNA (e.g., a non-amplified portion of the same or related cell, tissue, organ, etc.) provides an estimate of the relative copy number of the target nucleic acid.

An alternative means for determining the copy number of an MT-SP1 gene of this invention is in situ hybridization. In situ hybridization assays are well known (e.g., Angerer (1987) *Meth. Enzymol* 152: 649). Generally, in situ hybridization comprises the following major steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments. The reagent used in each of these steps and the conditions for use vary depending on the particular application.

Preferred hybridization-based assays include, but are not limited to, traditional "direct probe" methods such as Southern blots or in situ hybridization (e.g., FISH), and "comparative probe" methods such as comparative genomic hybridization (CGH). The methods can be used in a wide variety of formats including, but not limited to substrate— (e.g. membrane or glass) bound methods or array-based approaches as described below.

In a typical in situ hybridization assay, cells are fixed to a solid support, typically a glass slide. If a nucleic acid is to be probed, the cells are typically denatured with heat or alkali. The cells are then contacted with a hybridization solution at a moderate temperature to permit annealing of labeled probes specific to the nucleic acid sequence encoding the protein. The targets (e.g., cells) are then typically washed at a predetermined stringency or at an increasing stringency until an appropriate signal to noise ratio is obtained.

The probes are typically labeled, e.g., with radioisotopes or fluorescent reporters as described above. Preferred probes are sufficiently long so as to specifically hybridize with the target nucleic acid(s) under stringent conditions. The preferred size range is from about 20 bases to about 500 bases, more preferably from about 30 bases to about 400 bases and most preferably from about 40 bases to about 300 bases.

In some applications it is necessary to block the hybridization capacity of repetitive sequences. Thus, in some embodiments, tRNA, human genomic DNA, or Cot-1 DNA is used to block non-specific hybridization.

Another effective approach for the quantification of copy number of the gene(s) or EST(s) of this invention is comparative genomic hybridization. In this method, a first collection of (sample) nucleic acids (e.g. from a test sample derived from an organism, tissue, or cell exposed to one or more drugs of abuse) is labeled with a first label, while a second collection of (control) nucleic acids (e.g. from a normal "unexposed" organism, tissue, or cell) is labeled with a second label. The ratio of hybridization of the nucleic acids is determined by the ratio of the two (first and second) labels binding to each fiber in the array. Where there are chromosomal deletions or multiplications, differences in the ratio of the signals from the two labels will be detected and the ratio will provide a measure of the gene and/or EST copy number.

Hybridization protocols suitable for use with the methods of the invention are described, e.g., in Albertson (1984) *EMBO J.* 3: 1227–1234; Pinkel (1988) *Proc. Natl. Acad. Sci. USA* 85: 9138–9142; EPO Pub. No. 430,402; *Methods in Molecular Biology, Vol.* 33: *In Situ Hybridization Protocols*, Choo, ed., Humana Press, Totowa, N.J. (1994), etc. In one particularly preferred embodiment, the hybridization protocol of Pinkel et al. (1998) *Nature Genetics* 20: 207–211, or of Kallioniemi (1992) *Proc. Natl Acad Sci USA* 89:5321–5325 (1992) is used.

ii) Detection of Gene Transcript.

Methods of detecting and/or quantifying the transcript(s) of one or more MT-SP1 gene(s) or EST(s) (e.g. mRNA or cDNA made therefrom) using nucleic acid hybridization techniques are known to those of skill in the art (see Sambrook et al. supra). For example, one method for evaluating the presence, absence, or quantity of gene or EST reverse-transcribed cDNA involves a Southern transfer as described above. Alternatively, in a Northern blot, mRNA is directly quantitated. In brief, the mRNA is isolated from a given cell sample using, for example, an acid guanidinium-phenol-chloroform extraction method. The mRNA is then electrophoresed to separate the mRNA species and the mRNA is transferred from the gel to a nitrocellulose membrane. As with the Southern blots, labeled probes are used to identify and/or quantify the target mRNA.

The probes used herein for detection of the MT-SP1 gene(s) and/or EST(s) of this invention can be full length or less than the full length of the gene or EST. Shorter probes are empirically tested for specificity. Preferably nucleic acid probes are 20 bases or longer in length. (see Sambrook et al. for methods of selecting nucleic acid probe sequences for use in nucleic acid hybridization.) Visualization of the hybridized portions allows the qualitative determination of the presence or absence of gene(s) and/or EST(s) of this invention.

3) Amplification-Based Assays.

In still another embodiment, amplification-based assays can be used to measure or level of gene (or EST) transcript. In such amplification-based assays, the target nucleic acid sequences act as template(s) in amplification reaction(s) (e.g. Polymerase Chain Reaction (PCR) or reverse-transcription PCR (RT-PCR)). In a quantitative amplification, the amount of amplification product will be proportional to the amount of template in the original sample. Comparison to appropriate (e.g. healthy tissue unexposed to drug(s) of abuse) controls provides a measure of the copy number or transcript level of the target gene or EST.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis et al. (1990) *PCR Protocols, A Guide to Methods and Applications*, Academic Press, Inc. N.Y.). The known nucleic acid sequence(s) for the cDNA, genes, and ESTs provided herein is sufficient to enable one of skill to routinely select primers to amplify any portion of the gene.

Other suitable amplification methods include, but are not limited to ligase chain reaction (LCR) (see Wu and Wallace (1989) *Genomics* 4: 560, Landegren et al. (1988) *Science* 241: 1077, and Barringer et al. (1990) *Gene* 89: 117, transcription amplification (Kwoh et al. (1989) *Proc. Natl. Acad. Sci. USA* 86: 1173), self-sustained sequence replication (Guatelli et al. (1990) *Proc. Nat. Acad. Sci. USA* 87: 1874), dot PCR, and linker adapter PCR, etc.

As indicated above, PCR assay methods are well known to those of skill in the art. Similarly, RT-PCR methods are also well known.

4) Hybridization Formats and Optimization of Hybridization Conditions.

i) Array-Based Hybridization Formats.

In one embodiment, the methods of this invention can be utilized in array-based hybridization formats. Arrays are a multiplicity of different "probe" or "target" nucleic acids (or other compounds) attached to one or more surfaces (e.g., solid, membrane, or gel). In a preferred embodiment, the multiplicity of nucleic acids (or other moieties) is attached to a single contiguous surface or to a multiplicity of surfaces juxtaposed to each other.

In an array format a large number of different hybridization reactions can be run essentially "in parallel." This provides rapid, essentially simultaneous, evaluation of a number of hybridizations in a single "experiment". Methods of performing hybridization reactions in array based formats are well known to those of skill in the art (see, e.g., Pastinen (1997) *Genome Res.* 7: 606–614; Jackson (1996) *Nature Biotechnology* 14:1685; Chee (1995) *Science* 274: 610; WO 96/17958, Pinkel et al. (1998) *Nature Genetics* 20: 207–211).

Arrays, particularly nucleic acid arrays can be produced according to a wide variety of methods well known to those of skill in the art. For example, in a simple embodiment, "low density" arrays can simply be produced by spotting (e.g. by hand using a pipette) different nucleic acids at different locations on a solid support (e.g. a glass surface, a membrane, etc.).

This simple spotting, approach has been automated to produce high density spotted arrays (see, e.g., U.S. Pat. No. 5,807,522). This patent describes the use of an automated system that taps a microcapillary against a surface to deposit a small volume of a biological sample. The process is repeated to generate high density arrays.

Arrays can also be produced using oligonucleotide synthesis technology. Thus, for example, U.S. Pat. No. 5,143, 854 and PCT Patent Publication Nos. WO 90/15070 and 92/10092 teach the use of light-directed combinatorial synthesis of high density oligonucleotide arrays. Synthesis of high density arrays is also described in U.S. Pat. Nos. 5,744,305, 5,800,992 and 5,445,934.

In a preferred embodiment, the arrays used in this invention comprise "probe" nucleic acids. These probes or target nucleic acids are then hybridized respectively with their "target" nucleic acids (e.g., mRNA derived from a biological sample).

In another embodiment the array, particularly a spotted array, can include genomic DNA, e.g. one or more clones that provide a high resolution scan of the genome containing the gene(s) and/or EST(s) of this invention. The nucleic acid clones can be obtained from, e.g., HACs, MACs, YACs, BACs, PACs, P1s, cosmids, plasmids, inter-Alu PCR products of genomic clones, restriction digests of genomic clones, cDNA clones, amplification (e.g., PCR) products, and the like.

In various embodiments, the array nucleic acids are derived from previously mapped libraries of clones spanning or including the sequences of the invention. The arrays can be hybridized with a single population of sample nucleic acid or can be used with two differentially labeled collections (as with a test sample and a reference sample).

Many methods for immobilizing nucleic acids on a variety of solid surfaces are known in the art. A wide variety of organic and inorganic polymers, as well as other materials, both natural and synthetic, can be employed as the material for the solid surface. Illustrative solid surfaces include, e.g., nitrocellulose, nylon, glass, quartz, diazotized membranes (paper or nylon), silicones, polyformaldehyde, cellulose, and cellulose acetate. In addition, plastics such as polyethylene, polypropylene, polystyrene, and the like can be used. Other materials which may be employed include paper, ceramics, metals, metalloids, semiconductive materials, cermets or the like. In addition, substances that form gels can be used. Such materials include, e.g., proteins (e.g., gelatins), lipopolysaccharides, silicates, agarose and polyacrylamides. Where the solid surface is porous, various pore sizes may be employed depending upon the nature of the system.

In preparing the surface, a plurality of different materials may be employed, particularly as laminates, to obtain various properties. For example, proteins (e.g., bovine serum albumin) or mixtures of macromolecules (e.g., Denhardt's solution) can be employed to avoid non-specific binding, simplify covalent conjugation, enhance signal detection or the like. If covalent bonding between a compound and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. The manner of linking a wide variety of compounds to various surfaces is well known and is amply illustrated in the literature.

For example, methods for immobilizing nucleic acids by introduction of various functional groups to the molecules is known (see, e.g., Bischoff (1987) *Anal. Biochem.*, 164: 336–344; Kremsky (1987) *Nucl. Acids Res.* 15: 2891–2910). Modified nucleotides can be placed on the target using PCR primers containing the modified nucleotide, or by enzymatic end labeling with modified nucleotides. Use of glass or membrane supports (e.g., nitrocellulose, nylon, polypropylene) for the nucleic acid arrays of the invention is advantageous because of well developed technology employing manual and robotic methods of arraying targets at relatively high element densities. Such membranes are generally available and protocols and equipment for hybridization to membranes is well known.

Target elements of various sizes, ranging from 1 mm diameter down to 1 μm can be used. Relatively simple approaches capable of quantitative fluorescent imaging of 1cm$^2$ areas have been described that permit acquisition of data from a large number of target elements in a single image (see, e.g., Wittrup (1994) *Cytometry* 16:206–213, Pinkel et al. (1998) *Nature Genetics* 20: 207–211).

Arrays on solid surface substrates with much lower fluorescence than membranes, such as glass, quartz, or small beads, can achieve much better sensitivity. Substrates such as glass or fused silica are advantageous in that they provide a very low fluorescence substrate, and a highly efficient hybridization environment. Covalent attachment of the target nucleic acids to glass or synthetic fused silica can be accomplished according to a number of known techniques (described above). Nucleic acids can be conveniently coupled to glass using commercially available reagents. For instance, materials for preparation of silanized glass with a number of functional groups are commercially available or can be prepared using standard techniques (see, e.g., Gait (1984) *Oligonucleotide Synthesis: A Practical Approach*, IRL Press, Wash., D.C.). Quartz cover slips, which have at least 10-fold lower autofluorescence than glass, can also be silanized.

Alternatively, probes can also be immobilized on commercially available coated beads or other surfaces. For instance, biotin end-labeled nucleic acids can be bound to commercially available avidin-coated beads. Streptavidin or anti-digoxigenin antibody can also be attached to silanized glass slides by protein-mediated coupling using e.g., protein A following standard protocols (see, e.g., Smith (1992) *Science* 258: 1122–1126). Biotin or digoxigenin end-labeled nucleic acids can be prepared according to standard techniques. Hybridization to nucleic acids attached to beads is accomplished by suspending them in the hybridization mix, and then depositing them on the glass substrate for analysis after washing. Alternatively, paramagnetic particles, such as ferric oxide particles, with or without avidin coating, can be used.

ii) Other Hybridization Formats.

A variety of nucleic acid hybridization formats are known to those skilled in the art. For example, common formats include sandwich assays and competition or displacement assays. Hybridization techniques are generally described in Hames and Higgins (1985) *Nucleic Acid Hybridization, A Practical Approach*, IRL Press; Gall and Pardue (1969) *Proc. Natl. Acad. Sci. USA* 63: 378–383; and John et al. (1969) *Nature* 223: 582–587.

Sandwich assays are commercially useful hybridization assays for detecting or isolating nucleic acid sequences. Such assays utilize a "capture" nucleic acid covalently immobilized to a solid support and a labeled "signal" nucleic acid in solution. The sample will provide the target nucleic acid. The "capture" nucleic acid and "signal" nucleic acid probe hybridize with the target nucleic acid to form a "sandwich" hybridization complex. To be most effective, the signal nucleic acid should not hybridize with the capture nucleic acid.

Typically, labeled signal nucleic acids are used to detect hybridization. Complementary nucleic acids or signal nucleic acids may be labeled by any one of several methods typically used to detect the presence of hybridized polynucleotides. The most common method of detection is the use of autoradiography with $^3$H, $^{125}$I, $^{35}$S, $^{14}$C, or $^{32}$P-labelled probes or the like. Other labels include ligands that bind to labeled antibodies, fluorophores, chemi-luminescent agents, enzymes, and antibodies which can serve as specific binding pair members for a labeled ligand.

Detection of a hybridization complex may require the binding of a signal generating complex to a duplex of target and probe polynucleotides or nucleic acids. Typically, such binding occurs through ligand and anti-ligand interactions as between a ligand-conjugated probe and an anti-ligand conjugated with a signal.

The sensitivity of the hybridization assays may be enhanced through use of a nucleic acid amplification system that multiplies the target nucleic acid being detected. Examples of such systems include the polymerase chain reaction (PCR) system and the ligase chain reaction (LCR) system. Other methods recently described in the art are the nucleic acid sequence based amplification (NASBAO, Cangene, Mississauga, Ontario) and Q Beta Replicase systems.

iii) Optimization of Hybridization Conditions.

Nucleic acid hybridization simply involves providing a denatured probe and target nucleic acid under conditions where the probe and its complementary target can form stable hybrid duplexes through complementary base pairing. The nucleic acids that do not form hybrid duplexes are then washed away leaving the hybridized nucleic acids to be detected, typically through detection of an attached detectable label. It is generally recognized that nucleic acids are denatured by increasing the temperature or decreasing the salt concentration of the buffer containing the nucleic acids, or in the addition of chemical agents, or the raising of the pH. Under low stringency conditions (e.g., low temperature and/or high salt and/or high target concentration) hybrid duplexes (e.g., DNA:DNA, RNA:RNA, or RNA:DNA) will form even where the annealed sequences are not perfectly complementary. Thus specificity of hybridization is reduced at lower stringency. Conversely, at higher stringency (e.g., higher temperature or lower salt) successful hybridization requires fewer mismatches.

One of skill in the art will appreciate that hybridization conditions may be selected to provide any degree of stringency. In a preferred embodiment, hybridization is performed at low stringency to ensure hybridization and then subsequent washes are performed at higher stringency to eliminate mismatched hybrid duplexes. Successive washes may be performed at increasingly higher stringency (e.g., down to as low as 0.25×SSPE at 37° C. to 70° C.) until a desired level of hybridization specificity is obtained. Stringency can also be increased by addition of agents such as formamide. Hybridization specificity may be evaluated by comparison of hybridization to the test probes with hybridization to the various controls that can be present.

In general, there is a tradeoff between hybridization specificity (stringency) and signal intensity. Thus, in a preferred embodiment, the wash is performed at the highest stringency that produces consistent results and that provides a signal intensity greater than approximately 10% of the background intensity. Thus, in a preferred embodiment, the hybridized array may be washed at successively higher stringency solutions and read between each wash. Analysis of the data sets thus produced will reveal a wash stringency above which the hybridization pattern is not appreciably altered and which provides adequate signal for the particular probes of interest.

In a preferred embodiment, background signal is reduced by the use of a blocking reagent (e.g., tRNA, sperm DNA, cot-1 DNA, etc.) during the hybridization to reduce non-specific binding. The use of blocking agents in hybridization is well known to those of skill in the art (see, e.g., Chapter 8 in P. Tijssen, supra.)

Methods of optimizing hybridization conditions are well known to those of skill in the art (see, e.g., Tijssen (1993) *Laboratory Techniques in Biochemistry and Molecular Biology*, Vol. 24: *Hybridization With Nucleic Acid Probes*, Elsevier, N.Y.).

Optimal conditions are also a function of the sensitivity of label (e.g., fluorescence) detection for different combinations of substrate type, fluorochrome, excitation and emission bands, spot size and the like. Low fluorescence background surfaces can be used (see, e.g., Chu (1992) *Electrophoresis* 13:105–114). The sensitivity for detection of spots ("target elements") of various diameters on the candidate surfaces can be readily determined by, e.g., spotting a dilution series of fluorescently end labeled DNA fragments. These spots are then imaged using conventional fluorescence microscopy. The sensitivity, linearity, and dynamic range achievable from the various combinations of fluorochrome and solid surfaces (e.g., glass, fused silica, etc.) can thus be determined. Serial dilutions of pairs of fluorochrome in known relative proportions can also be analyzed. This determines the accuracy with which fluorescence ratio measurements reflect actual fluorochrome ratios over the dynamic range permitted by the detectors and fluorescence of the substrate upon which the probe has been fixed.

iv) Labeling and Detection of Nucleic Acids.

In a preferred embodiment, the hybridized nucleic acids are detected by detecting one or more labels attached to the sample nucleic acids. The labels may be incorporated by any of a number of means well known to those of skill in the art. Means of attaching labels to nucleic acids include, for example nick translation, or end-labeling by kinasing of the nucleic acid and subsequent attachment (ligation) of a linker joining the sample nucleic acid to a label (e.g., a fluorophore). A wide variety of linkers for the attachment of labels to nucleic acids are also known. In addition, intercalating dyes and fluorescent nucleotides can also be used.

Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like, see, e.g., Molecular Probes, Eugene, Oreg., USA), radiolabels (e.g., $^3$H, $^{125}$I, $^{35}$S, $^{14}$C, or $^{32}$P) enzymes (e.g., horse radish peroxidase, alkaline phosphatase and others commonly used in an ELISA), and colorimetric labels such as colloidal gold (e.g., gold particles in the 40–80 nm diameter size range scatter green light with high efficiency) or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

A fluorescent label is preferred because it provides a very strong signal with low background. It is also optically detectable at high resolution and sensitivity through a quick scanning procedure. The nucleic acid samples can all be labeled with a single label, e.g., a single fluorescent label. Alternatively, in another embodiment, different nucleic acid samples can be simultaneously hybridized where each nucleic acid sample has a different label. For instance, one target could have a green fluorescent label and a second target could have a red fluorescent label. The scanning step will distinguish sites of binding of the red label from those binding the green fluorescent label. Each nucleic acid sample (target nucleic acid) can be analyzed independently from one another.

Suitable chromogens which can be employed include those molecules and compounds which absorb light in a distinctive range of wavelengths so that a color can be observed or, alternatively, which emit light when irradiated with radiation of a particular wave length or wave length range, e.g., fluorescers.

Desirably, fluorescers should absorb light above about 300 nm, preferably about 350 nm, and more preferably above about 400 nm, usually emitting at wavelengths greater than about 10 nm higher than the wavelength of the light absorbed. It should be noted that the absorption and emission characteristics of the bound dye can differ from the unbound dye. Therefore, when referring to the various wavelength ranges and characteristics of the dyes, it is intended to indicate the dyes as employed and not the dye which is unconjugated and characterized in an arbitrary solvent.

Fluorescers are generally preferred because by irradiating a fluorescer with light, one can obtain a plurality of emissions. Thus, a single label can provide for a plurality of measurable events.

Detectable signal can also be provided by chemiluminescent and bioluminescent sources. Chemiluminescent sources include a compound which becomes electronically excited by a chemical reaction and can then emit light which serves as the detectable signal or donates energy to a fluorescent acceptor. Alternatively, luciferins can be used in conjunction with luciferase or lucigenins to provide bioluminescence.

Spin labels are provided by reporter molecules with an unpaired electron spin which can be detected by electron spin resonance (ESR) spectroscopy. Exemplary spin labels include organic free radicals, transitional metal complexes, particularly vanadium, copper, iron, and manganese, and the like. Exemplary spin labels include nitroxide free radicals.

The label may be added to the target (sample) nucleic acid(s) prior to, or after the hybridization. So called "direct labels" are detectable labels that are directly attached to or incorporated into the target (sample) nucleic acid prior to hybridization. In contrast, so called "indirect labels" are joined to the hybrid duplex after hybridization. Often, the indirect label is attached to a binding moiety that has been attached to the target nucleic acid prior to the hybridization. Thus, for example, the target nucleic acid may be biotinylated before the hybridization. After hybridization, an avidin-conjugated fluorophore will bind the biotin bearing hybrid duplexes providing a label that is easily detected. For a detailed review of methods of labeling nucleic acids and detecting labeled hybridized nucleic acids see *Laboratory Techniques in Biochemistry and Molecular Biology, Vol. 24: Hybridization With Nucleic Acid Probes*, P. Tijssen, ed. Elsevier, N.Y., (1993)).

Fluorescent labels are easily added during an in vitro transcription reaction. Thus, for example, fluorescein labeled UTP and CTP can be incorporated into the RNA produced in an in vitro transcription.

The labels can be attached directly or through a linker moiety. In general, the site of label or linker-label attachment is not limited to any specific position. For example, a label may be attached to a nucleoside, nucleotide, or analogue thereof at any position that does not interfere with detection or hybridization as desired. For example, certain Label-ON Reagents from Clontech (Palo Alto, Calif.) provide for labeling interspersed throughout the phosphate backbone of an oligonucleotide and for terminal labeling at the 3' and 5' ends. As shown for example herein, labels can be attached at positions on the ribose ring or the ribose can be modified and even eliminated as desired. The base moieties of useful labeling reagents can include those that are naturally occurring or modified in a manner that does not interfere with the purpose to which they are put. Modified bases include but are not limited to 7-deaza A and G, 7-deaza-8-aza A and G, and other heterocyclic moieties.

It will be recognized that fluorescent labels are not to be limited to single species organic molecules, but include inorganic molecules, multi-molecular mixtures of organic and/or inorganic molecules, crystals, heteropolymers, and the like. Thus, for example, CdSe-CdS core-shell nanocrystals enclosed in a silica shell can be easily derivatized for coupling to a biological molecule (Bruchez et al. (1998) *Science*, 281: 2013–2016). Similarly, highly fluorescent quantum dots (zinc sulfide-capped cadmium selenide) have been covalently coupled to biomolecules for use in ultrasensitive biological detection (Warren and Nie (1998) *Science*, 281: 2016–2018).

C) Polypeptide-Based Assays.

In addition to, or in alternative to, the detection of nucleic acid level(s), alterations in expression of MT-SP1 can be detected and/or quantified by detecting and/or quantifying the amount and/or activity of translated MT-SP1 protein(s). In particularly preferred embodiments, the MT-SP1 proteins are detected immunohistochemically, using a radioimmunoassay, or using other immunoassay(s). As used herein, an immunoassay is an assay that utilizes an antibody to specifically bind to the analyte (MT-SP1). The immunoassay is thus characterized by detection of specific binding of a MT-SP1 protein., or protein fragment, to an anti-MT-SP1 antibody as opposed to the use of other physical or chemical properties to isolate, target, and quantify the analyte.

1) Detection of Expressed Protein

The MT-SP1 polypeptide(s) of this invention can be detected and quantified by any of a number of methods well known to those of skill in the art. These may include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunohistochemistry, affinity chromatography, immunoelectrophoresis, radioimmunoassay (RIA), enzyme-linked immunosorbent assays (ELISAs), immunofluorescent assays, western blotting, and the like.

In one preferred embodiment, the MT-SP1 polypeptide(s) are detected and/or quantified using immunohistochemical methods. In this approach, antibodies that specifically bind to an MT-SP1 are contacted with the biological sample (e.g., a histological sample). Those antibodies that specifically bind to the sample are visualized, or otherwise detected, and provide an indication of the location, presence, absence or quantity of MT-SP1 protein in the sample. The antibodies are typically detected by detection of a label either affixed to the antibody prior to or subsequent to the "contacting" step. Immunohistochemical methods are well known to those of skill in the art (see, e.g., Kleihues et al. (1993) *Histological typing of tumours of the central nervous system*, Springer Verlag, New York).

In another preferred embodiment, the MT-SP1 polypeptide(s) are detected/quantified in an electrophoretic protein separation (e.g. a 1- or 2-dimensional electrophoresis). Means of detecting proteins using electrophoretic techniques are well known to those of skill in the art (see generally, R. Scopes (1982) *Protein Purification*, Springer-Verlag, N.Y.; Deutscher, (1990) *Methods in Enzymology Vol. 182: Guide to Protein Purification*, Academic Press, Inc., N.Y.).

Another preferred embodiment utilizes a Western blot (immunoblot) analysis to detect and quantify the presence of polypeptide(s) of this invention in the sample. This technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind the target polypeptide(s).

The antibodies specifically bind to the target polypeptide(s) and may be directly labeled or alternatively may be subsequently detected using labeled antibodies (e.g., labeled sheep anti-mouse antibodies) that specifically bind to the a domain of the antibody.

Other suitable assay formats include, but are not limited to, liposome immunoassays (LIA), which use liposomes designed to bind specific molecules (e.g., antibodies) and release encapsulated reagents or markers. The released chemicals are then detected according to standard techniques (see, Monroe et al. (1986) *Amer. Clin. Prod. Rev.* 5: 34–41).

In a preferred embodiment, the MT-SP1 protein(s) are detected and/or quantified in the biological sample using any of a number of well recognized immunological binding assays (immunoassays) (see, e.g., U.S. Pat. Nos. 4,366,241; 4,376,110; 4,517,288; and 4,837,168). For a review of the general immunoassays, see also *Methods in Cell Biology Volume 37: Antibodies in Cell Biology*, Asai, ed. Academic Press, Inc. New York (1993); *Basic and Clinical Immunology* 7th Edition, Stites & Terr, eds. (1991).

As used herein, an immunoassay is an assay that utilizes an antibody to specifically bind to the analyte (e.g., an MT-SP1 polypeptide). The immunoassay is thus characterized by detection of specific binding of a polypeptide of this invention to an antibody as opposed to the use of other physical or chemical properties to isolate, target, and quantify the analyte.

Immunological binding assays (or immunoassays) typically utilize a "capture agent" to specifically bind to and often immobilize the analyte (in this case an MT-SP1 polypeptide). In preferred embodiments, the capture agent is an antibody.

Immunoassays also often utilize a labeling agent to specifically bind to and label the binding complex formed by the capture agent and the analyte. The labeling agent may itself be one of the moieties comprising the antibody/analyte complex. Thus, the labeling agent may be a labeled polypeptide or a labeled antibody that specifically recognizes the already bound target polypeptide. Alternatively, the labeling agent may be a third moiety, such as another antibody, that specifically binds to the capture agent/polypeptide complex.

Other proteins capable of specifically binding immunoglobulin constant regions, such as protein A or protein G may also be used as the label agent. These proteins are normal constituents of the cell walls of streptococcal bacteria. They exhibit a strong non-immunogenic reactivity with immunoglobulin constant regions from a variety of species (see, generally Kronval, et al. (1973) *J. Immunol.*, 111: 1401–1406, and Akerstrom (1985) *J. Immunol.*, 135: 2589–2542).

As indicated above, immunoassays for the detection and/or quantification of the MT-SP1 polypeptide(s) of this invention can take a wide variety of formats well known to those of skill in the art. Preferred immunoassays for detecting the target polypeptide(s) are either competitive or noncompetitive. Noncompetitive immunoassays are assays in which the amount of captured analyte is directly measured. In one preferred "sandwich" assay, for example, the capture agents (antibodies) can be bound directly to a solid substrate where they are immobilized. These immobilized antibodies then capture the target polypeptide present in the test sample. The target polypeptide thus immobilized is then bound by a labeling agent, such as a second antibody bearing a label.

In competitive assays, the amount of analyte (MT-SP1 polypeptide) present in the sample is measured indirectly by measuring the amount of an added (exogenous) analyte displaced (or competed away) from a capture agent (antibody) by the analyte present in the sample. In one competitive assay, a known amount of, in this case, labeled polypeptide is added to the sample and the sample is then contacted with a capture agent. The amount of labeled polypeptide bound to the antibody is inversely proportional to the concentration of target polypeptide present in the sample.

In one particularly preferred embodiment, the antibody is immobilized on a solid substrate. The immobilized antibody captures the target MT-SP1 thereby immobilizing the analyte. The amount of analyte (target polypeptide) bound to the antibody may be determined either by measuring the amount of target polypeptide present in the polypeptide/antibody complex, or alternatively by measuring the amount of remaining uncomplexed polypeptide.

The assays of this invention are scored (as positive or negative or quantity of target polypeptide) according to standard methods well known to those of skill in the art. The particular method of scoring will depend on the assay format and choice of label. For example, a Western Blot assay can be scored by visualizing the colored product produced by the enzymatic label. A clearly visible colored band or spot at the correct molecular weight is scored as a positive result, while the absence of a clearly visible spot or band is scored as a negative. The intensity of the band or spot can provide a quantitative measure of target polypeptide concentration.

Antibodies for use in the various immunoassays described herein, can be produced as described below.

2) Detection of Enzyme Activity

In another embodiment, levels of gene expression/regulation are assayed by measuring the enzymatic activity of the polypeptide encoded by the respective gene(s). For example, the MT-SP1 polypeptide(s) of this invention are serine proteases and their activity can be readily detected by assaying the cleavage of a target substrate. Thus, Example 1 illustrated quantification of MT-SP1 activity using an active site titration with MUGB. The catalytic activity of the protease domain can also be monitored using pNA substrates. In particular, MT-SP1 protease activity can be tested against tetrapeptide substrates of the form Suc-AAPX-pNA, which contained various amino acids at the P1 position (P1-Ala, Asp, Glu, Phe, Leu, Met, Lys, or Arg). In a preferred embodiment, substrates with P1-Lys or P1-Arg are used. Protease domain can also be characterized using the substrate Spectrozyme tPA (hexahydrotyrosyl-Gly-Arg-pNA) as described in Example 1. Using the teaching provided herein, assays for activity of other MT-SP1 proteases are easily performed.

3) Antibodies to Polypeptides Expressed by the Genes or ESTs Identified Herein.

Either polyclonal or monoclonal antibodies may be used in the immunoassays of the invention described herein. Polyclonal antibodies are preferably raised by multiple injections (e.g. subcutaneous or intramuscular injections) of substantially pure polypeptides or antigenic polypeptides into a suitable non-human mammal. The antigenicity of the target peptides can be determined by conventional techniques to determine the magnitude of the antibody response of an animal that has been immunized with the peptide. Generally, the peptides that are used to raise antibodies for use in the methods of this invention should generally be those which induce production of high titers of antibody with relatively high affinity for target polypeptides encoded by the MT-SP1 genes or ESTs of this invention.

If desired, the immunizing peptide may be coupled to a carrier protein by conjugation using techniques that are well-known in the art. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g. a mouse or a rabbit).

The antibodies are then obtained from blood samples taken from the mammal. The techniques used to develop polyclonal antibodies are known in the art (see, e.g., *Methods of Enzymology*, "Production of Antisera With Small Doses of Immunogen: Multiple Intradermal Injections", Langone, et al. eds. (Acad. Press, 1981)). Polyclonal antibodies produced by the animals can be further purified, for example, by binding to and elution from a matrix to which the peptide to which the antibodies were raised is bound.

Those of skill in the art will know of various techniques common in the immunology arts for purification and/or concentration of polyclonal antibodies, as well as monoclonal antibodies see, for example, Coligan, et al. (1991) Unit 9, *Current Protocols in Immunology*, Wiley Interscience).

Preferably, however, the antibodies produced will be monoclonal antibodies ("mAb's"). For preparation of monoclonal antibodies, immunization of a mouse or rat is preferred. The term "antibody" as used in this invention includes intact molecules as well as fragments thereof, such as, Fab and F(ab')$_2$, and/or single-chain antibodies (e.g. scFv) which are capable of binding an epitopic determinant. Also, in this context, the term "mab's of the invention" refers to monoclonal antibodies with specificity for a polypeptide encoded by an MT-SP1 gene or EST.

The general method used for production of hybridomas secreting mAbs is well known (Kohler and Milstein (1975) *Nature*, 256:495). Briefly, as described by Kohler and Milstein the technique comprised isolating lymphocytes from regional draining lymph nodes of five separate cancer patients with either melanoma, teratocarcinoma or cancer of the cervix, glioma or lung, (where samples were obtained from surgical specimens), pooling the cells, and fusing the cells with SHFP-1. Hybridomas were screened for production of antibody which bound to cancer cell lines. Confirmation of specificity among mAb's can be accomplished using relatively routine screening techniques (such as the enzyme-linked immunosorbent assay, or "ELISA") to determine the elementary reaction pattern of the mAb of interest.

It is also possible to evaluate an mAb to determine whether it has the same specificity as a mAb of the invention without undue experimentation by determining whether the mAb being tested prevents a mAb of the invention from binding to the target polypeptide isolated as described above. If the mAb being tested competes with the mAb of the invention, as shown by a decrease in binding by the mAb of the invention, then it is likely that the two monoclonal antibodies bind to the same or a closely related epitope. Still another way to determine whether a mAb has the specificity of a mAb of the invention is to preincubate the mAb of the invention with an antigen with which it is normally reactive, and determine if the mAb being tested is inhibited in its ability to bind the antigen. If the mAb being tested is inhibited then, in all likelihood, it has the same, or a closely related, epitopic specificity as the mAb of the invention.

Antibodies fragments, e.g. single chain antibodies (scFv or others), can also be produced/selected using phage display technology. The ability to express antibody fragments on the surface of viruses that infect bacteria (bacteriophage or phage) makes it possible to isolate a single binding antibody fragment, e.g., from a library of greater than $10^{10}$ nonbinding clones. To express antibody fragments on the surface of phage (phage display), an antibody fragment gene is inserted into the gene encoding a phage surface protein (e.g., pIII) and the antibody fragment-pIII fusion protein is displayed on the phage surface (McCafferty et al. (1990) *Nature*, 348: 552–554; Hoogenboom et al. (1991) *Nucleic Acids Res.* 19: 4133–4137).

Since the antibody fragments on the surface of the phage are functional, phage bearing antigen binding antibody fragments can be separated from non-binding phage by antigen affinity chromatography (McCafferty et al. (1990) *Nature*, 348: 552–554). Depending on the affinity of the antibody fragment, enrichment factors of 20 fold–1,000,000 fold are obtained for a single round of affinity selection. By infecting bacteria with the eluted phage, however, more phage can be grown and subjected to another round of selection. In this way, an enrichment of 1000 fold in one round can become 1,000,000 fold in two rounds of selection (McCafferty et al. (1990) *Nature*, 348: 552–554). Thus even when enrichments are low (Marks et al. (1991) *J. Mol. Biol.* 222: 581–597), multiple rounds of affinity selection can lead to the isolation of rare phage. Since selection of the phage antibody library on antigen results in enrichment, the majority of clones bind antigen after as few as three to four rounds of selection. Thus only a relatively small number of clones (several hundred) need to be analyzed for binding to antigen.

Human antibodies can be produced without prior immunization by displaying very large and diverse V-gene repertoires on phage (Marks et al. (1991) *J. Mol. Biol.* 222: 581–597). In one embodiment natural $V_H$ and $V_L$ repertoires present in human peripheral blood lymphocytes are were isolated from unimmunized donors by PCR. The V-gene repertoires were spliced together at random using PCR to create a scFv gene repertoire which is was cloned into a phage vector to create a library of 30 million phage antibodies (Id.). From this single "naive" phage antibody library, binding antibody fragments have been isolated against more than 17 different antigens, including haptens, polysaccharides and proteins (Marks et al. (1991) *J. Mol. Biol.* 222: 581–597; Marks et al. (1993). *Bio/Technology*. 10: 779–783; Griffiths et al. (1993) *EMBO J.* 12: 725–734; Clackson et al. (1991) *Nature*. 352: 624–628). Antibodies have been produced against self proteins, including human thyroglobulin, immunoglobulin, tumor necrosis factor and CEA (Griffiths et al. (1993) *EMBO J.* 12: 725–734). It is also possible to isolate antibodies against cell surface antigens by selecting directly on intact cells. The antibody fragments are highly specific for the antigen used for selection and have affinities in the 1 μM to 100 nM range (Marks et al. (1991) *J. Mol. Biol.* 222: 581–597; Griffiths et al. (1993) *EMBO J.* 12: 725–734). Larger phage antibody libraries result in the isolation of more antibodies of higher binding affinity to a greater proportion of antigens.

It will also be recognized that antibodies can be prepared by any of a number of commercial services (e.g., Berkeley antibody laboratories, Bethyl Laboratories, Anawa, Eurogenetec, etc.).

V. MT-SP1 as a Target for Screening for Therapeutics.

A) Screening Target for Agents that Modulate MT-SP1 Expression and/or Activity.

While, in one embodiment, the assays described above provided methods of detecting the presence or absence, or quantifying expression of an MT-SP1 protease, it will be appreciated that the same assays can be used to screen for agents that modulate the expression of and/or the activity of an MT-SP1 serine protease. To screen for potential modulators, the assays described above are performed in the presence of one or more test agents or are performed using biological samples from cells and/or tissues and/or organs and/or organisms exposed to one or more test agents. The MT-SP1 activity and/or expression level is determined and, in a preferred embodiment, compared to the activity level(s) observed in "control" assays (e.g., the same assays lacking the test agent). A difference between the MT-SP1 expression and/or activity in the "test" assay as compared to the control assay indicates that the test agent is a "modulator" of SP1 expression and/or activity.

In a preferred embodiment, the assays of this invention level are deemed to show a positive result, e.g. elevated expression and/or MT-SP1 activity, genes, when the measured protein or nucleic acid level or protein activity is greater than the level measured or known for a control sample (e.g. either a level known or measured for a normal healthy cell, tissue or organism mammal of the same species not exposed to the or putative modulator (test agent), or a "baseline/reference" level determined at a different tissue and/or a different time for the same individual). In a particularly preferred embodiment, the assay is deemed to show a positive result when the difference between sample and "control" is statistically significant (e.g. at the 85% or greater, preferably at the 90% or greater, more preferably at the 95% or greater and most preferably at the 98% or greater confidence level).

B) Pre-Screening for Agents that Specifically Bind/Interact with MT-SP1.

In certain embodiments it is desired to pre-screen test agents for the ability to interact with (e.g. specifically bind to) a MT-SP1 nucleic acid or polypeptide. Specifically binding test agents are more likely to interact with and thereby modulate MT-SP1 expression and/or activity. Thus, in some preferred embodiments, the test agent(s) are pre-screened for binding to MT-SP1 or to an MT-SP1 nucleic acid before performing the more complex assays described above.

In one embodiment, such pre-screening is accomplished with simple binding assays. Means of assaying for specific binding or the binding affinity of a particular ligand for a nucleic acid or for a protein are well known to those of skill in the art. In preferred binding assays, the MT-SP1 protein or nucleic acid is immobilized and exposed to a test agent (which can be labeled), or alternatively, the test agent(s) are immobilized and exposed to an MT-SP1 or to a MT-SP1 nucleic acid (which can be labeled). The immobilized moiety is then washed to remove any unbound material and the bound test agent or bound MT-SP1 protein or nucleic acid is detected (e.g. by detection of a label attached to the bound molecule). The amount of immobilized label is proportional to the degree of binding between the MT-SP1 protein or nucleic acid and the test agent.

C) High Throughput Screening for MT-SP1 Modulators (e.g., Therapeutics).

The assays for modulators of MT-SP1 expression and/or activity described herein are also amenable to "high-throughput" modalities. Conventionally, new chemical entities with useful properties (e.g., modulation of MT-SP1 activity or expression) are generated by identifying a chemical compound (called a "lead compound") with some desirable property or activity, creating variants of the lead compound, and evaluating the property and activity of those variant compounds. However, the current trend is to shorten the time scale for all aspects of drug discovery. Because of the ability to test large numbers quickly and efficiently, high throughput screening (HTS) methods are replacing conventional lead compound identification methods.

In one preferred embodiment, high throughput screening methods involve providing a library containing a large number of compounds (candidate compounds) potentially having the desired activity. Such "combinatorial chemical libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

1) Combinatorial Chemical Libraries for Potential Modulators of MT-SP1.

The likelihood of an assay identifying a MT-SP1 expression or activity modulator is increased when the number and types of test agents used in the screening system is increased. Recently, attention has focused on the use of combinatorial chemical libraries to assist in the generation of new chemical compound leads. A combinatorial chemical library is a collection of diverse chemical compounds generated by either chemical synthesis or biological synthesis by combining a number of chemical "building blocks" such as reagents. For example, a linear combinatorial chemical library such as a polypeptide library is formed by combining a set of chemical building blocks called amino acids in every possible way for a given compound length (i.e., the number of amino acids in a polypeptide compound). Millions of chemical compounds can be synthesized through such combinatorial mixing of chemical building blocks. For example, one commentator has observed that the systematic, combinatorial mixing of 100 interchangeable chemical building blocks results in the theoretical synthesis of 100 million tetrameric compounds or 10 billion pentameric compounds (Gallop et al. (1994) 37(9): 1233–1250).

Preparation and screening of combinatorial chemical libraries is well known to those of skill in the art. Such combinatorial chemical libraries include, but are not limited to, peptide libraries (see, e.g., U.S. Pat. No. 5,010,175, Furka (1991) *Int. J. Pept. Prot. Res.,* 37: 487–493, Houghton et al. (1991) *Nature,* 354: 84–88). Peptide synthesis is by no means the only approach envisioned and intended for use with the present invention. Other chemistries for generating chemical diversity libraries can also be used. Such chemistries include, but are not limited to: peptoids (PCT Publication No WO 91/19735, 26 Dec. 1991), encoded peptides (PCT Publication WO 93/20242, 14 Oct. 1993), random bio-oligomers (PCT Publication WO 92/00091, 9 Jan. 1992), benzodiazepines (U.S. Pat. No. 5,288,514), diversomers such as hydantoins, benzodiazepines and dipeptides (Hobbs et al., (1993) *Proc. Nat. Acad. Sci. USA* 90: 6909–6913), vinylogous polypeptides (Hagihara et al. (1992) *J. Amer. Chem. Soc.* 114: 6568), nonpeptidal peptidomimetics with a Beta-D-Glucose scaffolding (Hirschmann et al., (1992) *J. Amer. Chem. Soc.* 114: 9217–9218), analogous organic syntheses of small compound libraries (Chen et al. (1994) *J. Amer. Chem. Soc.* 116: 2661), oligocarbamates (Cho, et al., (1993) *Science* 261: 1303), and/or peptidyl phosphonates (Campbell et al., (1994) *J. Org. Chem.* 59: 658). See, generally, Gordon et al., (1994) *J. Med. Chem.* 37:1385, nucleic acid libraries (see, e.g., Strategene, Corp.), peptide nucleic acid libraries (see, e.g., U.S. Pat. No. 5,539,083) antibody libraries (see, e.g., Vaughn et al. (1996) *Nature Biotechnology,* 14(3): 309–314), and PCT/US96/10287), carbohydrate libraries (see, e.g., Liang et al. (1996) *Science,* 274: 1520–1522, and U.S. Pat. No. 5,593,853), and small organic molecule libraries (see, e.g., benzodiazepines, Baum (1993) C&EN, January 18, page 33, isoprenoids U.S. Pat. No. 5,569,588, thiazolidinones and metathiazanones U.S. Pat. No. 5,549,974, pyrrolidines U.S. Pat. Nos. 5,525,735 and 5,519,134, morpholino compounds U.S. Pat. No. 5,506,337, benzodiazepines U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.).

A number of well known robotic systems have also been developed for solution phase chemistries. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.) which mimic the manual synthetic operations performed by a chemist. Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

2) High Throughput Assays of Chemical Libraries for Modulators of MT-SP1.

Any of the assays for agents that modulate MT-SP1 expression and/or activity (e.g. that have potential therapeutic activity) are amenable to high throughput screening. As described above, having identified the nucleic acid whose expression is altered upon exposure to a drug of abuse, likely modulators either inhibit expression of the gene product, or inhibit the activity of the expressed protein. Preferred assays thus detect inhibition of transcription (i.e., inhibition of mRNA production) by the test compound(s), inhibition of protein expression by the test compound(s), or binding to the gene (e.g., gDNA, or cDNA) or gene product (e.g., mRNA or expressed protein) by the test compound(s). Alternatively, the assay can detect inhibition of the characteristic protease activity of the MT-SP1 gene product. High throughput assays for the presence, absence, or quantification of particular nucleic acids or protein products are well known to those of skill in the art. Similarly, binding assays are similarly well known. Thus, for example, U.S. Pat. No. 5,559,410 discloses high throughput screening methods for proteins, U.S. Pat. No. 5,585,639 discloses high throughput screening methods for nucleic acid binding (i.e., in arrays), while U.S. Pat. Nos. 5,576,220 and 5,541,061 disclose high throughput methods of screening for ligand/antibody binding.

In addition, high throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols the various high throughput. Thus, for example, Zymark Corp. provides technical bulletins describing screening systems for detecting the modulation of gene transcription, ligand binding, and the like.

VI. Assay Optimization.

The assays of this invention have immediate utility in detecting elevated expression and/or activity of an MT-SP1 protease or for screening for agents that modulate the MT-SP1 activity of a cell, tissue or organism. The assays of this invention can be optimized for use in particular contexts, depending, for example, on the source and/or nature of the biological sample and/or the particular test agents, and/or the analytic facilities available.

Thus, for example, optimization can involve determining optimal conditions for binding assays, optimum sample processing conditions (e.g. preferred PCR conditions), hybridization conditions that maximize signal to noise, protocols that improve throughput, etc. In addition, assay formats can be selected and/or optimized according to the availability of equipment and/or reagents. Thus, for example, where commercial antibodies or ELISA kits are available it may be desired to assay protein concentration. Conversely, where it is desired to screen for modulators that alter transcription of one or more of the genes or ESTs identified herein, nucleic acid based assays are preferred.

Routine selection and optimization of assay formats is well known to those of ordinary skill in the art.

VII. MT-SP1-Targeted Therapeutics.

Since MT-SP1 is found in a cell membrane, it can be exploited as target for the efficient and specific delivery of an effector (e.g. an effector molecule such as a cytotoxin, a radiolabel, etc.) to a cell expressing MT-SP1. In one preferred embodiment, chimeric molecules are used to deliver the effector to the cancer cell (or proliferating endothelial cell participating in angiogeneisis).

In a chimeric molecule, two or more molecules that exist separately in their native state are joined together to form a single molecule having the desired functionality of all of its constituent molecules. Typically, one of the constituent molecules of a chimeric molecule is a "targeting molecule". The targeting molecule is a molecule such as a ligand or an antibody that specifically binds to its corresponding target, in this case an MT-SP1 protein.

Another constituent of the chimeric molecule is an "effector". The effector molecule refers to a molecule or group of molecules that is to be specifically transported to the target cell (e.g., a cell expressing an MT-SP1 polypeptide). The effector molecule typically has a characteristic activity that is desired to be delivered to the target cell. Effector molecules include, but are not limited to cytotoxins, labels, radionuclides, ligands, antibodies, drugs, liposomes, and the like.

In particular, where the effector component is a cytotoxin, the chimeric molecule may act as a potent cell-killing agent specifically targeting the cytotoxin to cells bearing a particular target molecule. For example, chimeric fusion proteins which include interleukin 4 (IL-4) or transforming growth factor (TGFα) fused to *Pseudomonas* exotoxin (PE) or interleukin 2 (IL-2) fused to *Diphtheria* toxin (DT) have been shown to specifically target and kill cancer cells (Pastan et al., *Ann. Rev. Biochem.,* 61: 331–354 (1992)).

A) The Targeting Molecule.

In a preferred embodiment, in the methods and compositions of this invention, the targeting molecule is an antibody that specifically binds to a MT-SP1 protein or to a fragment thereof. The antibody can be a full-length antibody polyclonal or monoclonal, an antibody fragment (e.g. Fv, Fab, etc.), or a single chain antibody (e.g. scFv).

The antibody can be produced according to standar methods well known to those of skill in the art as described above. The antibody once produced can be chemically conjugated to the effector.

Where one of the effector molecule(s) is a protein, the antibody can be a single chain antibody and the chimeric molecule can be a recombinantly expressed fusion protein.

Means of producing such recombinant fusion proteins are well known to those of skill in the art.

B) The Effector Molecule.

As described above, the effector molecule component of the chimeric molecules of this invention may be any molecule whose activity it is desired to deliver to cells that express or overexpress a MT-SP1 protein. Particularly preferred effector molecules include cytotoxins such as *Pseudomonas* exotoxin, or *Diphtheria* toxin, radionuclides, radio-sensitizing agents, ligands such as growth factors, antibodies, detectable labels such as fluorescent, radio-opaque, or radioactive labels, and therapeutic compositions such as liposomes and various drugs.

1) Cytotoxins.

Particularly preferred cytotoxins include *Pseudomonas* exotoxins, *Diphtheria* toxins, ricin, and abrin. *Pseudomonas* exotoxin and *Dipthteria* toxin are most preferred.

*Pseudomonas* exotoxin A (PE) is an extremely active monomeric protein (molecular weight 66 kD), secreted by *Pseudomonas aeruginosa*, which inhibits protein synthesis in eukaryotic cells through the inactivation of elongation factor 2 (EF-2) by catalyzing its ADP-ribosylation (catalyzing the transfer of the ADP ribosyl moiety of oxidized NAD onto EF-2).

The toxin contains three structural domains that act in concert to cause cytotoxicity. Domain Ia (amino acids 1–252) mediates cell binding. Domain II (amino acids 253–364) is responsible for translocation into the cytosol and domain III (amino acids 400–613) mediates ADP ribosylation of elongation factor 2, which inactivates the protein and causes cell death. The function of domain Ib (amino acids 365–399) remains undefined, although a large part of it, amino acids 365–380, can be deleted without loss of cytotoxicity. See Siegall et al., *J. Biol. Chem.* 264: 14256–14261 (1989).

Where the targeting molecule (e.g. anti-MT-SP1) is fused to PE, a preferred PE molecule is one in which domain Ia (amino acids 1 through 252) is deleted and amino acids 365 to 380 have been deleted from domain Ib. However all of domain Ib and a portion of domain II (amino acids 350 to 394) can be deleted, particularly if the deleted sequences are replaced with a linking peptide such as GGGGS (SEQ ID NO:77).

In addition, the PE molecules can be further modified using site-directed mutagenesis or other techniques known in the art, to alter the molecule for a particular desired application. Means to alter the PE molecule in a manner that does not substantially affect the functional advantages provided by the PE molecules described here can also be used and such resulting molecules are intended to be covered herein.

For maximum cytotoxic properties of a preferred PE molecule, several modifications to the molecule are recommended. An appropriate carboxyl terminal sequence to the recombinant molecule is preferred to translocate the molecule into the cytosol of target cells. Amino acid sequences which have been found to be effective include, REDLK (SEQ ID NO:78) (as in native PE), REDL (SEQ ID NO:79) RDEL (SEQ ID NO:80), or KDEL (SEQ ID NO:81), repeats of those, or other sequences that function to maintain or recycle proteins into the endoplasmic reticulum, referred to here as "endoplasmic retention sequences". See, for example, Chaudhary et al. (1991) *Proc. Natl. Acad. Sci. USA* 87:308–312 and Seetharam et al, *J. Biol. Chem.* 266: 17376–17381. Preferred forms of PE comprise the PE molecule designated PE38QQR. (Debinski et al. *Bioconj.*

*Chem.*, 5: 40 (1994)), and PE4E (see, e.g., Chaudhary et al. (1995) *J. Biol. Chem.*, 265: 16306). The targeting molecule (e.g. anti-MT-SP1) may also be inserted at a point within domain III of the PE molecule or into domain Ib. Methods of cloning genes encoding PE fused to various ligands are well known to those of skill in the art (see, e.g., Siegall et al., *FASEB J.*, 3: 2647–2652 (1989); and Chaudhary et al. *Proc. Natl. Acad. Sci. USA*, 84: 4538–4542 (1987)).

Like PE, diphtheria toxin (DT) kills cells by ADP-ribosylating elongation factor 2 thereby inhibiting protein synthesis. *Diphtheria* toxin, however, is divided into two chains, A and B, linked by a disulfide bridge. In contrast to PE, chain B of DT, which is on the carboxyl end, is responsible for receptor binding and chain A, which is present on the amino end, contains the enzymatic activity (Uchida et al., *Science*, 175: 901–903 (1972); Uchida et al. *J. Biol. Chem.*, 248: 3838–3844 (1973)).

In a preferred embodiment, the targeting molecule-*Diphtheria* toxin fusion proteins of this invention have the native receptor-binding domain removed by truncation of the *Diphtheria* toxin B chain. Particularly preferred is DT388, a DT in which the carboxyl terminal sequence beginning at residue 389 is removed. Chaudhary, et al., *Bioch. Biophys. Res. Comm.*, 180: 545–551 (1991). Like the PE chimeric cytotoxins, the DT molecules may be chemically conjugated to the MT-SP1 antibody, but, in a preferred embodiment, the targeting molecule will be fused to the *Diphtheria* toxin by recombinant means (see, e.g., Williams et al. (1990) *J. Biol. Chem.* 265: 11885–11889).

2) Detectable Labels.

Detectable labels suitable for use as the effector molecule component of the chimeric molecules of this invention include any composition detectable by spectroscopic, photochemical, biochemical, immunochemical, electrical, optical or chemical means. Useful labels in the present invention include magnetic beads (e.g. Dynabeads™), fluorescent dyes (e.g., fluorescein isothiocyanate, texas red, rhodamine, green fluorescent protein, and the like), radiolabels (e.g., $^{3}$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic (e.g. polystyrene, polypropylene, latex, etc.) beads.

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

3) Ligands.

The effector molecule may also be a ligand or an antibody. Particularly preferred ligand and antibodies are those that bind to surface markers on immune cells. Chimeric molecules utilizing such antibodies as effector molecules act as bifunctional linkers establishing an association between the immune cells bearing binding partner for the ligand or antibody and the tumor cells expressing the MT-SP1 protein. Suitable antibodies and growth factors are known to those of skill in the art and include, but are not limited to, IL-2, IL-4, IL-6, IL-7, tumor necrosis factor (TNF), anti-Tac, TGFα, and the like.

4) Other Therapeutic Moieties.

Other suitable effector molecules include pharmacological agents or encapsulation systems containing various pharmacological agents. Thus, the targeting molecule of the chimeric molecule may be attached directly to a drug that is to be delivered directly to the tumor. Such drugs are well known to those of skill in the art and include, but are not limited to, doxirubicin, vinblastine, genistein, an antisense molecule, and the like.

Alternatively, the effector molecule may be an encapsulation system, such as a viral capsid, a liposome, or micelle that contains a therapeutic composition such as a drug, a nucleic acid (e.g. an antisense nucleic acid), or another therapeutic moiety that is preferably shielded from direct exposure to the circulatory system. Means of preparing liposomes attached to antibodies are well known to those of skill in the art. See, for example, U.S. Pat. No. 4,957,735, Connor et al., *Pharm. Ther.*, 28: 341–365 (1985)

C) Attachment of the Targeting Molecule to the Effector Molecule.

One of skill will appreciate that the MT-SP1 targeting molecule and effector molecules may be joined together in any order. Thus, where the targeting molecule is a polypeptide, the effector molecule may be joined to either the amino or carboxy termini of the targeting molecule. The targeting molecule may also be joined to an internal region of the effector molecule, or conversely, the effector molecule may be joined to an internal location of the targeting molecule, as long as the attachment does not interfere with the respective activities of the molecules.

The targeting molecule and the effector molecule may be attached by any of a number of means well known to those of skill in the art. Typically the effector molecule is conjugated, either directly or through a linker (spacer), to the targeting molecule. However, where both the effector molecule and the targeting molecule are polypeptides it is preferable to recombinantly express the chimeric molecule as a single-chain fusion protein.

1) Conjugation of the Effector Molecule to the Targeting Molecule.

In one embodiment, the targeting molecule (e.g., anti-MT-SP1Ab) is chemically conjugated to the effector molecule (e.g., a cytotoxin, a label, a ligand, or a drug or liposome). Means of chemically conjugating molecules are well known to those of skill.

The procedure for attaching an agent to an antibody or other polypeptide targeting molecule will vary according to the chemical structure of the agent. Polypeptides typically contain variety of functional groups; e.g., carboxylic acid (COOH) or free amine (—NH$_2$) groups, which are available for reaction with a suitable functional group on an effector molecule to bind the effector thereto.

Alternatively, the targeting molecule and/or effector molecule may be derivatized to expose or attach additional reactive functional groups. The derivatization may involve attachment of any of a number of linker molecules such as those available from Pierce Chemical Company, Rockford Ill.

A "linker", as used herein, is a molecule that is used to join the targeting molecule to the effector molecule. The linker is capable of forming covalent bonds to both the targeting molecule and to the effector molecule. Suitable linkers are well known to those of skill in the art and include, but are not limited to, straight or branched-chain carbon linkers, heterocyclic carbon linkers, or peptide linkers. Where the targeting molecule and the effector molecule are polypeptides, the linkers may be joined to the constituent amino acids through their side groups (e.g., through a disulfide linkage to cysteine). However, in a preferred embodiment, the linkers will be joined to the alpha carbon amino and carboxyl groups of the terminal amino acids.

A bifunctional linker having one functional group reactive with a group on a particular agent, and another group reactive with an antibody, may be used to form the desired immunoconjugate. Alternatively, derivatization may involve chemical treatment of the targeting molecule, e.g., glycol cleavage of the sugar moiety of a the glycoprotein antibody with periodate to generate free aldehyde groups. The free aldehyde groups on the antibody may be reacted with free amine or hydrazine groups on an agent to bind the agent thereto. (See U.S. Pat. No. 4,671,958). Procedures for generation of free sulfhydryl groups on polypeptide, such as antibodies or antibody fragments, are also known (See U.S. Pat. No. 4,659,839).

Many procedure and linker molecules for attachment of various compounds including radionuclide metal chelates, toxins and drugs to proteins such as antibodies are known (see, e.g., European Patent Application No. 188,256; U.S. Pat. Nos. 4,671,958, 4,659,839, 4,414,148, 4,699,784; 4,680,338; 4,569,789; and 4,589,071; and Borlinghaus et al. (1987) *Cancer Res.* 47: 4071–4075). In particular, production of various immunotoxins is well-known within the art and can be found, for example in "Monoclonal Antibody-Toxin Conjugates: Aiming the Magic Bullet," Thorpe et al., *Monoclonal Antibodies in Clinical Medicine*, Academic Press, pp. 168–190 (1982), Waldmann (1991) *Science*, 252: 1657, U.S. Pat. Nos. 4,545,985 and 4,894,443.

In some circumstances, it is desirable to free the effector molecule from the targeting molecule when the chimeric molecule has reached its target site. Therefore, chimeric conjugates comprising linkages which are cleavable in the vicinity of the target site may be used when the effector is to be released at the target site. Cleaving of the linkage to release the agent from the antibody may be prompted by enzymatic activity or conditions to which the immunoconjugate is subjected either inside the target cell or in the vicinity of the target site. When the target site is a tumor, a linker which is cleavable under conditions present at the tumor site (e.g. when exposed to tumor-associated enzymes or acidic pH) may be used.

A number of different cleavable linkers are known to those of skill in the art. See U.S. Pat. Nos. 4,618,492; 4,542,225, and 4,625,014. The mechanisms for release of an agent from these linker groups include, for example, irradiation of a photolabile bond and acid-catalyzed hydrolysis. U.S. Pat. No. 4,671,958, for example, includes a description of immunoconjugates comprising linkers which are cleaved at the target site in vivo by the proteolytic enzymes of the patient=s complement system. In view of the large number of methods that have been reported for attaching a variety of radiodiagnostic compounds, radiotherapeutic compounds, drugs, toxins, and other agents to antibodies one skilled in the art will be able to determine a suitable method for attaching a given agent to an antibody or other polypeptide.

2) Production of Fusion Proteins.

Where the MT-SP1 targeting molecule and/or the effector molecule is relatively short (i.e., less than about 50 amino acids) they may be synthesized using standard chemical peptide synthesis techniques. Where both molecules are relatively short the chimeric molecule may be synthesized as a single contiguous polypeptide. Alternatively the targeting molecule and the effector molecule may be synthesized separately and then fused by condensation of the amino terminus of one molecule with the carboxyl terminus of the other molecule thereby forming a peptide bond. Alternatively, the targeting and effector molecules may each be condensed with one end of a peptide spacer molecule thereby forming a contiguous fusion protein.

Solid phase synthesis in which the C-terminal amino acid of the sequence is attached to an insoluble support followed by sequential addition of the remaining amino acids in the sequence is the preferred method for the chemical synthesis of the polypeptides of this invention. Techniques for solid phase synthesis are described by Barany and Merrifield, Solid-Phase Peptide Synthesis; pp. 3–284 in *The Peptides: Analysis, Synthesis, Biology. Vol.* 2: *Special Methods in Peptide Synthesis, Part A.*, Merrifield, et al. *J. Am. Chem. Soc.*, 85: 2149–2156 (1963), and Stewart et al., *Solid Phase Peptide Synthesis,* 2nd ed. Pierce Chem. Co., Rockford, Ill. (1984).

In a preferred embodiment, the chimeric fusion proteins of the present invention are synthesized using recombinant DNA methodology. Generally this involves creating a DNA sequence that encodes the fusion protein, placing the DNA in an expression cassette under the control of a particular promoter, expressing the protein in a host, isolating the expressed protein and, if required, renaturing the protein.

DNA encoding the fusion proteins (e.g. anti-MT-SP1-PE38QQR) of this invention may be prepared by any suitable method, including, for example, cloning and restriction of appropriate sequences or direct chemical synthesis by methods such as the phosphotriester method of Narang et al. *Meth. Enzymol.* 68: 90–99 (1979); the phosphodiester method of Brown et al., *Meth. Enzymol.* 68: 109–151 (1979); the diethylphosphoramidite method of Beaucage et al., *Tetra. Lett.,* 22: 1859–1862 (1981); and the solid support method of U.S. Pat. No. 4,458,066.

Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences.

Alternatively, subsequences may be cloned and the appropriate subsequences cleaved using appropriate restriction enzymes. The fragments may then be ligated to produce the desired DNA sequence.

n a preferred embodiment, DNA encoding fusion proteins of the present invention may be cloned using DNA amplification methods such as polymerase chain reaction (PCR). Thus, for example, the nucleic acid encoding an anti-MT-SP1 is PCR amplified, using a sense primer containing the restriction site for NdeI and an antisense primer containing the restriction site for HindIII. This produces a nucleic acid encoding the anti-MT-SP1 sequence and having terminal restriction sites. A PE38QQR fragment may be cut out of the plasmid pWDMH4-38QQR or plasmid pSGC242FdN1 described by Debinski et al. (1994) *Int. J. Cancer,* 58: 744–748. Ligation of the anti-MT-SP1 and PE38QQR sequences and insertion into a vector produces a vector encoding anti-MT-SP1 joined to the amino terminus of PE38QQR (position 253 of PE). The two molecules are joined by a three amino acid junction consisting of glutamic acid, alanine, and phenylalanine introduced by the restriction site.

While the two molecules are preferably essentially directly joined together, one of skill will appreciate that the molecules may be separated by a peptide spacer consisting of one or more amino acids. Generally the spacer will have no specific biological activity other than to join the proteins or to preserve some minimum distance or other spatial relationship between them. However, the constituent amino acids of the spacer may be selected to influence some property of the molecule such as the folding, net charge, or hydrophobicity.

The nucleic acid sequences encoding the fusion proteins may be expressed in a variety of host cells, including *E. coli*, other bacterial hosts, yeast, and various higher eukaryotic cells such as the COS, CHO and HeLa cells lines and myeloma cell lines. The recombinant protein gene will be operably linked to appropriate expression control sequences for each host. For *E. coli* this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

The plasmids of the invention can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant fusion proteins can be purified according to standard procedures of the art, including ammonium sulfate precipitation, affinity columns, column chromatography, gel electrophoresis and the like (see, generally, R. Scopes, *Protein Purification*, Springer-Verlag, N.Y. (1982), Deutscher, *Methods in Enzymology Vol. 182: Guide to Protein Purification.*, Academic Press, Inc. N.Y. (1990)). Substantially pure compositions of at least about 90 to 95% homogeneity are preferred, and 98 to 99% or more homogeneity are most preferred for pharmaceutical uses. Once purified, partially or to homogeneity as desired, the polypeptides may then be used therapeutically.

One of skill in the art would recognize that after chemical synthesis, biological expression, or purification, the MT-SP1 targeted fusion protein may possess a conformation substantially different than the native conformations of the constituent polypeptides. In this case, it may be necessary to denature and reduce the polypeptide and then to cause the polypeptide to re-fold into the preferred conformation. Methods of reducing and denaturing proteins and inducing re-folding are well known to those of skill in the art (See, Debinski et al. (1993) *J. Biol. Chem.*, 268: 14065–14070; Kreitman and Pastan (1993) *Bioconjug. Chem.*, 4: 581–585; and Buchner, et al. (1992) *Anal. Biochem.*, 205: 263–270).

One of skill would recognize that modifications can be made to the MT-SP1 targeted fusion proteins without diminishing their biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids placed on either terminus to create conveniently located restriction sites or termination codons.

D) Pharmaceutical Compositions.

The chimeric molecules of this invention are useful for parenteral, topical, oral, or local administration (e.g. injected into a tumor site), aerosol administration, or transdermal administration, for prophylactic, but principly for therapeutic treatment. The pharmaceutical compositions can be administered in a variety of unit dosage forms depending upon the method of administration. For example, unit dosage forms suitable for oral administration include powder, tablets, pills, capsules and lozenges. It is recognized that the fusion proteins and pharmaceutical compositions of this invention, when administered orally, must be protected from digestion. This is typically accomplished either by complexing the protein with a composition to render it resistant to acidic and enzymatic hydrolysis or by packaging the protein in an appropriately resistant carrier such as a liposome. Means of protecting proteins from digestion are well known in the art.

The pharmaceutical compositions of this invention are particularly useful for parenteral administration, such as intravenous administration or administration into a body cavity or lumen of an organ. The compositions for administration will commonly comprise a solution of the chimeric molecule dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of chimeric molecule in these formulations can vary widely, and will be selected primarily based on fluid volumes, viscosities, body weight and the like in accordance with the particular mode of administration selected and the patient's needs.

Thus, a typical pharmaceutical composition for intravenous administration would be about 0.1 to 10 mg per patient per day. Dosages from 0.1 up to about 100 mg per patient per day may be used, particularly when the drug is administered to a secluded site and not into the blood stream, such as into a body cavity or into a lumen of an organ. Actual methods for preparing parenterally administrable compositions will be known or apparent to those skilled in the art and are described in more detail in such publications as *Remington's Pharmaceutical Science*, 15th ed., Mack Publishing Company, Easton, Pa. (1980).

The compositions containing the present fusion proteins or a cocktail thereof (i.e., with other proteins) can be administered for therapeutic treatments. In therapeutic applications, compositions are administered to a patient suffering from a disease, e.g., a cancer, in an amount sufficient to cure or at least partially arrest the disease and its complications. An amount adequate to accomplish this is defined as a "therapeutically effective dose." Amounts effective for this use will depend upon the severity of the disease and the general state of the patient's health.

Single or multiple administrations of the compositions may be administered depending on the dosage and frequency as required and tolerated by the patient. In any event, the composition should provide a sufficient quantity of the proteins of this invention to effectively treat the patient.

It will be appreciated by one of skill in the art that there are some regions that are not heavily vascularized or that are protected by cells joined by tight junctions and/or active transport mechanisms which reduce or prevent the entry of macromolecules present in the blood stream. Thus, for example, systemic administration of therapeutics to treat gliomas, or other brain cancers, is constrained by the blood-brain barrier which resists the entry of macromolecules into the subarachnoid space.

One of skill in the art will appreciate that in these instances, the therapeutic compositions of this invention can be administered directly to the tumor site. Thus, for example, brain tumors (e.g., gliomas) can be treated by administering the therapeutic composition directly to the tumor site (e.g., through a surgically implanted catheter). Where the fluid delivery through the catheter is pressurized, small molecules (e.g. the therapeutic molecules of this invention) will typically infiltrate as much as two to three centimeters beyond the tumor margin.

Alternatively, the therapeutic composition can be placed at the target site in a slow release formulation. Such formulations can include, for example, a biocompatible sponge or other inert or resorbable matrix material impregnated with the therapeutic composition, slow dissolving time release capsules or microcapsules, and the like.

Typically the catheter or time release formulation will be placed at the tumor site as part of a surgical procedure. Thus, for example, where major tumor mass is surgically removed, the perfusing catheter or time release formulation can be emplaced at the tumor site as an adjunct therapy. Of course, surgical removal of the tumor mass may be undesired, not required, or impossible, in which case, the delivery of the therapeutic compositions of this invention may comprise the primary therapeutic modality.

E) Tumor Imaging and Radio-Sensitizing Compositions.

1) Imaging Compositions.

In certain embodiments, the chimeric molecules of this invention can be used to direct detectable labels to a tumor site. This can facilitate tumor detection and/or localization. In a particularly preferred embodiment, the effector compoent of the chimeric molecule is a "radiopaque" label, e.g. a label that can be easily visualized using x-rays. Radiopaque materials are well known to those of skill in the art. The most common radiopaque materials include iodide, bromide or barium salts. Other radiopaque materials are also known and include, but are not limited to organic bismuth derivatives (see, e.g., U.S. Pat. No. 5,939,045), radiopaque polyurethanes (see U.S. Pat. No. 5,346,9810, organobismuth composites (see, e.g., U.S. Pat. No. 5,256,334), radiopaque barium polymer complexes (see, e.g., U.S. Pat. No. 4,866,132), and the like.

The anti-MT-SP1 antibodie(s) can be coupled directly to the radiopaque moiety or they can be attached to a "package" (e.g. a liposome, a polymer microbead, etc.) carrying or containing the radiopaque material.

2) Radiosensitizers.

In another embodiment, the effector can be a radiosensitizer that enhances the cytotoxic effect of ionizing radiation (e.g., such as might be produced by $^{60}$Co or an x-ray source) on a cell. Numerous radiosensitizing agents are known and include, but are not limited to benzoporphyrin derivative compounds (see, e.g., U.S. Pat. No. 5,945,439), 1,2,4-benzotriazine oxides (see, e.g., U.S. Pat. No. 5,849,738), compounds containing certain diamines (see, e.g., U.S. Pat. No. 5,700,825), BCNT (see, e.g., U.S. Pat. No. 5,872,107), radiosensitizing nitrobenzoic acid amide derivatives (see, e.g., U.S. Pat. No. 4,474,814), various heterocyclic derivatives (see, e.g., U.S. Pat. No. 5,064,849), platinum complexes (see, e.g., U.S. Pat. No. 4,921,963), and the like.

The anti-MT-SP1 antibodie(s) can be coupled directly to the radiopaque moiety or they can be attached to a "package" (e.g. a liposome, a polymer microbead, etc.) carrying or containing the radiosensitizing material.

VIII. Kits.

In still another embodiment, this invention provides kits for practice of the assays or use of the therapeutics and/or diagnostics described herein. In one preferred embodiment, the kits comprise one or more containers containing antibodies and/or nucleic acid probes and/or substrates suitable for detection of MT-SP1 proteins or protein fragments, and/or MT-SP1 nucleic acid(s), and/or and MT-SP1 protein activity, respectively. In other embodiments; the kits include one or more of the MT-SP1 directed chimeric molecules discussed herein. The kits may optionally include any reagents and/or apparatus to facilitate practice of the assays or delivery of the molecules described herein. Such reagents include, but are not limited to buffers, pharmacological excipients, labels, labeled antibodies, labeled nucleic acids, filter sets for visualization of fluorescent labels, blotting membranes, and the like.

In addition, the kits may include instructional materials containing directions (i.e., protocols) for the practice of the assay methods or use of the chimeric molecules of this invention. Preferred instructional materials provide protocols for assaying MT-SP1 gene expression, and/or protein levels, and/or MT-SP1 protein activity, while other preferred instructional materials provide guidance and instructions for the use of the chimeric molecules described herein. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Reverse Biochemistry: Using Macromolecular Protease Inhibitors to Identify a Membrane-Type Serine Protease in Epithelial Cancer and Normal Tissue This example describes the use of a "fold-specific" inhibitor$^{(i, ii)}$ in studying the role of these chymotrypsin-fold serine proteases in cancer. Ecotin or engineered versions of ecotin are introduced into complex biological systems as probes of proteolysis by these chymotrypsin-fold proteases. When, as demonstrated herein, effects are observed upon treatment with these unique inhibitors, then the large body of knowledge concerning the biochemistry of these proteases can be tapped to understand the structure and function of the target proteases.

For example, the molecular cloning, structural modeling, and mechanistic understanding of the enzymes are immediately accessible. Analogous to "reverse genetics" we refer to this approach as "reverse biochemistry" and have applied it to identify specific serine proteases in prostate cancer.

One useful model system for studying many issues that are pertinent to prostate cancer is the development of the rodent ventral prostate (VP) in explant cultures. Macromolecular inhibitors of serine proteases of the chymotrypsin fold, ecotin and ecotin M84R/M85R (see copending application Ser. Nos. 09/290,513 and 09/289,830, both filed on Apr. 12, 1999), inhibit ductal branching morphogenesis and differentiation of the explanted rat VP. Ecotin M84R/M85R is an 2800-fold more potent inhibitor of uPA compared to ecotin (1 nM and 2.8 µM respectively). However, inhibition of prostate differentiation was seen with both inhibitors, suggesting that uPA and other related serine proteases are involved in the differentiation and continued growth of the rat VP. Thus unidentified serine proteases may play a role in growth and prevention of apoptosis in prostate epithelial cells in this system.

Another well characterized model that is derived from human prostate cancer epithelial cells is the PC-3 cell line (Kaighn et al. (1979) Invest. Urology 17: 16–23). The PC-3 cell line expresses uPA as assayed by enzyme-linked immunosorbent assay (ELISA) and by Northern blotting of PC-3 mRNA (Yoshida et al. (1994) Cancer Res. 54: 3300–3304). We found that the primary tumor size in PC-3 implanted nude mice was significantly smaller in ecotin M84R/M85R and ecotin wild-type treated mice treated for seven weeks compared to the primary tumor size of PBS-treated mice after four weeks. Metastasis from the primary tumors similarly were similarly lower in the inhibitor-treated mice compared to PBS treated mice. Inhibition was not unexpected with ecotin M84R/M85R treatment, since uPA has been implicated in metastasis. However, wild-type ecotin is a poor, micromolar inhibitor of uPA; one interpretation of the data is that the decrease in tumor size and metastasis in the mouse model involves the inhibition of additional serine proteases. Thus identification of the serine proteases expressed by PC-3 prostate cells may provide insight into the role of these proteases in cancer and prostate growth and development. In this example we have extended the strategy of using the polymerase chain reaction (PCR) with degenerate oligonucleotide primers that were designed using conserved sequence homology (Sakanari et al. (1989) Proc. Natl. Acad. Sci. USA 86: 4863–4867; Wiegand et al. (1993) Gene 136: 167–175, Kang et al. (1992) Gene 110: 181–187) to identify additional serine proteases made by cancer cells. Five independent serine protease cDNAs derived from PC-3 mRNA were sequenced, including a novel serine protease, which we refer to as membrane-type serine protease 1 (MT-SP1), and the cloning and characterization of this cDNA that encodes a mosaic, transmembrane protease is reported.

Materials and Methods

Materials

All primers used were synthesized on a Applied Biosystems 391 DNA synthesizer. All restriction enzymes were purchased from New England Biolabs. Automated DNA sequencing was carried out on an Applied Biosystems 377 Prism sequencer, and manual DNA sequencing was carried out under standard conditions. N-terminal amino acid sequencing was performed on an ABI 477A by the Biomolecular resource center. The synthetic substrates, Suc-AAPX-pNA, [N-succinyl-alanyl-alanyl-prolyl-Xxx-pNA (Xxx=alanyl, aspartyl, glutamyl, phenylalanyl, leucinyl, methionyl, and arginyl)], and H-Arg-pNA, (arginyl-pNA), were purchased from Bachem. Deglycosylation was performed using PNGase F (NEB). All other reagents were of the highest quality available and purchased from Sigma or Fisher unless otherwise noted.

Isolation of cDNA from PC-3 Cells mRNA was isolated from PC-3 cells using the polyAT-tract System 1000 kit (Promega). Reverse transcription was primed using the "lock-docking" oligo dT primer (Borsont et al. (1992) PCR Meth. Appl. 2: 144–148). Superscript II reverse transcriptase (Life Technologies) was used in accordance with the manufacturer's instructions to synthesize the cDNA from the PC-3 mRNA.

Amplification of MT-SP1 Gene

The degenerate primers used for amplifying the protease domains were designed from the consensus sequences flanking the catalytic histidine (5' His-primer) and the catalytic serine (3' Ser-primer), similar to those described (Sakanari et al. (1989) Proc. Natl. Acad. Sci. USA 86, 4863–4867). The 5' primer used is as follows: 5'-TGG (AG)TI (CAG)TI (AT)(GC)I GCI (GA)CI CA(CT) TG-3' (SEQ ID NO: 3), where nucleotides in parentheses represent equimolar mixtures, and I represents deoxyinosine. This primer encodes at least the following amino acid sequence: W (I/V) (I/V/L/M) (S/T) A (A/T) H C (SEQ ID NO: 4). The 3' primer used is as follows: 5'-IGG ICC ICC I(GC)(AT) (AG)TC ICC (CT) TI (GA)CA IG(ATC) (GA)TC-3' (SEQ ID NO: 5). The reverse complement of the 3' primer encodes at least the following amino acid sequence: D (A/SIT) C (K/E/Q/H) G D S G G P (SEQ ID NO: 6).

Direct amplification of serine protease cDNA was not possible using the above primers. Instead, the first PCR was performed with the 5'-His-primer and the oligo dT primer described above, using the "touchdown" PCR protocol (Don et al. (1991) Nucleic Acids Res. 19: 4008), with annealing temperatures decreasing from 52° C. to 42° C. over 22 rounds, and 13 final rounds at 54° C. annealing temperature. Cycle times were 1 minute denaturing, 1 minute annealing, and 2 minute extension times, followed by one final extension time of 15 minutes after the final round of PCR. The template for the second PCR was 0.5 µL (total reaction volume 50 µL) of a 1 to 10 dilution of the first PCR reaction mixture that was performed with the 5' His-primer and the oligo dT. The second PCR reaction was primed with the 5' His and the 3' Ser-primers and performed using the touchdown protocol described above. All PCR reactions used 12.5 pmol of primer for 50 µL reaction volume.

The product of the second reaction was purified on a 2% agarose gel, and all products between 400 and 550 base pairs were cut from the gel and extracted using the Qiaquick gel extraction kit (Qiagen). These products were digested with the BamHI restriction enzyme to cut any uPA cDNA, and all 400–500 bp fragments were repurified on a 2% agarose gel. These reaction products were subjected to a third PCR using the 5' His-primer and the 3' Ser-primer using the identical touchdown procedure. These reaction products were gel purified and directly cloned into the pPCR2.1 vector using the TOPO TA ligation kit (Invitrogen). DNA sequencing of the inserts determined the cDNA sequence from nucleotides 1984–2460, see FIG. 1.

Northern Blot Analysis $^{32}$P-Labeled nucleotides were purchased from Amersham Life Sciences. A cDNA fragment containing nucleotides 1173–2510 was digested from EST w39209 using restriction enzymes EcoRI and BsmbI, yielding a 1.3 kb nucleotide insert. Labeled cDNA probes were synthesized using the Rediprime random primer labelling kit (Amersham) and 20 ng of the purified insert. Poly(A)+RNA membranes for Northern blotting were purchased from Origene (HB-1002, HB-1018) and Clontech (Human II #7759-1, Human Cancer Cell Line #7757). The blots were performed under stringent annealing conditions as described in (Ausubel et al. (ed.). (1990) Current protocols in molecular biology. Wiley & Sons, New York, N.Y.).

Construction of Expression Vectors

The mature protease domain and a small portion of the pro domain (nucleotides 1822–2601) cDNA were amplified using PCR from EST w39209 and ligated into the pQE30 vector (Qiagen). This construct is designed to overexpress the protease sequence from amino acids (aa) 596–855 with the following fusion: Met-Arg-Gly-Ser-His$_6$-(SEQ ID NO:82) aa596–855. The His-tag fusion allows affinity purification using ametal chelate chromatography. The change from Ser$^{805}$, encoded by TCC, to Ala (GCT) was performed using PCR. The presence of the correct Ser to Ala substitution in the pQE30 vector was verified by DNA sequence analysis.

Expression and Purification of the Protease Domain

The above-mentioned plasmids were separately transformed into *E. coli* X-90 to afford high-level expression of recombinant protease gene products (Evnin et al. (1990) *Proc. Natl. Acad. Sci. USA* 87, 6659–6663). Expression and purification of the recombinant enzyme from solubilized inclusion bodies was performed as described previously (Unal et al. (1997) *J. Virol.* 71, 7030–7038). Protein containing fractions were pooled and dialyzed overnight at 4° C. against 50 mM Tris pH 8, 10% glycerol, 1 mM □-mercaptoethanol, 3M urea. Autoactivation of the protease was monitored upon dialysis against storage buffer (50 mM Tris pH 8, 10% glycerol) at 4° C. using the substrate Spectrozyme tPA (hexahydrotyrosyl-Gly-Arg-pNA, American Diagnostica). Hydrolysis of Spectrozyme tPA was monitored at 405 nM for the formation of p-nitroaniline using a UVIKON 860 spectrophotometer. Activated protease was bound to an immobilized p-aminobenzamidine resin (Pierce) that had been equilibrated with storage buffer. Bound protease was eluted with 100 mM benzamidine and the protein containing fractions were pooled. Excess benzamidine was removed using FPLC with a Superdex 70 (Pharmacia) gel filtration column that was equilibrated with storage buffer. Protein containing fractions were pooled and stored at −80° C. The cleavage of the purified Ser$^{805}$Ala protease domain was performed at 37° C. by addition of active recombinant protease domain to 10 nM. Cleavage was monitored by SDS-PAGE.

Determination of Substrate Kinetics

The purified serine protease domain was titrated with 4-methylumbelliferyl p-guanidinobenzoate (MUGB) to obtain an accurate concentration of enzyme active sites$^{(iii)}$. Enzyme activity was monitored at 25° C. in assay buffer containing 50 mM Tris pH 8.8, 50 mM NaCl, and 0.01% Tween 20. The final concentration of substrate Spectrozyme tPA ranged from 1 µM–400 µM. Enzyme concentrations ranged from 40 pM–800 pM. Active site titrations were performed on a Fluoromax-2 spectrofluorimeter. Measurements were plotted using the KaleidaGraph program (Synergy, Reading, Pa.), and the $K_m$, $k_{cat}$, and $k_{cat}/K_m$ for Spectrozyme tPA was determined using the Michaelis-Menten equation.

Inhibition of MT-SP1 Protease Domain with Ecotin and Ecotin M84R/M85R

Ecotin and ecotin M84R/M85R were purified from *E. coli* as described in copending application Ser. Nos. 09/290,513 and 09/289,830, both filed on Apr. 12, 1999. Various concentrations of ecotin or ecotin M84R/M85R were incubated with the His-tagged serine protease domain in a total volume of 990 µL of buffer containing 50 mM NaCl, 50 mM Tris-HCl (pH 8.8), 0.01% Tween 20. 10 µL of Spectrozyme tPA was added, yielding a solution containing 100 µM substrate. The final enzyme concentration was 63 pM, and the ecotin and ecotin M84R/M85R concentration ranged from 0.1 nM to 50 nM. The data were fit to the equation derived for kinetics of reversible tight-binding inhibitors (Morrison (1969) *Biochim. Biophys. Acta* 185: 269–286, Williams and Morrison (1979) *Methods. Enzymol.* 63: 437–467), and the values for apparent $K^i$ were determined.

Results

Cloning of Serine Protease Domain cDNAs from PC-3 Cells and Amplification of MT-SP1 cDNA PCR amplification of serine protease cDNA was performed using "consensus cloning", where the amplification was performed with degenerate primers designed to anneal to cDNA encoding the region about the conserved catalytic histidine (5' His-primer) and the conserved catalytic serine (3' Ser-primer). The consensus primers were designed using 37 human sequences within a sequence alignment of 242 serine proteases of the chymotrypsin fold that are reported in the Swiss protein database. In order to bias the screen for previously unidentified proteases in the PC-3 cDNA, uPA cDNA was cut and removed using the known BamHI endonuclease site in the uPA cDNA sequence. The expected size of the cDNA fragments amplified between His$^{57}$ and Ser$^{195}$ cDNA (standard chymotrypsinogen numbering) is between 400–550 base pairs; statistically, only one in ten cDNAs of that length will be cleaved by BamHI. Thus, cDNAs obtained from the PCR reactions with the 5' His-primer and 3' Ser-primer were size selected for the 400–550 bp range, digested with BamHI and purified from any digested cDNAs. After a subsequent round of PCR, the products were cloned into pPCR2.1 (FIG. 2). Twenty clones were digested with EcoRI to monitor the size of the cDNA insert. Three clones lacked inserts of the correct size. The remaining seventeen clones containing inserts between 400 and 550 bp were sequenced. Blast searches of the resulting sequences revealed that six clones did not match serine protease sequences. The remaining cDNAs yielded clones corresponding to factor XII (2 clones), protein C (2 clones), trypsinogen type IV (2 clones), uPA (1 clone) and a cDNA denoted as membrane-type serine protease 1 (MT-SP1) (4 clones). Additional serine protease sequences may not have been found because they were digested by BamHI, lost in the size selection, or were present in lower frequencies.

Multiple EST sequences were found for the cDNA. EST accessions aa459076, aa219372, and w39209 were used extensively for sequencing the cDNA starting from nucleotide 746, and 2461–3142, but no start codon was observed. A sequence was also found in GenBank, accession no. U20428. This sequence also lacks the 5' end of the cDNA, but allowed amplification of cDNA from nucleotides 196–745. Rapid amplification of cDNA ends (RACE) techniques (Frohman (1993) *Methods Enzymol.* 218: 340–356) were used to obtain further 5' cDNA sequence. Application of RACE did not yield a clone containing the entire 5' untranslated region, but the sequence obtained contained a stop codon in frame with the Kozak start sequence (Kozak (1991) *J. Cell Biol.* 115: 887–903), giving confidence that the full coding sequence of the cDNA has been obtained. The nucleotide sequence and predicted amino acid sequence are shown in FIG. 1 (SEQ ID NO: 1 and 2).

Figure 3:
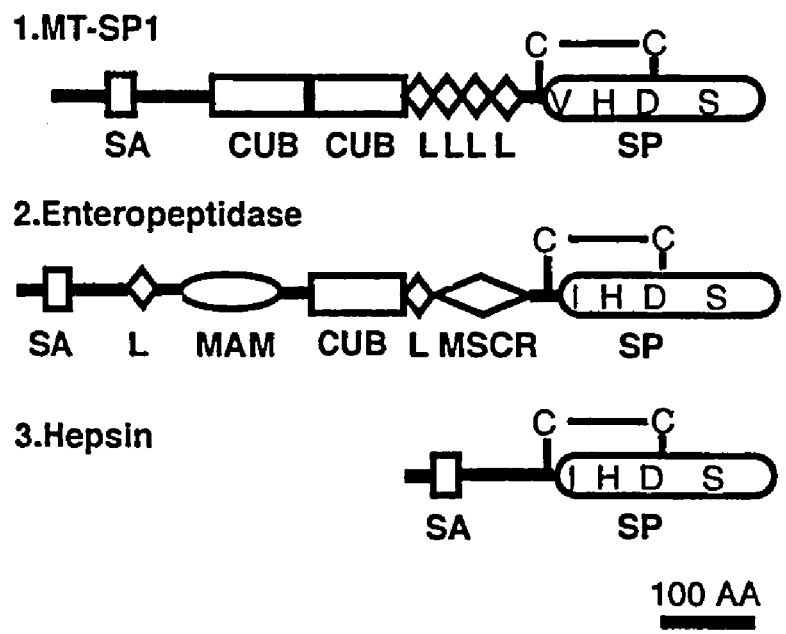
FIG. 3 shows the domain structure of human MT-SP1 compared with the domain structure of hepsin (Leytus et al. (1988) *Biochemistry* 27: 1067–1074) and enteropeptidase (Kitamoto et al. (1994) *Proc. Natl. Acad. Sci. USA* 91: 7588–7592). SA represents a possible signal anchor, CUB represents a repeat first identified in complement components C1r and C1s, the urchin embryonic growth factor and bone morphogenetic protein 1 (Bork and Beckmann (1993) *J. Mol. Biol.* 231: 539–545), L represents low-density lipoprotein receptor repeat (Krieger and Herz (1994) *Annu. Rev. Biochem.* 63: 601–637), SP represents a chymotrypsin family serine protease domain (Perona and Craik (1997) *J. Biol. Chem.* 272: 29987–29990), MAM represents a domain homologous to members of a family defined by meprin, protein A5, and the protein tyrosine phosphatase μ (Beckmann and Bork (1993) *Trends Biochem. Sci.* 18: 40–41), and MSCR represents a macrophage scavenger receptor cysteine-rich motif (Krieger and Herz (1994) *Annu. Rev. Biochem.* 63: 601–637). The predicted disulfide linkages are shown labeled as C—C.
Figure 4A:
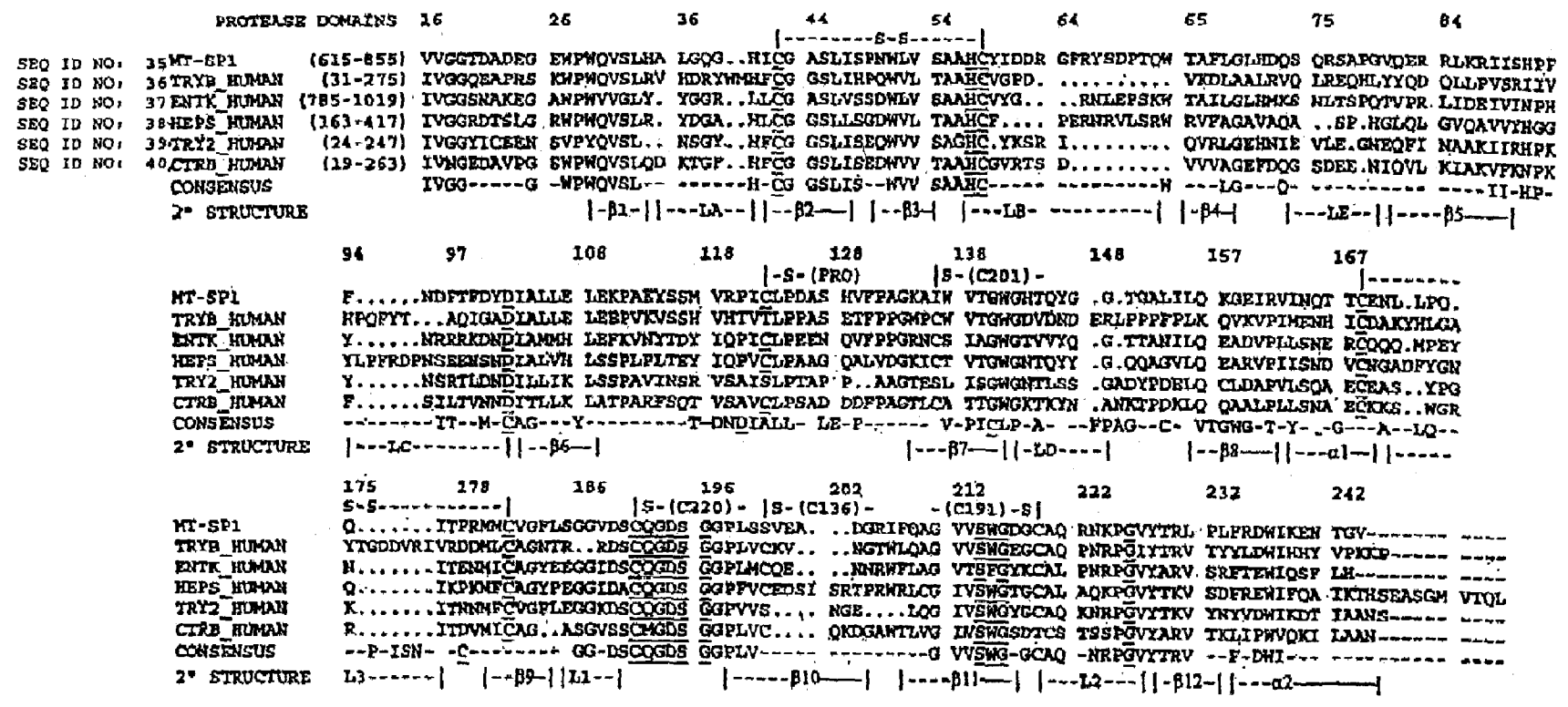
Figure 4C:
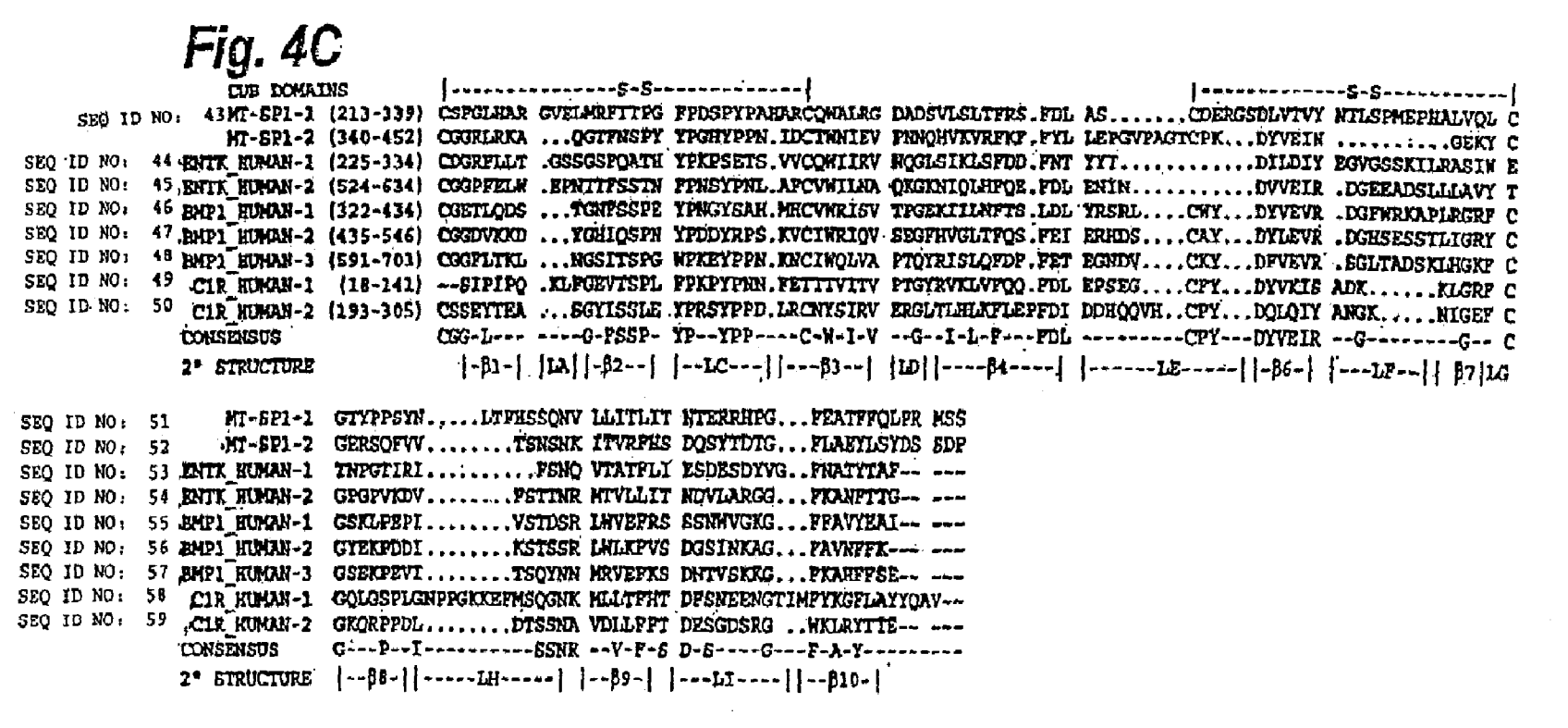

The nucleotide sequence surrounding the proposed start codon matches the optimal sequence of ACCATGG (SEQ ID NO: 7) for translation initiation sites proposed by Kozak (supra.). In addition, there is a stop codon in frame with the putative start codon, which gives further evidence that initiation occurs at that site. The DNA sequence predicts an 855 amino acid mosaic protein composed of multiple domains (FIG. 3). The coding sequence does not contain a typical signal peptide, but does contain a single hydrophobic sequence of 26 residues (residues 55–81), which is flanked by a charged residue on each side. This sequence may constitute a signal anchor (SA) sequence, similar to that observed in other proteases, including hepsin (Leytus et al. (1988) *Biochemistry* 27: 1067–1074) and enteropeptidase (Kitamoto et al. (1994) *Proc. Natl. Acad. Sci. USA* 91: 7588–7592). Following the putative SA sequence are two CUB domains (Bork and Beckmann (1993) *J. Mol. Biol.* 231: 539–545), which are named after the proteins in which the modules were first discovered: complement subcomponents C1s and C1r, urchin embryonic growth factor (Uegf), and bone morphogenetic protein 1 (BMP1). CUB domains have conserved characteristics, which include the presence of four cysteine residues and various conserved hydrophobic and aromatic positions (Bork and Beckmann (1993) *J. Mol. Biol.* 231: 539–545). The CUB domain, which has recently been characterized crystallographically (Varela et al. (1997) *J. Mol. Biol.* 274: 635–649), consists of ten □-strands that are organized into two 5-stranded β-sheets. Following the CUB domains are four LDLR repeats (Krieger and Herz (1994) *Annu. Rev. Biochem.* 63: 601–637), which are named after the receptor ligand-binding repeats that are present in the LDL receptor. These repeats have a highly conserved pattern and spacing of six cysteine residues that form three intramolecular disulfide bonds. The final domain observed is the serine protease domain. The alignments of these domains with other members of their respective classes are shown in FIG. 4.

Tissue Distribution of MT-SP1 mRNA.

Northern blots of human poly(A)+ RNA, using a 1.3 kB fragment of MT-SP1 cDNA fragment as a probe, show a ~3.3 kB fragment appearing in epithelial tissues including the prostate, kidney, spleen, liver, leukocytes, lung, small intestine, stomach, thymus, colon, and placenta, and explants of human breast cancer and mastases. This band was not observed in muscle, brain, ovary, or testis (FIG. 5). Similar experiments performed on a human cancer cell line blot shows that MT-SP1 is expressed in the Colorectal adenocarcinoma, SW480, and human breast cancer, but was not observed in the Promyelocytic Leukemia HL-60, HeLa Cell S3, Chronic Myelogenous Leukemia K-562, Lymphoblastic Leukemia MOLT-4, Burkitt's Lymphoma Raji, Lung Carcinoma A549, or Melanoma G361 lanes (data not shown). MT-SP1 is also expressed in blood vessels of prostatic and gastric cancers. This 3.3 kB mRNA fragment is slightly longer than the 3.1 kB sequence presented in FIG. 5, suggesting that there may still be further sequence in the 5′ untranslated region that has not been identified.

Activation and Purification of His-MT-SP1 Protease Domain

Figure 6A:
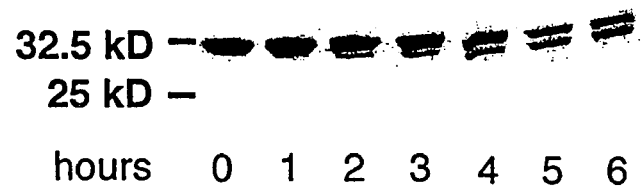
FIGS. 6A and 6B show activation and purification of His-tagged MT-SP1 protease domain. A representative experiment is shown in (FIG. 6A) and (FIG. 6B).
Figure 6B:
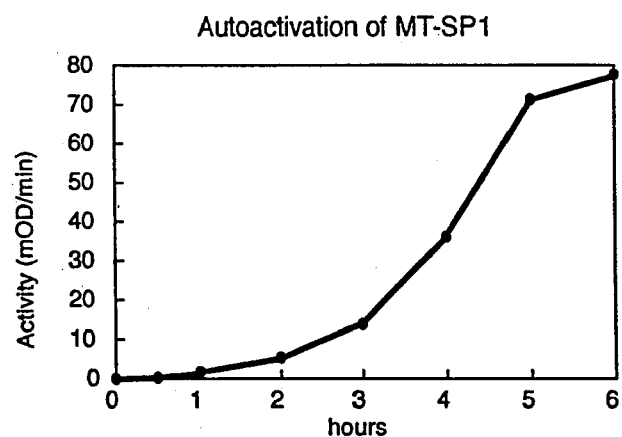
Figure 6C:
FIG. 6C: Inactive Ser$^{805}$Ala protease domain is cleaved with 10 nM activated His-tagged MT-SP1 protease domain at 37° C. The specific cleavage of active MT-SP1 protease domain is required for proper processing at the activation site. Active protease domain is shown in lane 7 (+), and no cleavage of the untreated inactive protease domain is observed (lane 8, -).

The serine protease domain of MT-SP1 was expressed in *E. coli* as a His-tagged fusion, and was purified from inclusion bodies under denaturing conditions using metal-chelate affinity chromatography. The yield of enzyme after this step was approximately 3 mg of protein per liter of *E. coli* culture. This denatured protein refolded when the urea was slowly dialyzed away from the protein. Surprisingly, the purified renatured protein showed a time dependent shift on an SDS-PAGE gel (FIG. 6A, lanes (a) 1–7), with the lower fragment being the size of the mature, processed enzyme, lacking the His tag. N-terminal sequencing of the purified, activated protease domain yielded the expected VVGGT (SEQ ID NO:83) activation sequence. When the refolded protein was tested for activity using the synthetic substrate hexahydrotyrosyl-glycyl-arginyl-paranitroanilide (Spectrozyme tPA), a time dependent increase in activity was observed (FIG. 6B). In contrast, the protease domain that contains the Ser$^{805}$Ala mutation did not either show a change in size on an SDS polyacrylamide gel or an increase in enzymatic activity under identical conditions (data not shown), suggesting that the catalytic serine is necessary for activation and not the result of a contaminating protease. In order to show that the cleavage of the protease domain was a result of His-tagged MT-SP1 protease activity, the inactive Ser$^{805}$Ala protease domain was treated with purified recombinant enzyme (FIG. 6C). This treatment results in the formation of a cleavage product that corresponds to the size of the active protease (FIG. 6C, lane 7). Untreated protease domain does not get cleaved (FIG. 6C, lane 8). From these results, it is concluded that the protease autoactivates upon refolding. The activated protease was separated from inactive protein and other contaminants using affinity chromatography with p-aminobenzamidine resin. Purified protein was analyzed by SDS-PAGE and no other contaminants were observed. Similarly, immunoblotting with polyclonal antiserum against purified protease domain (raised in rabbits at Berkeley Antibody Company) revealed one band. Under non-reducing conditions, the pro-region is disulfide linked to the protease domain; thus, this purified protein was also immunoreactive with the monoclonal antibody (Qiagen) directed against the amino-terminal Arg-Gly-Ser-His$_4$ (SEQ ID NO:34) epitope that is contained in the recombinant protease domain, further indicating the purity and identity of the protein (data not shown).

Kinetic Properties of Purified His-MT-SP1 Protease Domain

The enzyme concentration was determined using an active site titration with MUGB. The catalytic activity of the protease domain was monitored using pNA substrates. Purified protease domain was tested for hydrolytic activity against tetrapeptide substrates of the form Suc-AAPX-pNA, which contained various amino acids at the P1 position (P1-Ala, Asp, Glu, Phe, Leu, Met, Lys, or Arg). The only substrates with detectable activity were those with P1-Lys or P1-Arg. The serine protease domain with the Ser$^{805}$Ala mutation had no detectable activity. The activity of the protease domain was further characterized using the substrate Spectrozyme tPA (hexahydrotyrosyl-Gly-Arg-pNA), yielding: $K_m = 31.4 \pm 4.2$ μM, $k_{cat} = 2.6 \times 10^2 \pm 6.5$ s$^{-1}$, and $k^{cat}/K_m = 6.9 \times 10^6 \pm 2.3 \times 10^6$ M$^{-1}$s$^{-1}$. Ecotin inhibition of the MT-SP1 His-tagged protease domain fits a tight-binding reversible inhibitory model as observed for ecotin interaction with other serine protease targets. Inhibition assays using ecotin and ecotin M84R/M85R yielded apparent K's of 782±92 pM and 9.8±1.5 pM respectively.

Discussion

Structural Motifs of MT-SP1

In this work, we characterize the expression of chymotrypsin-fold proteases by PC-3 cells and cloned a member of this family we call MT-SP1. The name membrane-type serine protease 1 (MT-SP1) is given to be consistent with the nomenclature of the membrane-type matrix metalloproteases (MT-MMPs) (Nagase (1997) *Biol. Chem.* 378, 151–160). The cDNA likely encodes a membrane-type protein due to the lack of a signal sequence and the presence of a putative signal anchor (SA) that is also seen in other membrane-type serine proteases hepsin (Leytus et al. (1988) *Biochemistry* 27: 1067–1074), enteropeptidase (Kitamoto et al. (1994) *Proc. Natl. Acad. Sci. USA* 91: 7588–7592), TMPRSS2 (Poloni-Giacobino et al. (1997) *Genomics* 44, 309–320), and human airway trypsin-likeprotease (Yamakoka et al. (1998) *J. Biol. Chem.* 273, 11895–11901). We propose that proteins that are localized to the membrane through a signal anchor and that encode a chymotrypsin fold serine protease domain be categorized in the MT-SP family. The membrane localization of MT-SP1 is supported by immunofluorescence experiments that localize the protease domain to the extracellular cell surface.

Following the putative SA are several domains that are thought to be involved in protein-protein interactions or protein ligand interactions. For example, CUB domains can mediate protein-protein interactions, as with the seminal plasma PSP-I/PSP-II heterodimer that is built by CUB domain interactions and with procollagen C-proteinase enhancer protein and procollagen C-proteinase (BMP-1) (Kessler and Adar (1989) *Eur. J. Biochem.* 186, 115–121; Hulmes et al. (1997) *Matrix Biol.* 16, 41–45). Interestingly, most of the proteins that contain CUB domains are involved in developmental processes or are involved in proteolytic cascades, which suggests that MT-SP1 may play a similar role. The four repeated motifs that follow the CUB domains are known as LDL receptor ligand-binding repeats, named after the seven copies of repeats found in the LDL receptor. There are several negatively charged amino acids between the fourth and sixth cysteines that are highly conserved in the LDL receptor and also seen in the LDLR repeats of MT-SP1. The conserved motif Ser-Asp-Glu (residues 44–46 in FIG. 4) are known to be important for binding the positively charged residues of the LDL receptor ligands apolipoprotein B-100 (ApoB-100) and ApoE. The ligand binding repeats of MT-SP1 most likely do not mediate interaction with ApoB-100 or ApoE, but may be involved in the interaction with other positively charged ligands. For example, LDLR repeats in the LDL receptor-related protein have been implicated the binding and recycling of protease/inhibitor complexes such as uPA/plasminogen activator inhibitor-1 (PAI-1) complexes (reviewed in Strickl et al. (1995) *FASEB J.* 9, 890–898; Moestrup (1994) *Biochim. Biopys. Acta* 1197, 197–213). It also has been shown that the pro domain of enteropeptidase is involved in interactions with its substrate trypsinogen, allowing 520-fold greater catalytic efficiency in the cleavage compared to the protease domain alone (Lu et al. (1997) *J. Biol. Chem.* 272, 31293–31300). By analogy, similar interactions should occur between MT-SP1 and its substrates. Thus, further investigation of MT-SP1 CUB domain or LDLR repeat interactions may yield insight into the function of this protein.

The amino acid sequence of the serine protease domain of MT-SP1 is highly homologous to other proteases found in the family (FIG. 4). The essential features of a functional serine protease are contained in the deduced amino acid sequence of the domain. The residues that comprise the catalytic triad, $His^{656}$, $Asp^{711}$, $Ser^{805}$, corresponding to $His^{57}$, $Asp^{102}$, and $Ser^{195}$ in chymotrypsin, are observed in MT-SP1 (see Perona and Craik (1995) *Protein Sci.* 4: 337–360, Perona and Craik (1997) *J. Biol. Chem.* 272: 29987–29990 for reviews). The sequence $Ser^{214}$-$Trp^{215}$-$Gly^{216}$ ($Ser^{825}$-$Trp^{826}$-$Gly^{827}$), which is thought to interact with the side chains of the substrate for properly orienting the scissile bond is present. $Gly^{193}$ ($Gly^{803}$) and $Gly^{196}$ ($Gly^{805}$), which are thought to be necessary for proper orientation of $Ser^{195}$ ($Ser^{805}$) also are present. Based upon homology to chymotrypsin, three disulfide bonds are predicted to form within the protease domain at $Cys^{44}$-$Cys^{58}$, $Cys^{168}$-$Cys^{182}$, and $Cys^{191}$-$Cys^{220}$ ($Cys^{643}$-$Cys^{657}$, $Cys^{776}$-$Cys^{790}$, $Cys^{801}$-$Cys^{830}$), and a fourth disulfide bond should form between the catalytic and the pro-domain $Cys^{122}$-$Cys^{1}$ ($Cys^{731}$-$Cys^{604}$), as observed for chymotrypsin. This predicted disulfide with the pro-domain suggests that the active catalytic domain should still be localized to the cell surface via a disulfide linkage. The presence of the catalytic machinery and other conserved structural components described above suggest that all features necessary for proteolytic activity are present in the encoded sequence.

Substrate Specificity of the MT-SP1 Protease Domain

The S1 site specificity (Schecter and Berger (1967) *Biochem. Biophys. Res. Commun.* 27: 157–162) of a protease is largely determined by the amino acid residue at position 189. This position is occupied by an aspartate in MT-SP1, suggesting that the protease has specificity for Arg/Lys in the P1 position. In addition, the presence of a polar $Gln^{192}$ ($Gln^{803}$), as in trypsin is consistent with basic specificity. Furthermore, the presence of $Gly^{216}$ ($Gly^{827}$) and $Gly^{216}$ ($Gly^{837}$) is consistent with the presence of a deep S1 pocket, unlike elastase, which has $Val^{216}$ and $Thr^{226}$ that block the pocket and thereby contribute to the P1 specificity for small hydrophobic side chains. The specificity at the other subsites is largely dependent upon the nature of the seven loops A–E and loops 2 and 3 (FIG. 4). Loop. C in enterokinase has a number of positively charged residues that are thought to interact with the negatively charged activation site in trypsinogen, Asp-Asp-Asp-Asp-Lys (SEQ ID NO:8). One known substrate for MT-SP1 (as described below) is the activation site of MT-SP1, which is Arg-Gln-Ala-Arg (residues 611–614). Loop C contains two aspartate residues that may participate in the recognition of the activation sequence.

One means of obtaining further data on substrate specificity is by characterization of the activity of the recombinant proteolytic domain. Enterokinase has been characterized from both recombinant (LaVallie et al. (1993) *J. Biol. Chem.* 268: 23311–23317) and native (Light and Fonseca (1984) *J. Biol. Chem.* 259: 13195–13198; Matsushima et al. (1994) *J. Biol. Chem.* 269: 19976–19982) sources. However proteolytic activity for the other reported membrane-type serine proteases hepsin (Leytus et al. (1988) *Biochemistry* 27: 1067–1074) and TMPRSS2 (Poloni-Giacobino et al. (1997) *Genomics* 44: 309–320) are only predicted based upon sequence homology. In order to produce active recombinant MT-SP1, a His-tagged fusion of the protease domain was cloned into an *E. coli* vector and expressed and purified to homogeneity. Fortuitously, the protease domain refolded and autoactivated after resuspension and purification from inclusion bodies. This activity, coupled with the lack of activity in the $Ser^{195}$Ala ($Ser^{805}$Ala) variant, demonstrates that the cDNA encodes a catalytically proficient protease. Autoactivation of the protease domain at the arginine-valine site ($Arg^{614}$–$Val^{615}$) shows that the protease has Arg/Lys specificity as predicted by the sequence homology to other proteases of basic specificity. Specificity and selectivity are confirmed by the lack of cleavage of AAPX-pNA substrates that do not have X=R, K. Further characterization with hexahydrotyrosyl-Gly-Arg-pNA (Spectrozyme tPA) revealed an active enzyme with $k_{cat} = 2.6 \times 10^2/s$. However, the His-tagged serine protease domain does not cleave H-Arg-pNA, showing that, unlike trypsin, there is a requirement for additional subsite occupation for catalytic activity. This suggests that the enzyme is involved in a regulatory role that requires selective processing of particular substrates rather than non-selective degradation.

MT-SP1 Function

In other studies, we have found that inhibition of serine protease activity by ecotin or ecotin M84R/M85R inhibits testosterone-induced branching ductal morphogenesis and enhances apoptosis in a rat ventral prostate model. Moreover, the rat homolog of MT-SP 1 is expressed in the normal rat ventral prostate (data not shown). Assays of the protease domain with ecotin and ecotin M84R/M85R showed that the enzymatic activity is strongly inhibited (782±92 pM, 9.8±1.5 pM respectively), suggesting that rat MT-SP1 is likely to be inhibited at the concentrations of these inhibitors used in our experiments. MT-SP1 inhibition may result in the observed inhibition of differentiation and/or increased apoptosis. Future studies are aimed at definitively resolving the role of MT-SP1 in prostate differentitation. The broad expression of MT-SP1 in epithelial tissues is consistent with the possibility that it is involved in cell maintenance or growth and differentiation, perhaps by activating growth factors or by processing prohormones. Studies examining the direct role of MT-SP1 in differentiation and growth of the epithelium in glandular tissues like the prostate are underway.

MT-SP1 may participate in a proteolytic cascade that results in cell growth and or differentiation. Another structurally similar membrane-type serine protease, enteropeptidase (FIG. 3), is involved in a proteolytic cascade by which activation of trypsinogen leads to activation of downstream intestinal proteases (5). Enteropeptidase is expressed only in the enterocytes of the proximal small intestine thus precisely restricting activation of trypsinogen. Thus, in contrast to secreted proteases that may diffuse throughout the organism, the membrane association of MT-SP1 should also allow the proteolytic activity to be precisely localized, which may be important for proper physiological function; improper localization of the enzyme or levels of downstream substrates could lead to disease.

We have found subcutaneous coinjection of PC-3 cells with wild-type ecotin or ecotin M84R/M85R led to a decrease in the primary tumor size compared to animals in whom PC-3 cells and saline were injected. Since wild-type ecotin is a poor, micromolar inhibitor of uPA, serine proteases other than uPA likely are involved in this primary tumor proliferation. Both wild-type ecotin and ecotin M84R/M85R are potent, subnanomolar inhibitors of MT-SP1, raising the possibility that MT-SP1 plays an important role in progression of epithelial cancers expressing this protease.

Ecotin injected intraperitoneally also inhibited tumor growth indicating that treatment by administration of MT-SP1 modulators can be accomplished using systemic administration.

Direct biochemical isolation of the substrates may be possible if MT-SP1 adhesive domains such as the CUB domains or LDLR repeats interact with the substrates. In addition, likely substrates may be predicted and tested using knowledge of extended enzyme specificity. For example, the characterization of the substrate specificity of granzyme B allowed the prediction and confirmation of substrates for this serine protease (Harris et al. (1998) *J. Biol. Chem.* 273: 27364–27373). Thus, these complimentary studies should further shed light on the physiological function of this enzyme.

Example 2

Membrane-type serine protease 1 (MT-SP1) was identified as a transmembrane protease expressed by a human prostate cancer cell line, PC-3. We have examined the expression of MT-SP1 in gastric cancer tissues and assessed the potential role of this protease in cancer progression. Western blot and RT-PCR analysis demonstrated exclusive expression of MT-SP1 in the cancer tissues of some cases. Immunohistochemically, MT-SP1 was localized in cancer cells, endothelial cells and leukocytes. Because the expression in endothelial cells was especially intense, its labeling index (LI) was calculated (0–98, 31±5%). MT-SP1 LI was significantly higher in specimens of poorly differentiated gastric cancer than in well differentiated cancer specimens (46±10, 15±6%, respectively, p<0.05). The 11 patients with high MT-SP1 expression >=40%) had a lower survival rate than the 21 patients with low MT-SP1 expression (<40%) or the 9 patients without MT-SP1 expression (p<0.05). These results suggest that MT-SP1 expression in endothelial cells may play an important role in angiogenesis in cancer tissues and is a significant prognostic factor in gastric cancer.

Materials and Methods

Materials.

Surgical specimens of primary tumors obtained from 41 patients who underwent gastrectomy for gastric cancer between 1985 and 1995 at the Santa Clara Valley Medical Center, San Jose, Calif. and the Palo Alto Veteranis Affair Medical Center, Palo Alto, Calif., were subjected to immunohistochemical analysis. In addition, surgically resected specimens of gastric cancer and adjacent normal tissue from two patients at the National Defense Medical College Hospital, Japan were used for Western and mRNA analysis. Depth of tumor invasion, lymph node involvement, distant metastases and pathologic characteristics were evaluated for each tumor. TNM classification by the UICC was used for stage grouping (Hermanek and Sobin (1992) *UICC TNM classification of malignant tumours.*, 4th ed. 2nd rev. edition. Berlin: Springer-Verlag). Tumor histology was divided into three groups: well differentiated, moderately differentiated and poorly differentiated adenocarcinomas.

Western Immunoblotting Analysis.

We compared MT-SP1 expression in cancer tissue with that in adjacent normal tissue, using immunoblotting analysis. Surgical samples were homogenized in PBS (phosphate-buffered saline) containing 0.1% Triton X-100. The extracts were electrophoresed on 10% SDS-polyacrylamide gels then electrically transferred to polyvinylidene difluoride membrane. Membranes were treated with nonfat milk to reduce nonspecific binding, then incubated for 1 h at room temperature with the primary antibody. After extensive washing, blots were incubated with peroxidase-conjugated second antibodies and developed with detection reagents. Protein content was measured using the BCA protein assay and bovine serum albumin as the standard (Pierce, Rockford, Ill.).

RT-PCR.

mRNA was extracted from each specimen and purified using the RNA STAT-60TM kit (Tel-test, Inc., Friendswood, Tex.). Tissues were homogenized, lysed, and mRNA extracted and purified according to the vendoris suggested protocol mRNA was quantified by measuring the spectroscopic absorbance at 260 and 280 nm. RT-PCR was performed with the Titan™ one tube RT-PCR system according to the manufacturer's protocol (Boehringer Mannheim, Indianapolis, Ind.). One mg of template RNA was reverse transcribed to cDNA in 50 ml of reaction tube with 15 mM $MgCl_2$, 0.2 mM deoxynucleotide mix, 20 pmol of each MT-SP1 primer, enzyme mix at 50° C. for 30 min. The produced cDNA was directly amplified using a thermal cycler. Initial denaturation was done at 94° C. for 2 min followed by 10 and 25 cycles of amplification. The first cycle consisted of 30 s of denaturation at 94° C., 30 s of annealing at 55° C., and 90 s for enzymatic primer extension at 68° C. The final extension was carried out at 68° C. for 7 min. The following oligonucleotides were used as RT-PCR primers: MT-SP1—F: 5'-TGC GAC AGT GTG AAC GAC TGC GGA GAC AAC-3' (SEQ ID NO: 32); and MT-SP1-R: 5'-CTC CAC GCT GGA CAG GGG TCC CCC GGA ATC-3' (SEQ ID NO: 33).

As a positive control, we used RNA extract from PC-3 cells (human prostate cancer cell line). Aliquots (10 mcl) of the RT-PCR produce were electrophoresed in 1.5% agarose gel in 1×TAE (40 mM Tris acetate/2 mM sodium EDTA/ glacial acetic acid, pH 8.8) containing 0.5 μg ethidium bromide.

Immunohistochemistry

Surgical specimens were preserved in a 10% neutralized formaldehyde solution. Each block of paraffin-embedded tumor specimen was cut into 5 mm sections and deparaffinized in xylene and ethanol, then immersed in 3% hydrogen peroxide-methanol to inhibit endogenous peroxidase. After treatment with normal goat serum, the sections were incubated with a 1:100 dilution of rabbit antihuman MT-SP1 antibody overnight at 4° C. They wer washed then treated consecutively with a biotinylated goat anti-rabbit antibody for 1 h. The 3,3'-diaminobenzidine substrate kit and Vectastain Elite ABC kit (Vector Laboratories) were used according to the manufacturer's suggested protocol. Counterstaining was performed with hematoxylin. Negative controls for the immunostaining were carried out by replacing the primary antibody with preimmune rabbit immunoglobulin. Vessel rings were counted at 200× magnification. Ten fields were counted for each case, and the proportion of total rings that were MT-SP1-positive was defined as the MT-SP1 labeling index (MT-SP LI).

Statistics.

Results shown are the mean±SE. Spearman rank correlation analysis was used to correlate the degree of each histopathologic factor with MT-SP LI. The cumulative survival rates were calculated by the method of Kaplan-Meier. The survival rates for different groups of patients were compared by the generalized Wilcoxon test. The specific contribution of prognostic variables was examined by means of a multivariate Coxis proportional hazard model. A p value of less than 0.05 was considered statistically significant.

Results

Immunoblotting for MT-SP1.

Tissue from two cases of stomach cancer were analyzed by Western immunoblotting using equal amounts (by weight) of cell lysates from cancerous and adjacent normal stomach tissue. Using a polyclonal antiserum produced against MT-SP1, the presence of two bands (45 and 100 kD), most intense in the tumor tissue of case 2 (FIG. 1), were demonstrated. These two bands in tumor and adjacent normal tissues from case 1 were less intense.

RT-PCR Analysis for MT-SP1.

Analysis of MT-SP1 mRNA from stomach tissues demonstrated the expression in only tumor tissue of case 2 but not in that of case 1. MT-SP1 was not detectable by RT-PCR in adjacent normal tissue of either case.

Immunohistochemistry.

We used the immunohistochemical assay to study MT-SP1 expression in gastric cancer tissues. We detected MT-SP1 immunoreactivity in cancer cells, the luminal surface of blood vessels, presumably endothelial cells, and some leukocytes. Since the immunoreactivity in blood vessels in cancer stroma was especially intense, we focused on the correlation between MT-SP1 expression in blood vessels and clinicopathologic factors in gastric cancer.

Relationship Between MT-SP LI and Clinicopathologic Factors.

MT-SP1 expression in blood vessels of cancer stroma did not correlate with UICC TNM classification. Poorly differentiated tumors showed significantly higher MT-SP LI than well differentiated tumors. Tumors with pT1 showed low MT-SP LI as compared to those with deeper invasion than submucosa but there were no statistically significant differences.

Relationship Between MT-SP LI and Survival.

There were no significant differences in the overall survival rates between the MT-SP positive group (MT-SP LI>0%) and the MT-SP negative group (MT-SP LI=0%). However, when the patients in the MT-SP positive group were divided into two groups according to the average index (40%) in MT-SP LI as a cutoff point, eleven patients with a high expression of MT-SP1 (MT-SP LI>=40%) in blood vessels showed a lower survival rate than 21 patients with low expression of MT-SP1 (MT-SP LI: 40%) or 9 patients with no expression of MT-SP1 (P,0.05). The five-year survival ratge wfor patients with an MT-SP LI of 40% or higher was 27.3% versus 47.1% for patients with an MT-SP LI lower than 40% or 45.7% for patients with negative expression of MT-SP1.

Prognostic Analysis of MT-SP1 in Endothelium According to Pathological Staging.

Kaplan-Meier survival calculations were performed for stages I, II and stages III, IV separately. In stages III, IV, patients (n=30) with an MT-SP LI of 40% or higher had a significantly lower survival rate than those (n=11) without MT-SP1 expression in vascular cells of cancer tissues (p<0.05). For stages I, II, however, there was no difference in survival among the three groups.

For multivariate analysis, MT-SP1 expression in blood vessels around cancer cells and established risk factors in gastric cancer were categorized into two classes. MT-SP1 expression was subdivided into two categories; i) with an MT-SP LI less than 40%, ii) with an MT-SP LI of 40% or higher. The depth of tumor invasion and lymph node involvement were subdivided into two categories; pT1,2 (n=19) and pT3,4 (n=22), pN0,1 (n=27) and pN2 (n=14), respectively. These characteristics were confirmed to be significant prognostic determinants in the generalized Wilcoxon test. In Coxis regression model, higher expression of MT-SP1 in blood vessels around cancer cells proved to worsen survival independently, following serosal or deeper invasion of primary tumor.

DISCUSSION

MT-SP1 was identified, initially, in a prostate cancer cell line. We believe it is involved in homeostatic processes occurring in the pericellular milieu. The cDNA sequence of MT-SP1 encodes a mosaic protein that contains a transmembrane signal anchor and a serine protease domain, which is also seen in other membrane-type serine proteases hepsine (Leytus et al. (1988) *Biochemistry* 27: 1067–1074), enteropeptidase (Kitamoto et al. (1994) *Proc Natl Acad Sci USA*, 91: 7588–7592), and TMPRSS2 (Paoloni-Giacobino et al. (1997) *Genomics*, 44: 309–320). Recently a similar cDNA was cloned from mouse thymic stromal cells which was named epithin (Kim et al. (1999) *Immunogenetics* 49: 420–428). An open reading frame was identified that encoded a 902 amino acid protein with a C-terminal serine protease domain, 4 LDLR domains, and two cub domains. A high level of expression was seen by Northern blotting in mouse intestine and kidney. mRNA was not detected in brain, heart, liver, testis or skeletal muscle. In some tissues, different forms of mRNA were seen suggesting the possibility of alternative splicing or alternative polyadenylation sites. Epithin was localized to mouse chromosome 9, ~16 cM from the centromere.

It is thought that MT-SP1 which is localized to the plasma membrane through a signal anchor is a component of proteolytic cascades involved in developmental processes, and physiologic reactions on the surface of the gastro-intestinal and genito-urinary epithelium. MT-SP1 is expressed in various malignant epithelial tissues including the digestive and urinary tracts suggesting that it may also have a role in cancer progression. Recently, Lin et al. reported expression of a similar protease in human breast cancer cells which was termed, Matriptase. (Lin et al. (19_) *J. Biol. Chem.* 274: 18237–18242). A complex of this protease with a Kunitz-type inhibitor was also fond in human breast milk (however, since the characterization of its physiological substrate(s) have not been completed, the function of this novel enzyme in cancer progression is unclear).

In this example, we have clarified a relationship between the expression of MT-SP1 and clinicopathological factors in gastric cancer. The molecular weight of the entire MT-SP1 protein is predicted as approximately 100 kD which is consistent with our immunoblotting analysis. In this analysis, another band was shown at the molecular weight of 45 kD. This band is likely to represent the activated form of the protease domain of MT-SP1 that is released from the pro-domain under reducing conditions. Although the expected molecular weight of this form is 28 kD, this difference might be due to glycosylation of the protease domain.

Immunohistochemical examination of gastric cancer tissue revealed MT-SP1 expression in cancer cells, endothelial cells and some leukocytes. In these tissues, endothelial cells showed especially intensive MT-SP1 immunoreactivity. This suggests that MT-SP1 plays an important role in vascular cells. Although there was not a significant correlation between MT-SP1 expression in endothelial cells of gastric cancer tissue and pathological staging, MT-SP1 was highly expressed in the endothelium of the poorly differentiated adenocarcinomas. Moreover, overall survival for groups of gastric carcinoma patients with highly MT-SP1 expressing endothelium revealed poor prognosis compared to those with low or no MT-SP1. Higher MT-SP1 expression in endothelium was significantly associated with lower survival rate. These results suggested that MT-SP1 expression in endothelium around cancer cells might be an important prognostic factor in gastric cancer.

MT-SP1 expression in vessels within the cancer matrix may contribute to angiogenesis in gastric cancer tissue. Some angiogenic factors such as vascular endothelial growth factor (VEGF) (Ferrara et al. (1991) *Meth. Enzymol.* 198: 391–405, Melnyk (1996) *Cancer Res.* 56: 921–924) derived from cancer cells might be associated with the MT-SP1 expression in endothelial cells. The interaction between cancer cells and stromal cells in cancer tissue is likely to be important for invasion and metastasis as described in other reports(Romer et al. (1994) *Int J Cancer.* 57: 553–560; Sieuwerts et al. (1988) *Int J Cancer.* 76: 829–835).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An isolated nucleic acid consisting of a nucleic acid sequence selected from:
   (a) a nucleic acid sequence consisting of a sequence encoding a serine proteinase domain that is at least 95% identical to the amino acid sequence from residue 615 to 855 shown in SEQ ID NO. 2 and optionally a fusion protein thereto, wherein said domain exhibits serine proteinase actitivity; and
   (b) a complement of the nucleic acid sequence of (a).

2. The isolated nucleic acid of claim 1, wherein said serine protease domain of (a) has the sequence of amino acids 615 through 855 of SEQ ID NO:2.

3. The isolated nucleic acid of claim 1, wherein the serine protease domain exhibits protease activity in the presence of a target substrate.

4. The isolated nucleic acid of claim 3, wherein the target substrate has the formula of Suc-AAPX-pNA, wherein:
   Suc is N-succinyl,
   A is alanyl, and
   X is selected from the group consisting of alanyl, aspartyl, glutamyl, penylalanyl, leucinyl, methionyl and arginyl residue.

5. A vector comprising the nucleic acid of claim 1.

6. A host cell comprising the isolated nucleic acid of claim 1.

7. A process of producing a polypeptide comprising culturing the host cell of claim 6 under conditions suitable for protein expression.

8. The isolated nucleic acid of claim 1 encoding a fusion protein comprising said serine proteinase domain that is at least 95% identical to the amino acid sequence of residue 615 to 855 shown in SEQ ID NO.2.

9. The isolated nucleic acid of claim 3 wherein the target substrate is substrate Spectrozyme tPA.

* * * * *